United States Patent
Baik et al.

(10) Patent No.: US 9,815,840 B2
(45) Date of Patent: Nov. 14, 2017

(54) PROTEIN KINASE INHIBITOR CONTAINING PYRROLOPYRIDAZINE DERIVATIVE

(71) Applicant: CJ Healthcare Corporation, Seoul (KR)

(72) Inventors: Tae Gon Baik, Gyeonggi-do (KR); Won-Hyuk Jung, Gyeonggi-do (KR); Seung In Kim, Daejeon (KR); Seung Chan Kim, Gyeonggi-do (KR); Sook Kyung Park, Seoul (KR); Su Yeon Jung, Gyeonggi-do (KR); Seung Hee Ji, Seoul (KR); So Young Ki, Gyeongsangnam-do (KR); Min Cheol Kim, Gyeonggi-do (KR); Eun Young Lee, Seoul (KR); Eun Mi Hong, Gyeonggi-do (KR)

(73) Assignee: The Asan Foundation, Seoul (KR)

( * ) Notice: Subject to any disclaimer, the term of this patent is extended or adjusted under 35 U.S.C. 154(b) by 0 days.

(21) Appl. No.: 14/916,177

(22) PCT Filed: Aug. 29, 2014

(86) PCT No.: PCT/KR2014/008083
§ 371 (c)(1),
(2) Date: Mar. 2, 2016

(87) PCT Pub. No.: WO2015/034213
PCT Pub. Date: Mar. 12, 2015

(65) Prior Publication Data
US 2016/0207931 A1    Jul. 21, 2016

(30) Foreign Application Priority Data

Sep. 4, 2013    (KR) .................. 10-2013-0106063

(51) Int. Cl.
*C07D 487/04* (2006.01)
*A61K 31/5025* (2006.01)

(52) U.S. Cl.
CPC ........ *C07D 487/04* (2013.01); *A61K 31/5025* (2013.01)

(58) Field of Classification Search
None
See application file for complete search history.

(56) References Cited

U.S. PATENT DOCUMENTS

| 7,348,325 B2 | 3/2008 | Cai et al. |
| 7,439,246 B2 | 10/2008 | Borzilleri et al. |
| 7,759,344 B2 | 7/2010 | Booker et al. |
| 2006/0211695 A1 | 9/2006 | Borzilleri et al. |
| 2007/0123534 A1 | 5/2007 | Cai et al. |
| 2008/0234268 A1 | 9/2008 | Booker et al. |

FOREIGN PATENT DOCUMENTS

| KR | 10-0979439 B1 | 8/2010 |
| WO | WO 2006/021881 A2 | 3/2006 |
| WO | WO 2010/044543 A2 | 4/2010 |

OTHER PUBLICATIONS

Underiner et al. Anti-Cancer Agents in Medicinal Chemistry, vol. 10, p. 7-27 (2010).*
Cancer Drug Design and Discovery, Neidle, Stephen, ed. (Elsevier/Academic Press), pp. 427-431 (2008).*
Bottaro et al., "Identification of the Hepatocyte Growth Factor Receptor as the c-met Proto-Oncogene Product," *Science* (1991), 251:802-804.
Zhou et al., "Altered Expression of the RON Receptor Tyrosine Kinase in Primary Human Colorectal Adenocarcinomas: Generation of Different Splicing RON Variants and their Oncogenic Potential," *Oncogene* (2003), 22:186-197, Nature Publishing Group.

* cited by examiner

*Primary Examiner* — Emily Bernhardt
(74) *Attorney, Agent, or Firm* — DLA Piper LLP (US)

(57) ABSTRACT

The present invention relates to a pyrrolopyridazine derivative represented by Formula 1 of the detailed description, or a pharmaceutically acceptable salt thereof. The compound according to the present invention and a pharmaceutically acceptable salt thereof can inhibit the activity of protein kinase(s), and thus are useful for preventing or treating diseases related thereto.

[Formula 1]

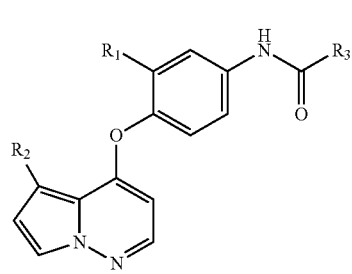

15 Claims, No Drawings

PROTEIN KINASE INHIBITOR CONTAINING PYRROLOPYRIDAZINE DERIVATIVE

CROSS-REFERENCE TO RELATED APPLICATIONS

This application is a 35 USC §371 National Stage application of International Application No. PCT/KR2014/008083 filed Aug. 29, 2014, now pending; which claims the benefit under 35 USC §119(a) to Korea Patent Application Serial No. 10-2013-0106063 filed Sep. 4, 2013. The disclosure of each of the prior applications is considered part of and is incorporated by reference in the disclosure of this application.

BACKGROUND OF THE INVENTION

Field of the invention

The present invention relates to a novel compound that can be effectively used for The prevention or treatment for protein kinase-related diseases by inhibiting proteins kinase(s), and a pharmaceutical composition containing the same.

Background Information

Protein kinases are enzymes which control various intracellular processes by regulating activities, positions, and functions of other proteins via phosphorylation. Abnormalities of protein kinases are closely associated with mechanisms of diseases such as cancer, immune diseases, nerve disorders, metabolism disorders and infections. Examples of protein kinases include Abl, ACK, ALK, Arg, ARK5, Aurora, Axl, Bmx, BTK, CDK, CHK, c-Kit, c-Met, c-RAF, c-SRC, EGFR, FAK, Fes, FGFR, Flt3, GSK3, IGF, IKK, JAK, Lck, LIMK, Lyn, MEK, Mer, MK-2, P38alpha, PDGFR, PDK, Pim, PKA, PKB, PKCR, Plk-1/3, Ret, Ron, Ros, Rse, Tie, Trk, Tyro3, VEGFR, YES, etc.

c-Met is a cell membrane receptor which plays an essential role in embroyonic development and wound healing. Hepatocyte growth factor (HGF) is a ligand of c-Met receptors and promotes tumor growth, angiogenesis, invasion, and metastasis (Bottaro D P, Rubin J S, Faletto D L, Chan A M, Kmiecik T E, Vande Woude G F, Aaronson S A: Identification of the hepatocyte growth factor receptor as the Met proto-oncogene product. Science 1991, 251 (4995), 802-804).

Abnormal c-Met activation in cancer cells is correlated with deterioration of prognosis in cancer treatment, and overexpression and mutations of c-Met have been observed in various kinds of cancers including non-small cell lung cancer. Since the invasion and metastasis of tumors are major cause of death, the inhibition of c-Met signaling is expected to be effective in cancer treatment.

Recepteur d'Origine receptor (RON), a protein receptor belonging to c-Met series, is secreted by the liver and is a receptor for macrophage-stimulating protein (MSP), which is a serum protein regulating the actions of macrophages (Zhou Y Q, He C, Chen Y Q, Wang D, Wang M H: Altered expression of the RON receptor tyrosine kinase in primary human colorectal adenocarcinomas: generation of different splicing RON variants and their oncogenic potential. Oncogene 2003, 22(2):186-197). The expression of RON is abnormally controlled in breast cancer cells and colorectal cancer cells, and in particular, it is closely related with metastasis of colorectal cancer. For example, IMC-41A10, which is a monoclonal antibody binding to RON, has been reported to inhibit metastasis and tumorigenesis, and thus RON inhibitors are expected to show excellent effects against carcinogenesis or cancer metastasis.

In this regard, Korean Patent No. 10-0979439 discloses pyridine derivatives substituted with pyrazole and benzoxazole which have inhibitory activity against protein kinases, e.g., c-Met, etc., and Korean Patent No. 10-0869393 discloses pyrazole-substituted aminoheteroaryl compounds having an inhibitory activity against c-Met protein kinase.

Under these circumstances, the present inventors have endeavored to develop a novel compound that can be used as a protein kinase inhibitor, and as a result, have discovered that the pyrrolopyridazine derivatives described in the specification can effectively inhibit the activities of protein kinases to be effectively used for the prevention or treatment for cancer, psoriasis, rheumatoid arthritis, inflammatory bowel disease, or chronic obstructive pulmonary disease, thereby completing the present invention.

SUMMARY OF THE INVENTION

Technical Problem

An object of the present invention is to provide a novel pyrrolopyridazine derivative that can be effectively used for the prevention or treatment for protein kinase-related diseases by inhibiting protein kinase(s), and a pharmaceutical composition containing the same.

Additionally, another object of the present invention is to provide a method for inhibiting the activity of protein kinase(s) using a composition containing a novel pyrrolopyridazine derivative or a pharmaceutically acceptable salt thereof as an active ingredient, and preferably inhibiting the activity of c-Met.

Technical Solution

In order to accomplish the above objects, the present invention provides a compound represented by the following Formula 1 or a pharmaceutically acceptable salt thereof:

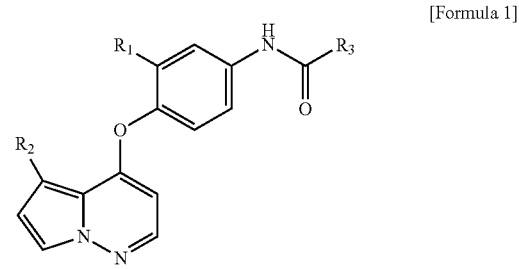

[Formula 1]

wherein, in Formula 1, $R_1$ is H or halogen;

$R_2$ is aryl or heteroaryl selected from the group consisting of indolyl, phenyl, pyrazinyl, pyrazolyl, pyridinyl, pyrimidinyl, thiazolyl, and thienyl, wherein the aryl or the heteroaryl is unsubstituted or substituted with one or two substituents, which are respectively and independently selected from the group consisting of

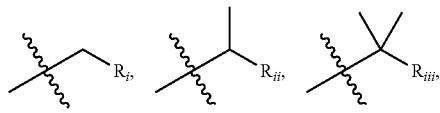

$C_{1-4}$ alkyl, $C_{1-4}$ alkoxy, halogen, nitro, cyano, amino, $NH(C_{1-4}$ alkyl), NH-acetyl, CO—H, CO—$(C_{1-4}$ alkyl), CO-morpholino, CO—$NH_2$, CO—$NH(C_{1-4}$ alkyl), CO—$N(C_{1-4}$ alkyl)$_2$, morpholino, piperazinyl, piperidinyl, $SO_2$—$(C_{1-4}$ alkyl)$_2$, $SO_2$—$NH_2$, $SO_2$—$NH(C_{1-4}$ alkyl), and $SO_2$—$N(C_{1-4}$ alkyl)$_2$; wherein $R_i$ is selected from the group consisting of hydroxy, O—$CH_2CH_2$—O—$CH_3$, OCO—$NH_2$, morpholino, amino, $NH(C_{1-4}$ alkyl), and $N(C_{1-4}$ alkyl)$_2$; $R_{ii}$ is hydroxy or $C_{1-4}$ alkoxy; and $R_{iii}$ is hydroxy; and $R_3$ is

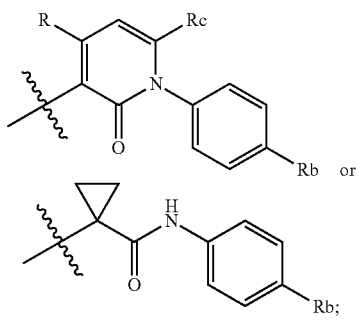

wherein Ra is H or $C_{1-4}$ alkoxy; Rb is H or halogen; and Rc is H or $C_{1-4}$ alkyl.

Preferably, $R_1$ is H or fluoro.

Preferably, the substituent for the aryl or heteroaryl in $R_2$ is selected from the group consisting of

(wherein $R_i$ is selected from the group consisting of hydroxy, O—$CH_2CH_2$—O—$CH_3$, OCO—$NH_2$, morpholino, amino, $NHCH_3$, $NHCH_2CH_3$, and $N(CH_3)_2$),

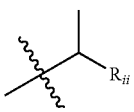

(wherein $R_{ii}$ is hydroxy or methoxy),

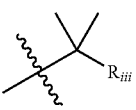

(wherein $R_{iii}$ is hydroxy), methyl, methoxy, fluoro, chloro, nitro, cyano, amino, methylamino, ethylamino, NH-acetyl, CO—H, CO—$CH_3$, CO-morpholino, CO—$NH_2$, CO—$NHCH_3$, CO—$N(CH_3)_2$, morpholino, piperazinyl, piperidinyl, $SO_2$—$CH_3$, $SO_2$—$CH_2CH_3$, $SO_2$—$NH_2$, $SO_2$—$NHCH_3$, and $SO_2$—$N(CH_3)_2$.

Preferably, $R_2$ is phenyl, wherein the phenyl is unsubstituted or substituted with one or two substituents, which are respectively and independently selected from the group consisting of

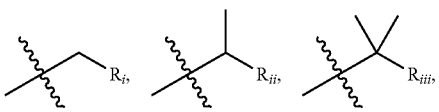

$C_{1-4}$ alkoxy, halogen, nitro, cyano, amino, $NH(C_{1-4}$ alkyl), CO—H, CO—$(C_{1-4}$ alkyl), CO-morpholino, CO—$NH_2$, CO—$NH(C_{1-4}$ alkyl), CO—$N(C_{1-4}$ alkyl)$_2$, $SO_2$—$(C_{1-4}$ alkyl), $SO_2$—$NH_2$, $SO_2$—$NH(C_{1-4}$ alkyl), and $SO_2$—$N(C_{1-4}$ alkyl)$_2$, in which $R_i$ is selected from the group consisting of hydroxy, O—$CH_2CH_2$—O—$CH_3$, OCO—$NH_2$, morpholino, amino, $NH(C_{1-4}$ alkyl), and $N(C_{1-4}$ alkyl)$_2$, $R_{ii}$ is hydroxy or $C_{1-4}$ alkoxy, and $R_{iii}$ is hydroxy.

Preferably, $R_2$ is pyridinyl, in which the pyridinyl is unsubstituted or substituted with a substituent, which is selected from the group consisting of

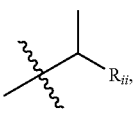

$C_{1-4}$ alkoxy, halogen, amino, NH-acetyl, CO—$(C_{1-4}$ alkyl), morpholino, and piperazinyl, and $R_{ii}$ is hydroxy.

Preferably, $R_2$ is pyrazolyl, in which the pyrazolyl is unsubstituted or substituted with $C_{1-4}$ alkyl, $SO_2$—$(C_{1-4}$ alkyl), or piperidinyl.

Preferably, $R_2$ is indolyl, pyrazinyl, pyrimidinyl, thiazolyl, or thienyl, in which the indolyl, pyrazinyl, pyrimidinyl, thiazolyl, or thienyl are unsubstituted.

Preferably, Ra is H, methoxy, or ethoxy.
Preferably, Rb is H or fluoro.
Preferably, Rc is H or methyl.

Representative examples of the compounds represented by Formula 1 are as follows:

1) 4-ethoxy-N-(3-fluoro-4-((5-(3-(hydroxymethyl)phenyl)pyrrolo[1,2-b]pyridazin-4-yl)oxy)phenyl)-1-(4-fluorophenyl)-2-oxo-1,2-dihydropyridin-3-carboxamide, 2) 4-ethoxy-N-(3-fluoro-4-((5-phenylpyrrolo[1,2-b]pyridazin-4-yl)-oxy)phenyl)-1-(4-fluorophenyl)2-oxo-1,2-dihydropyridin-3-carboxamide, 3) 4-ethoxy-N-(3-fluoro-4-((5-(pyridin-3-yl)pyrrolo[1,2-b]pyridazin-4-yl)oxy)phenyl)-1-(4-fluorophenyl)-2-oxo-1,2-dihydropyridin-3-carboxamide, 4) 4-ethoxy-N-(3-fluoro-4-((5-thiazol-2-yl)pyrrolo[1,2-b]pyridazin-4-yl)oxy)phenyl)-1-(4-fluorophenyl)-2-oxo-1,2-dihydropyridin-3-carboxamide, 5) 4-ethoxy-N-(2-fluoro-4-((pyrazin-2-yl)pyrrolo[1,2-b]pyridazin-4-yl)oxy)phenyl)-1-(4-fluorophenyl)-2-oxo-1,2-dihydropyridin-3-carboxamide, 6) 4-ethoxy-N-(2-fluoro-4-((5-(1-methyl-1H-pyrazol-4-yl)pyrrolo[1,2-b]pyridazin-4-yl)oxy)phenyl)-1-(4-fluorophenyl)-2-oxo-1,2-dihydropyridin-3-carboxamide, 7) 4-ethoxy-N-(3-fluoro-4-((5-pyridin-4-yl)pyrrolo[1,2-b]pyridazin-4-yl)oxy)phenyl)-1-(4-fluorophenyl)-2-oxo-1,2-dihydropyridin-3-carboxamide, 8) 4-ethoxy-N-(3-fluoro-4-((5-(pyrimidin-5-yl)pyrrolo[1,2-b]pyridazin-4-yl)oxy)phenyl)-1-(4-fluorophenyl)-2-oxo-1,2-dihydropyridin-3-carboxamide,
9) 4-ethoxy-N-(3-fluoro-4-((5-(6-methoxypyridin-3-yl)pyrrolo[1,2-b]pyridazin-4-yl)oxy)phenyl)-1-(4-fluorophenyl)-2-oxo-1,2-dihydropyridin-3-carboxamide,
10) 4-ethoxy-N-(3-fluoro-4-((5-(thiophen-3-yl)pyrrolo[1,2-b]pyridazin-4-yl)oxy)phenyl)-1-(4-fluorophenyl)-2-oxo-1,2-dihydropyridin-3-carboxamide,
11) 4-ethoxy-N-(3-fluoro-4-((5-(4-methoxyphenyl)pyrrolo[1,2-b]pyridazin-4-yl)oxy)phenyl)-1-(4-fluorophenyl)-2-oxo-1,2-dihydropyridin-3-carboxamide,
12) 4-ethoxy-N-(3-fluoro-4-((5-(2-fluorophenyl)pyrrolo[1,2-b]pyridazin-4-yl)oxy)phenyl)-1-(4-fluorophenyl)-2-oxo-1,2-dihydropyridin-3-carboxamide,
13) N-(4-((5-(3,4-dimethoxyphenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
14) 4-ethoxy-N-(3-fluoro-4-((5-(4-fluorophenyl)pyrrolo[1,2-b]pyridazin-4-yl)oxy)phenyl)-1-(4-fluorophenyl)-2-oxo-1,2-dihydropyridin-3-carboxamide,
15) 4-ethoxy-N-(3-fluoro-4-((5-(thiophen-2-yl)pyrrolo[1,2-b]pyridazin-4-yl)oxy)phenyl)-1-(4-fluorophenyl)-2-oxo-1,2-dihydropyridin-3-carboxamide,
16) N-(4-((5-(2-chloropyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
17) N-(4-((5-(1H-pyrazol-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
18) 4-ethoxy-N-(3-fluoro-4-((5-(1-methylsulfonyl)-1H-pyrazol-4-yl)pyrrolo[1,2-b]pyridazin-4-yl)oxy)phenyl)-1-(4-fluorophenyl)-2-oxo-1,2-dihydropyridin-3-carboxamide,
19) 4-ethoxy-N-(3-fluoro-4-((5-(2-fluoropyridin-4-yl)pyrrolo[1,2-b]pyridazin-4-yl)oxy)phenyl)-1-(4-fluorophenyl)-2-oxo-1,2-dihydropyridin-3-carboxamide,
20) N-(4-((5-(5-chloro-2-methoxypyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
21) N-(4-((5-(6-aminopyridin-3-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
22) 4-ethoxy-N-(3-fluoro-4-((5-(1-piperidin-4-yl)-1H-pyrazol-4-yl)pyrrolo[1,2-b]pyridazin-4-yl)oxy)phenyl)-1-(4-fluorophenyl)-2-oxo-1,2-dihydropyridin-3-carboxamide,
23) 4-ethoxy-N-(3-fluoro-4-((5-(3-formylphenyl)pyrrolo[1,2-b]pyridazin-4-yl)oxy)phenyl)-1-(4-fluorophenyl)-2-oxo-1,2-dihydropyridin-3-carboxamide,
24) 4-ethoxy-N-(3-fluoro-4-((5-(2-(piperazin-1-yl)pyridin-4-yl)pyrrolo[1,2-b]pyridazin-4-yl)oxy)phenyl)-1-(4-fluorophenyl)-2-oxo-1,2-dihydropyridin-3-carboxamide,
25) N-(4-((5-(6-acetamidopyridin-3-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
26) N-(4-((5-(2-acetylpyridin-4-yl)pyrrolo[1,2-b]pyridazin-4-yl)oxy)-3-fluorophenyl)-4-ethoxy-1-(4-fluorophenyl-2-oxo-1,2-dihydropyridin-3-carboxamide,
27) N-(4-((5-(3-acetylphenyl)pyrrolo[1,2-b]pyridazin-4-yl)oxy)-3-fluorophenyl)-4-ethoxy-1-(4-fluorophenyl-2-oxo-1,2-dihydropyridin-3-carboxamide,
28) N-(3-fluoro-4-((5-(pyridin-4-yl)pyrrolo[1,2-b]pyridazin-4-yl)oxy)phenyl)-4-methoxy-2-oxo-1-phenyl-1,2-dihydropyridin-3-carboxamide,
29) N-(3-fluoro-4-((5-(3-hydroxymethyl)phenyl)pyrrolo[1,2-b]pyridazin-4-yl)oxy)phenyl)-1-(4-fluorophenyl)-2-oxo-1,2-dihydropyridin-3-carboxamide,
30) 4-ethoxy-N-(4-((5-(3-(ethylsulfonyl)phenyl)pyrrolo[1,2-b]pyridazin-4-yl)oxy)-3-fluorophenyl)-1-(4-fluorophenyl)-2-oxo-1,2-dihydropyridin-3-carboxamide,
31) 4-ethoxy-N-(3-fluoro-4-((5-(3-(methylsulfonyl)phenyl)pyrrolo[1,2-b]pyridazin-4-yl)oxy)phenyl)-1-(4-fluorophenyl)-2-oxo-1,2-dihydropyridin-3-carboxamide,
32) 4-ethoxy-N-(3-fluoro-4-((5-(3-sulfamoylphenyl)pyrrolo[1,2-b]pyridazin-4-yl)oxy)phenyl)-1-(4-fluorophenyl)-2-oxo-1,2-dihydropyridin-3-carboxamide,
33) N-(4-((5-(3-acetylphenyl)pyrrolo[1,2-b]pyridazin-4-yl)oxy)-3-fluorophenyl)-4-ethoxy-1-(4-fluorophenyl-2-oxo-1,2-dihydropyridin-3-carboxamide,
34) N-(3-fluoro-4-((5-(pyridin-4-yl)pyrrolo[1,2-b]pyridazin-4-yl)oxy)phenyl)-4-methoxy-2-oxo-1-phenyl-1,2-dihydropyridin-3-carboxamide,
35) N-(4-((5-(3-(N-methylsulfamoylphenyl))pyrrolo[1,2-b]pyridazin-4-yl)oxy)-3-fluorophenyl)-4-ethoxy-1-(4-fluorophenyl)-2-oxo-1,2-dihydropyridin-3-carboxamide,
36) N-(4-((5-(3-(N,N-dimethyl sulfamoyl)phenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
37) 4-ethoxy-N-(3-fluoro-4-((5-(4-nitrophenyl)pyrrolo[1,2-b]pyridazin-4-yl)oxy)phenyl)-1-(4-fluorophenyl)-2-oxo-1,2-dihydropyridin-3-carboxamide,
38) N-(4-((5-(4-aminophenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
39) 4-ethoxy-N-(3-fluoro-4-((5-(3-((2-methoxyethoxy)methyl)phenyl)pyrrolo[1,2-b]pyridazin-4-yl)oxy)phenyl)-1-(4-fluorophenyl)-2-oxo-1,2-dihydropyridin-3-carboxamide,
40) N-(3-fluoro-4-((5-(2-methoxypyridin-4-yl)pyrrolo[1,2-b]pyridazin-4-yl)oxy)phenyl)-1-(4-fluorophenyl)-2-oxo-1,2-dihydropyridin-3-carboxamide, 41) N-(4-((5-(3-(dimethylcarbamoyl)phenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide, 42) N-(3-fluoro-4-((5-(pyridin-4-yl)pyrrolo[1,2-b]pyridazin-4-yl)oxy)phenyl)-N-(4-fluorophenyl)cyclopropane-1,1-dicarboxyamide, 43) 4-ethoxy-N-(3-fluoro-4-((5-(3-(2-hydroxypropan-2-yl)phenyl)pyrrolo[1,2-b]pyridazin-4-yl)oxy)phenyl)-1-(4-fluorophenyl)-2-oxo-1,2-dihydropyridin-3-carboxamide, 44) 4-ethoxy-N-(3-fluoro-4-((5-(3-(methylcarbamoyl)phenyl)pyrrolo[1,2-b]pyridazin-4-yl)oxy)phenyl)-1-(4-fluorophenyl)-2-oxo-1,2-dihydropyridin-3-carboxamide, 45) 3-(4-(4-(4-ethoxy-1-(4-fluorophenyl)-2-oxo-1,2-dihydropyridin-3-carboxamido)-2-fluorophenoxy)pyrrolo[1,2-b]pyridazin-5-yl)benzyl carbamate, 46) 4-ethoxy-N-(3-fluoro-4-((5-(3-(1-hydroxyethyl)phenyl)pyrrolo[1,2-b]pyridazin-4-yl)oxy)phenyl)-1-(4-fluorophenyl)-2-oxo-1,2-dihydropyridin-3-carboxamide, 47) N-(3-fluoro-4-((5-(3-(1-hydroxyethyl)phenyl)pyrrolo[1,2-b]pyridazin-4-yl)oxy)phenyl)-1-(4-fluorophenyl)-2-oxo-1,2-dihydropyridin-3-carboxamide, 48) N-(3-fluoro-4-((5-(3-(1-hydroxyethyl)phenyl)pyrrolo[1,2-b]pyridazin-4-yl)oxy)phenyl)-4-methoxy-2-oxo-1-phenyl-1,2-dihydropyridin-3-carboxamide, 49) 4-ethoxy-N-(3-fluoro-4-((5-(pyrimidin-5-yl)pyrrolo[1,2-b]pyridazin-4-yl)oxy)phenyl)-1-(4-fluorophenyl)-2-oxo-1,2-dihydropyridin-3-carboxamide, 50) 4-ethoxy-N-(3-fluoro-4-((5-(3-morpholin-4-carbonyl)phenyl)pyrrolo[1,2-b]pyridazin-4-yl)oxy)phenyl)-1-(4-fluorophenyl)-2-oxo-1,2-dihydropyridin-3-carboxamide, 51) 4-ethoxy-N-(3-fluoro-4-((5-(2-morpholidinpyridin-4-yl)pyrrolo[1,2-b]pyridazin-4-yl]oxy)phenyl)-1-(4-fluorophenyl)-2-oxo-1,2-dihydropyridin-3-carboxamide, 52) 4-ethoxy-N-(3-fluoro-4-((5-(3-nitrophenyl)pyrrolo[1,2-b]pyridazin-4-yl)oxy)phenyl)-1-(4-fluorophenyl)-2-oxo-1,2-dihydropyridin-3-carboxamide, 53) 4-ethoxy-N-(3-fluoro-4-((5-(3-aminophenyl)pyrrolo[1,2-b]pyridazin-4-yl)oxy)phenyl)-1-(4-fluorophenyl)-2-oxo-1,2-dihydropyridin-3-carboxamide, 54) 4-ethoxy-N-(3-fluoro-4-((5-(3-(1-methoxyethyl)phenyl)pyrrolo[1,2-b]pyridazin-4-yl)oxy)phenyl)-1-(4-fluorophenyl)-2-oxo-1,2-dihydropyridin-3-carboxamide, 55) N-(3-fluoro-4-((5-(3-(1-hydroxyethyl)phenyl)pyrrolo[1,2-b]pyridazin-4-yl)oxy)phenyl)-N-(4-fluorophenyl)cyclopropane-1,1-dicarboxamide, 56) N-(4-((5-(3-((dimethylamino)methyl)phenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide, 57) N-(3-fluoro-4-((5-(pyridin-4-yl)pyrrolo[1,2-b]pyridazin-4-yl)oxy)-phenyl)-1-(4-fluorophenyl)-2-oxo-1,2-dihydropyridin-3-carboxamide, 58) 4-ethoxy-N-(4-((5-(2-ethoxypyridin-4-yl)pyrrolo[1,2-b]pyridazin-4-yl)-oxy)-3-fluorophenyl)-1-(4-fluorophenyl)-2-oxo-1,2-dihydropyridin-3-carboxamide, 59) 4-ethoxy-N-(3-fluoro-4-((5-(2-methoxypyridin-4-yl)pyrrolo[1,2-b]pyridazin-4-yl)oxy)phenyl)-1-(4-fluorophenyl)-2-oxo-1,2-dihydropyridin-3-carboxamide, 60) N-(3-fluoro-4-((5-(pyridin-4-yl)pyrrolo[1,2-b]pyridazin-4-yl)oxy)phenyl)-4-ethoxy-2-oxo-1-phenyl-1,2-dihydropyridin-3-carboxamide, 61) N-(4-((5-(2,6-dimethylpyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide, 62) N-(4-((5-(2-(1-hydroxyethyl)pyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide, 63) N-(4-((5-(3-((dimethylamino)methyl)phenyl)pyrrolo[1,2-b]pyridazin-4-yl)oxy)-3-fluorophenyl)-N-(4-fluorophenyl)cyclopropane-1,1-dicarboxamide, 64) N-(4-((5-(3-aminophenyl)pyrrolo[1,2-b]pyridazin-4-yl)oxy)-3-fluorophenyl)-N-(4-fluorophenyl)cyclopropane-1,1-dicarboxamide, 65) N-(4-((5-(3-acetamidophenyl)pyrrolo[1,2-b]pyridazin-4-yl)oxy)-3-fluorophenyl)-N-(4-fluorophenyl)cyclopropane-1,1-dicarboxamide, 66) N-(4-((5-(3-amino-4-fluorophenyl)pyrrolo[1,2-b]pyridazin-4-yl)oxy)-3-fluorophenyl)-N-(4-fluorophenyl)cyclopropane-1,1-dicarboxamide, 67) N-(4-((5-(3-amino-5-cyanophenyl)pyrrolo[1,2-b]pyridazin-4-yl)oxy)-3-fluorophenyl)-N-(4-fluorophenyl)cyclopropane-1,1-dicarboxamide, 68) N-(4-((5-(3-((dimethylamino)methyl)phenyl)pyrrolo[1,2-bpyridazin-4-yl]oxy)-3-fluorophenyl)-1-(4-fluorophenyl)-6-methyl-2-oxo-1,2-dihydropyridin-3-carboxamide, 69) N-(4-((5-(3-carbamoylphenyl)pyrrolo[1,2-b]pyridazin-4-yl)oxy)-3-fluorophenyl)-N-(4-fluorophenyl)cyclopropane-1,1-dicarboxamide, 70) N-(4-((5-(3-aminomethylphenyl)pyrrolo[1,2-b]pyridazin-4-yl)oxy)-3-fluorophenyl)-N-(4-fluorophenyl)cyclopropane-1,1-dicarboxamide, 71) N-(4-((5-(3-hydroxymethylphenyl)pyrrolo[1,2-b]pyridazin-4-yl)oxy)-3-fluorophenyl)-N-(4-fluorophenyl)cyclopropane-1,1-dicarboxamide, 72) N-(4-((5-(3-(methylamino)phenyl)pyrrolo[1,2-b]pyridazin-4-yl)oxy)-3-fluorophenyl)-N-(4-fluorophenyl)cyclopropane-1,1-dicarboxamide, 73) N-(4-((5-(3-(ethylamino)phenyl)pyrrolo[1,2-b]pyridazin-4-yl)oxy)-3-fluorophenyl)-N-(4-fluorophenyl)cyclopropane-1,1-dicarboxamide, 74) N-(4-((5-(1H-indol-6-yl)pyrrolo[1,2-b]pyridazin-4-yl)oxy)-3-fluorophenyl)-N-(4-fluorophenyl)cyclopropane-1,1-dicarboxamide, 75) N-(4-((5-(2-chloro-5-((dimethylamino)methyl)phenyl)pyrrolo[1,2-b]pyridazin-4-yl)oxy)-3-fluorophenyl)-N-(4-fluorophenyl)cyclopropane-1,1-dicarboxamide, 76) N-(4-((5-(5-((dimethylamino)methyl)-2-fluorophenyl)pyrrolo[1,2-b]pyridazin-4-yl)oxy)-3-fluorophenyl)-N-(4-fluorophenyl)cyclopropane-1,1-dicarboxamide, 77) N-(4-((5-(3-((dimethylamino)methyl)-5-fluorophenyl)pyrrolo[1,2-b]pyridazin-4-yl)oxy)-3-fluorophenyl)-N-(4-fluorophenyl)cyclopropane-1,1-dicarboxamide, 78) N-(4-((5-(3-amino-4-methyl)-5-fluorophenyl)pyrrolo[1,2-b]pyridazin-4-yl)oxy)-3-fluorophenyl)-N-(4-fluorophenyl)cyclopropane-1,1-dicarboxamide, 79) N-(4-((5-(3-amino-2-methyl)-5-fluorophenyl)pyrrolo[1,2-b]pyridazin-4-yl)oxy)-3-fluorophenyl)-N-(4-fluorophenyl)cyclopropane-1,1-dicarboxamide, 80) N-(3-fluoro-4-((5-(3-((methylamino)methyl)phenyl)pyrrolo[1,2-b]pyridazin-4-yl)oxy)phenyl)-N-(4-fluorophenyl)cyclopropane-1,1-dicarboxamide, 81) N-(4-((5-(3-((ethylamino)methyl)phenyl)pyrrolo[1,2-b]pyridazin-4-yl)oxy)-3-fluorophenyl)-N-(4-fluorophenyl)cyclopropane-1,1-dicarboxamide, 82) N-(4-((5-(3-amino-4-methoxy)-5-fluorophenyl)pyrrolo[1,2-b]pyridazin-4-yl)oxy)-3-fluorophenyl)-N-(4-fluorophenyl)cyclopropane-1,1-dicarboxamide, 83) N-(4-((5-(5-amino-2-fluoro)-5-fluorophenyl)pyrrolo[1,2-b]pyridazin-4-yl)oxy)-3-fluorophenyl)-N-(4-fluorophenyl)cyclopropane-1,1-dicarboxamide, 84) N-(4-((5-(3-(methylcarbamoyl)phenyl)pyrrolo[1,2-b]pyridazin-4-yl)oxy)-3-fluorophenyl)-N-(4-fluorophenyl)cyclopropane-1,1-dicarboxamide, 85) N-(4-((5-(3-cyanomethylphenyl)pyrrolo[1,2-b]pyridazin-4-yl)oxy)-3-fluorophenyl)-N-(4-fluorophenyl)cyclopropane-1,1-dicarboxamide, and 86) N-(4-((5-3-aminophenyl)pyrrolo[1,2-b]pyridazin-4-yl)oxy)-3-fluorophenyl)-1-(4-fluorophenyl)-6-methyl-2-oxo-1,2-dihydropyridin-3-carboxamide.

Additionally, the compounds represented by Formula 1 may form a pharmaceutically acceptable salt. Examples of the pharmaceutically acceptable salt may include acid addition salts formed by acid which can form non-toxic acid addition salts containing pharmaceutically acceptable anions, for example, inorganic acids such as hydrochloric acid, sulfuric acid, nitric acid, phosphoric acid, hydrobromic acid, and hydriodic acid; organic carbonic acids such as tartaric acid, formic acid, citric acid, acetic acid, adipic acid, trichloroacetic acid, trifluoroacetic acid, gluconic acid, benzoic acid, lactic acid, fumaric acid, and maleic acid; and sulfonic acids such as methanesulfonic acid, benzenesulfonic acid, p-toluenesulfonic acid, and naphthalenesulfonic acid. The compounds of Formula 1 according to the present invention may be converted into the salts thereof by conventional methods.

Additionally, the compounds according to the present invention can have asymmetric carbon centers and thus can be present as R or S isomers, racemates, mixtures of diastereomers, and individual diastereomers, and all these isomers and mixtures belong to the scope of the present invention.

Additionally, the present invention also provides a method for preparing the compound represented by the following Formula 1 indicated in Reaction Scheme 1 below:

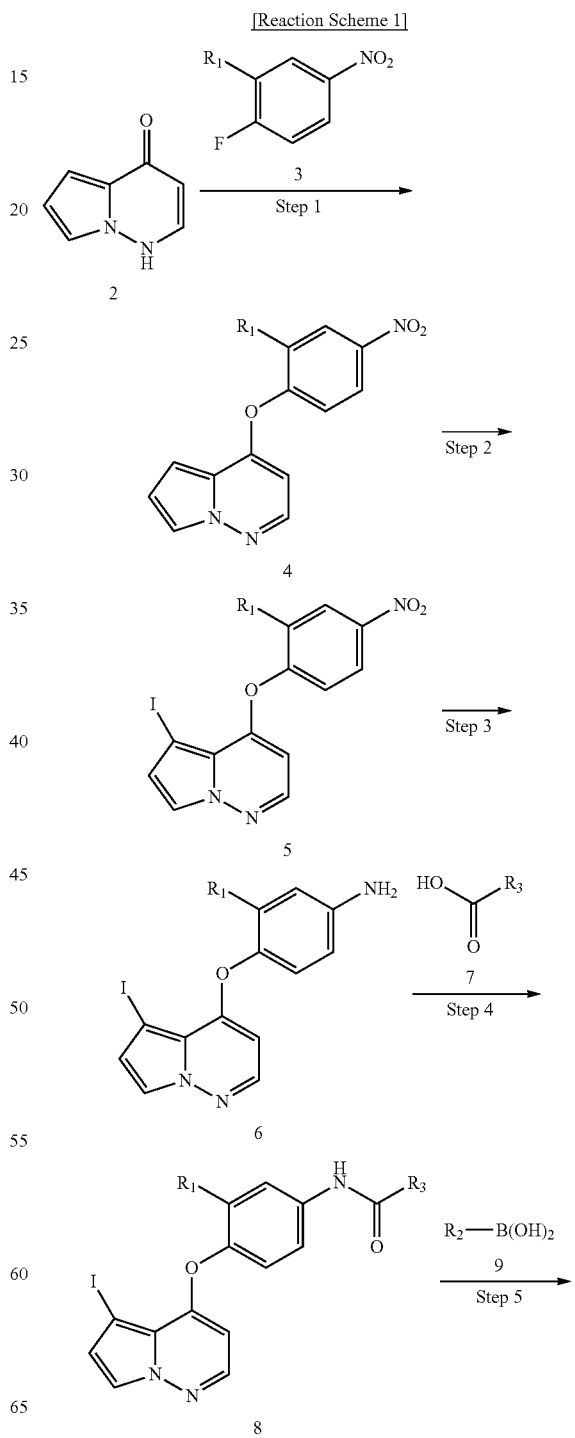

-continued

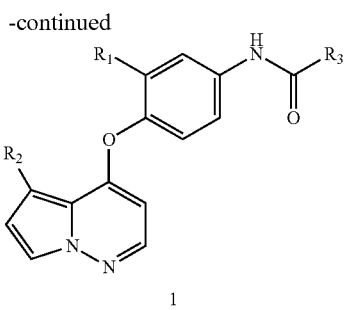

In the Reaction Scheme 1, $R_1$, $R_2$, and $R_3$ are the same as defined above. The details of Reaction Scheme 1 are as follows.

Step 1 is preparing a compound represented by Formula 4 by reacting a compound represented by Formula 2 with a compound represented by Formula 3. Step 1 is preferably performed in the presence of $Cs_2CO_3$, and DMF is preferably used as a solvent.

Step 2 is preparing a compound represented by Formula 5 by reacting a compound represented by Formula 4 with N-Iodosuccinimide (NIS). Preferably, $CHCl_3$ is used as a solvent.

Step 3 is preparing a compound represented by Formula 6 by reacting a compound represented by Formula 5 with $NH_4Cl$. Step 3 is preferably performed in the presence of Fe, and ethanol/water is preferably used as a solvent.

Step 4 is preparing a compound represented by Formula 8 by reacting a compound represented by Formula 6 with a compound represented by Formula 7. Step 4 is preferably performed in the presence of $Et_3N$ and $SOCl_2$, and $CH_2Cl_2$ is preferably used as a solvent.

Step 5 is preparing a compound represented by Formula 1 by reacting a compound represented by Formula 8 with a compound represented by Formula 9. Step 5 is preferably performed in the presence of $Pd(PPh_3)_4$ and $K_2CO_3$, and dioxane is preferably used as a solvent.

Additionally, the present invention provides a pharmaceutical composition for preventing or treating protein kinase-related diseases containing the compound represented by Formula 1 or a pharmaceutically acceptable salt thereof as an active ingredient.

As used herein, the term "protein kinase-related diseases" refers to those diseases that can be prevented or treated by inhibiting the activity of protein kinase, and in particular, cancer, psoriasis, rheumatoid arthritis, inflammatory bowel disease, or chronic obstructive pulmonary disease.

As used herein, the term "prevention" refers to all actions resulting in suppression or delay of the above diseases by the administration of the pharmaceutical composition. Additionally, as used herein, the term "treatment" refers to all actions resulting in improvement or complete elimination of symptoms of the above diseases by the administration of the pharmaceutical composition.

The pharmaceutical composition may further include a pharmaceutically acceptable carrier, diluent, or excipient. As used herein, the term "pharmaceutically acceptable carrier" refers to a carrier or diluent which neither causes significant stimulation to an organism nor abolishes the biological activities or properties of a compound to be administered thereto. Additionally, as used herein, the term "pharmaceutically acceptable excipient" refers to an inert material which is added to a composition to facilitate the administration of the compound represented by Formula 1 of the present invention. Examples of the excipient may include calcium carbonate, calcium phosphate, various types of sugar and starch, cellulose derivatives, gelatin, vegetable oil, and polyethylene glycol, but are not limited thereto.

The pharmaceutical composition of the present invention may be administered orally or parenterally (e.g., intravenously, subcutaneously, intraperitoneally, or topically) according to the intended purposes. The administration dose may vary depending on the health conditions and body weight of a patient, severity of disease, drug types, routes and time of administration, but it may be appropriately selected by one of ordinary skill in the art. Preferably, the effective daily dose of the compound represented by Formula 1 or a pharmaceutically acceptable salt thereof may be from 1 mg/kg to 500 mg/kg, and the administration may be performed once or in a few divided doses daily as necessary.

Advantageous Effects of the Invention

The compounds according to the present invention and pharmaceutically acceptable salts thereof can be effectively used for the prevention or treatment of protein kinase-related diseases by inhibiting the activity of protein kinase(s).

DETAILED DESCRIPTION OF THE INVENTION

Hereinafter, the present invention will be described in more detail with reference to the following Examples. However, these Examples are for illustrative purposes only, and the invention is not intended to be limited by these Examples.

Various methods for synthesizing starting materials for the synthesis of the compounds of the present invention are known, and when the starting materials may be purchased for use when they are commercially available. Examples of the reagents suppliers may include Sigma-Aldrich, TCI, Wako, Kanto, Fluorchem, Acros, Alfa, Fluka, Dae-Jung, etc., but are not limited thereto. Additionally, all the commercially available materials were used without further purification unless specified otherwise.

First, the compounds to be used in the synthesis in the following Examples were prepared as shown in Preparation Examples below. The Preparation Examples below are examples of the compounds represented by Formula 7 of Reaction Scheme 1 shown above, and may be appropriately altered according to the structures of the examples to be prepared.

PREPARATION EXAMPLE 1

Preparation of 4-ethoxy-1-(4-fluorophenyl)-2-oxo-1,2-dihydropyridin-3-carboxylic acid Step 1) Preparation of ethyl 4-ethoxy-2-oxo-1,2-dihydropyridin-3-carboxylate

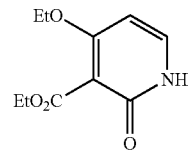

Ethyl cyanoacetate (70.5 mL, 0.66 mol) was added with triethyl orthoacetate (249.6 mL, 1.32 mmol) and acetic acid (19.6 mL, 0.33 mol) and stirred at 120° C. for at least 12 hours. The solvent of the reaction mixture was concentrated and added with N,N-dimethylformamide diethylacetal (DMF-DEA) (141 mL, 0.55 mol) and stirred at 70° C. for at least 2 hours. The reaction mixture was added with acetic acid (500 mL) and distilled water (60 mL) and refluxed for at least 12 hours. The reaction mixture was cooled to room temperature and added with a saturated aqueous solution of sodium hydrogen carbonate and water. The resultant was extracted using a mixed solvent (dichloromethane:methanol=9:1). The resulting organic layer was dried over anhydrous magnesium sulfate, filtered, and concentrated under reduced pressure. The resultant was added with ethyl acetate (100 mL) and concentrated. The thus-obtained solid was filtered to obtain 37 g (26%) of ethyl 4-ethoxy-2-oxo-1,2-dihydropyridin-3-carboxylate.

$^1$H NMR (400 MHz, DMSO-$d_6$) δ 11.61 (bs, 1H), 7.46 (d, J=7.6 Hz, 1H), 6.21 (d, J=7.6 Hz, 1H), 4.++14 (m, 4H), 1.22 (m, 6H)

MS: 212 [M+H]$^+$

Step 2) Preparation of ethyl 4-ethoxy-1-(4-fluorophenyl)-2-oxo-1,2-dihydropyridin-3-carboxylate

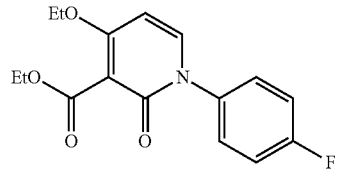 [SMILES: CCOC(=O)c1c(OCC)ccn(-c2ccc(F)cc2)c1=O]

Cesium carbonate (114 g, 0.35 mol) was added with N,N-dimethylformamide (100 mL) and filled with a nitrogen gas. The mixture was stirred at room temperature for 10 minutes, added with of 8-hydroxyquinolinol (10.2 g, 0.07 mol) after dissolving it in N,N-dimethylformamide (200 mL), and then added with copper iodide (10 g, 0.05 mol), 4-fluoroiodobenzene (58.3 g, 0.26 mol), and the compound obtained in Step 1 (37 g, 0.17 mol). The resultant was stirred at 110° C. for 24 hours. Upon completion of the reaction, the resultant was cooled to room temperature, added with ethyl acetate, and stirred for 10 minutes. The reaction mixture was filtered with a Celite pad, and the resulting filtrate was extracted using water and ethyl acetate. The resulting organic layer was dried over anhydrous magnesium sulfate and filtered, and the solvent was removed under reduced pressure. The resultant was used in Step 3 below without further purification.

Step 3) Preparation of 4-ethoxy-1-(4-fluorophenyl)-2-oxo-1,2-dihydropyridin-3-carboxylic acid

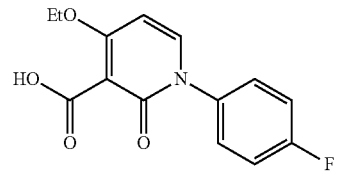 [SMILES: CCOc1ccn(-c2ccc(F)cc2)c(=O)c1C(=O)O]

The compound of Step 2 was dissolved in ethanol (200 mL) and added with 3N hydrogen chloride solution (400 mL). The mixture was stirred at 60° C. for 24 hours. The resulting solid was filtered to obtain 21 g (yield in Step 2: 43%) of 4-ethoxy-1-(4-fluorophenyl)-2-oxo-1,2-dihydropyridin-3-carboxylic acid.

$^1$H NMR (400 MHz, DMSO-$d_6$) δ 7.95 (d, J=7.6 Hz, 1H), 7.48 (m, 2H), 7.35 (m, 2H), 6.58 (d, J=8 Hz, 1H), 4.28 (q, J=6.8 Hz, 2H), 1.32 (t, J=6.8 Hz, 3H)

MS: 276 [M+H]$^-$

PREPARATION EXAMPLE 2

Preparation of 4-ethoxy-2-oxo-1-phenyl-1,2-dihydropyridin-3-carboxylic acid

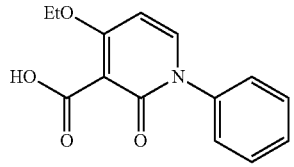 [SMILES: CCOc1ccn(-c2ccccc2)c(=O)c1C(=O)O]

The target compound was prepared in the same manner as in Preparation Example 1 except that iodobenzene was used instead of 4-fluoroiodobenzene in Step 2 of Preparation Example 1.

$^1$H NMR (400 MHz, DMSO-$d_6$) δ 7.98 (d, J=8 Hz, 1H), 7.56-7.41 (m, 5H), 6.60 (d, J=7.6 Hz, 1H), 4.30 (q, J=7.2 Hz, 2H), 1.34 (t, J=7.2 Hz, 3H)

MS: 260 [M+H]$^+$

PREPARATION EXAMPLE 3

Preparation of 1-(4-fluorophenyl)-4-methoxy-2-oxo-1,2-dihydropyridin-3-carboxylic acid Step 1) Preparation of methyl 4-methoxy-1-(4-fluorophenyl)-2-oxo-1,2-dihydropyridin-3-carboxylate

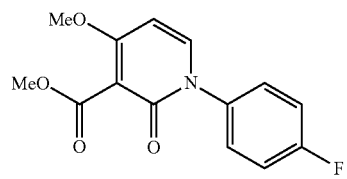 [SMILES: COC(=O)c1c(OC)ccn(-c2ccc(F)cc2)c1=O]

Ethyl 4-ethoxy-1-(4-fluorophenyl)-2-oxo-1,2-dihydropyridin-3-carboxylate (0.37 g, 1.20 mmol) was treated with 28% NaOMe solution and stirred at room temperature for 10 minutes. The solvent was removed by concentrating under reduced pressure to obtain 0.26 g (yield: 77%) of the target compound.

Step 2) Preparation of 4-methoxy-1-(4-fluorophenyl)-2-oxo-1,2-dihydropyridin-3-carboxylic acid

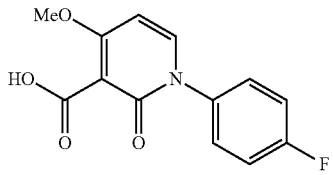 [SMILES: COc1ccn(-c2ccc(F)cc2)c(=O)c1C(=O)O]

Methyl 4-methoxy-1-(4-fluorophenyl)-2-oxo-1,2-dihydropyridin-3-carboxylate (0.33 g, 1.18 mmol) prepared in Step 1 was treated with ethanol (5 mL) and dropwise added with 2.75 N hydrogen chloride solution (10 mL) at room temperature. The mixture was stirred at 60° C. for 4 hours and the resulting solid was filtered to obtain 0.16 g (52%) of the target compound.

$^1$H NMR (400 MHz, DMSO-$d_6$) δ 13.89 (bs, 1H), 8.02 (d, J=7.6 Hz, 1H), 7.53-7.48 (m, 2H), 7.40-7.34 (m, 2H), 6.63 (d, J=8 Hz, 1H), 4.02 (s, 3H)

MS: 264 [M+H]$^+$

PREPARATION EXAMPLE 4

Preparation of 4-methoxy-2-oxo-1-phenyl-1,2-dihydropyridin-3-carboxylic acid

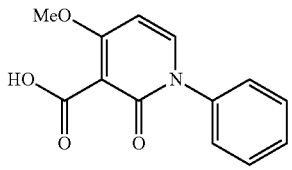 [SMILES: COc1ccn(-c2ccccc2)c(=O)c1C(=O)O]

The target compound was prepared in the same manner as in Preparation Example 2 except that ethyl 4-ethoxy-1-phenyl-2-oxo-1,2-dihydropyridin-3-carboxylate, which was used in Preparation Example 2, was used instead of ethyl 4-ethoxy-1-(4-fluorophenyl)-2-oxo-1,2-dihydropyridin-3-carboxylate in Step 1 of Preparation Example 2.

$^1$H NMR (400 MHz, DMSO-$d_6$) δ 7.96 (d, J=7.8 Hz, 1H), 7.55-7.45 (m, 5H), 6.58 (d, J=7.8 Hz, 1H), 3.99 (s, 3H)

MS: 246 [M+H]$^+$

PREPARATION EXAMPLE 5

Preparation of 1-(4-fluorophenyl)-2-oxo-1,2-dihydropyridin-3-carboxylic acid

Step 1) Preparation of methyl 1-(4-fluorophenyl)-2-oxo-1,2-dihydropyridin-3-carboxylate

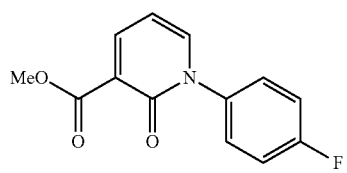 [SMILES: COC(=O)c1cccn(-c2ccc(F)cc2)c1=O]

Methyl 2-oxo-2H-pyran-3-carboxylate (5 g, 32.4 mmol) was dissolved in tetrahydrofuran (100 mL), added with 4-fluoroaniline (3.6 g, 32.4 mmol), and stirred at room temperature for 3 hours. The resultant was added with 1-(3-dimethylaminopropyl)-3-ethylcarbodiimide hydrochloride (8.1 g, 42.2 mmol) and 4-(dimethylamino)pyridine (0.4 g, 3.2 mmol), and stirred at room temperature for 16 hours. The resultant was added with ethyl acetate and water, and was added with 10% hydrogen chloride solution to extract. Then the resulting organic layer was separated and dried over anhydrous magnesium sulfate, and concentrated under reduced pressure to obtain the residue. The residue was purified by silica gel column chromatography (20% ethyl acetate in n-hexane) to obtain 1.8 g (22%) of methyl 1-(4-fluorophenyl)-2-oxo-1,2-dihydropyridin-3-carboxylate in ivory solid.

$^1$H NMR (400 MHz, DMSO-$d_6$) δ 8.12 (dd, J=6.8 and 2.0 Hz, 1H), 7.95 (dd, J=6.8 and 2.0 Hz, 1H), 7.50 (d, J=4.8 Hz, 1H), 7.48 (J=5.2 Hz, 1H), 7.36 (t, J=8.8 Hz, 2H), 6.41 (t, J=6.8 Hz, 2H), 3.75 (s, 1H)

MS: 248 [M+H]$^+$

Step 2) Preparation of 1-(4-fluorophenyl)-2-oxo-1,2-dihydropyridin-3-carboxylic acid

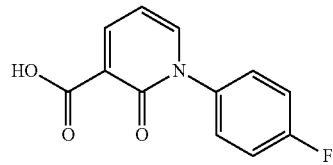 [SMILES: O=C(O)c1cccn(-c2ccc(F)cc2)c1=O]

Methyl 1-(4-fluorophenyl)-2-oxo-1,2-dihydropyridin-3-carboxylate (1.8 g, 7.29 mmol) prepared in Step 1 was dissolved in methanol (25 mL), added with 1 N NaOH solution (11 mL), and stirred at room temperature for 15 hours. The reaction mixture was concentrated under reduced pressure, acidified with 1 N hydrogen chloride solution, and filtered to obtain 1.6 g (94%) of 1-(4-fluorophenyl)-2-oxo-1,2-dihydropyridin-3-carboxylic acid in white solid.

$^1$H NMR (400 MHz, DMSO-$d_6$) δ 14.23 (s, 1H), 8.49 (dd, J=6.8 and 2.0 Hz), 8.21 (dd, J=6.8 and 2.0 Hz), 7.63 (d, J=4.8 Hz, 1H), 7.61 (J=5.2 Hz, 1H), 7.42 (t, J=8.8 Hz, 2H), 6.79 (t, J=7.2 Hz, 2H)

MS: 234 [M+H]$^+$

EXAMPLE 1

Preparation of 4-ethoxy-N-(3-fluoro-4-((5-(3-(hydroxymethyl)phenyl)pyrrolo[1,2-b]pyridazin-4-yl)oxy)phenyl)-1-(4-fluorophenyl)-2-oxo-1,2-dihydropyridin-3-carboxamide Step 1) Preparation of 4-(2-fluoro-4-nitrophenoxy)pyrrolo[1,2-b]pyridazine

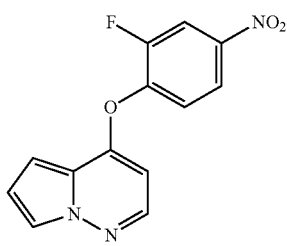 [SMILES: O=[N+]([O-])c1ccc(Oc2ccnn3cccc23)c(F)c1]

Pyrrolo[1,2-b]pyridazin-4-ol (3.7 g, 27.6 mmol) was dissolved in dimethylformamide (37 mL), added with cesium carbonate (18.0 g, 55.2 mmol) and 1,2-difluoro-4-nitrobenzene (4.83 g, 30.3 mmol), and stirred at from 30° C. to 40° C. for 4 hours. Upon completion of the reaction, the mixture was added with HCl to adjust the pH to 3 to 4, extracted with ethyl acetate, dried over anhydrous magnesium sulfate, and concentrated under reduced pressure to obtain the residue. The residue was suspended in isopropyl ether and filtered to obtain 6.7 g (89%) of 4-(2-fluoro-4-nitrophenoxy)pyrrolo[1,2-b]pyridazine.

$^1$H NMR (400 MHz, CDCl$_3$) δ 8.16-8.11 (m, 2H), 7.91 (d, J=5.2 Hz, 1H), 7.82-7.81 (m, 1H), 7.41-7.35 (m, 1H), 6.86-6.84 (m, 1H), 6.67-6.32 (m, 1H), 5.84 (t, J=4.8 Hz, 1H)

Step 2) Preparation of 4-(2-fluoro-4-nitrophenoxy)-5-iodopyrrolo[1,2-b]pyridazine

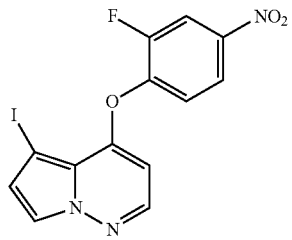 [SMILES: O=[N+]([O-])c1ccc(Oc2ccnn3ccc(I)c23)c(F)c1]

4-(2-Fluoro-4-nitrophenoxy)pyrrolo[1,2-b]pyridazine (2.0 g, 7.32 mmol) prepared in Step 1 was dissolved in chloroform (40 mL) and cooled to 0° C. The resultant was added with N-iodosuccinimide (1.81 g, 8.05 mmol) and stirred at room temperature for 3 hours. Upon completion of the reaction, the mixture was washed by adding water thereto, extracted with ethyl acetate, dried over anhydrous magnesium sulfate, and concentrated under reduced pressure to obtain the residue. The residue was purified by silica gel column chromatography (10% ethyl acetate in n-hexane) to obtain 910 mg (31%) of 4-(2-fluoro-4-nitrophenoxy)-5-iodopyrrolo[1,2-b]pyridazine.

$^1$H NMR (400 MHz, CDCl$_3$) δ 8.20-8.12 (m, 2H), 7.91 (d, J=5.6 Hz, 1H), 7.75 (d, J=2.8 Hz, 1H), 7.38-7.34 (m, 1H), 6.98 (d, J=2.8 Hz, 1H), 5.85-5.84 (m, 1H)

Step 3) Preparation of 3-fluoro-4-((5-iodopyrrolo[1,2-b]pyridazin-4-yl)oxy)aniline

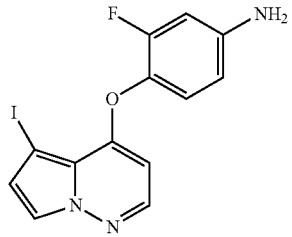 [SMILES: Nc1ccc(Oc2ccnn3ccc(I)c23)c(F)c1]

4-(2-Fluoro-4-nitrophenoxy)-5-iodopyrrolo[1,2-b]pyridazine (2.7 g, 6.76 mmol) prepared in Step 2 was dissolved in a solution (methanol/distilled water=2/1), added with Fe (1.13 g, 20.3 mmol) and ammonium chloride (3.62 g, 67.6 mmol), and stirred at 100° C. for 1.5 hours. Upon completion of the reaction, the mixture was cooled to room temperature, added with ethyl acetate and stirred for 2 hours, filtered with a Celite pad, and the filtrate was obtained. The filtrate was washed with water, extracted with ethyl acetate, dried over anhydrous magnesium sulfate, and concentrated under reduced pressure to obtain the residue. The residue was suspended in isopropyl ether and filtered to obtain 2.2 g (88%) of 3-fluoro-4-((5-iodopyrrolo[1,2-b]pyridazin-4-yl)oxy)aniline.

$^1$H NMR (400 MHz, DMSO-d$_6$) δ 7.99 (d, J=5.6 Hz, 1H), 7.90 (d, J=3.2 Hz, 1H), 7.08 (t, J=9.2 Hz, 1H), 6.92 (d, J=2.8 Hz, 1H), 6.56-6.52 (m, 1H), 6.46-6.44 (m, 1H), 5.75 (d, J=5.2 Hz, 1H), 5.53 (s, 2H)

Step 4) Preparation of 4-ethoxy-N-(3-fluoro-4-((5-iodopyrrolo[1,2-b]pyridazin-4-yl)oxy)phenyl)-1-(4-fluorophenyl)-2-oxo-1,2-dihydropyridin-3-carboxamide

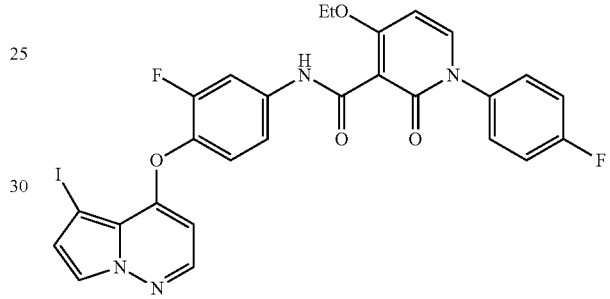

1-(4-Fluorophenyl)-2-oxo-1,2-dihydropyridin-3-carboxylic acid (3.94 g, 0.014 mol) and dichloromethane (50 mL) were added together and stirred. The mixture was added with SOCl$_2$ (2.81 g, 0.024 mol) and DMF (2 to 3 drops), and stirred at room temperature for 1 hour. Upon complete dissolution, the mixture was concentrated under reduced pressure (reaction container A).

3-Fluoro-4-((5-iodopyrrolo[1,2-b]pyridazin-4-yl)oxy)aniline (4.37 g, 0.012 mol), which was prepared in Step 3, dichloromethane (50 mL), and triethylamine (4.96 mL, 0.036 mol) were added together to another reaction container and mixed for 0.5 hour (reaction container B).

Dichloromethane (50 mL) was added to the concentrated mixture in the reaction container A, stirred, and the mixture was dropwise added to the reaction container B. The resultant was stirred at room temperature for 12 hours and adjusted to a neutral state by adding water and 1 N HCl thereto.

The reaction mixture was extracted with dichloromethane, dried over anhydrous magnesium sulfate, and concentrated under reduced pressure to obtain the residue. The residue was added with ethyl acetate and the resulting solid was filtered to obtain 7.06 g (95%) of 4-ethoxy-N-(3-fluoro-4-((5-iodopyrrolo[1,2-b]pyridazin-4-yl)oxy)phenyl)-1-(4-fluorophenyl)-2-oxo-1,2-dihydropyridin-3-carboxamide.

$^1$H NMR (400 MHz, DMSO-d$_6$) δ 10.61 (s, 1H), 8.01-8.00 (m, 1H), 7.95-7.90 (m, 2H), 7.86 (d, J=8.0 Hz, 1H), 7.51-7.42 (m, 3H), 7.39-7.34 (m, 2H), 7.01 (d, J=2.8 Hz, 1H), 6.51 (d, J=8.0 Hz, 1H), 5.86 (d, J=5.2 Hz, 1H), 4.26 (q, J=6.8 Hz, 2H), 1.30 (t, J=6.8 Hz, 3H)

Step 5) Preparation of 4-ethoxy-N-(3-fluoro-4-((5-(3-(hydroxymethyl)phenyl)pyrrolo[1,2-b]pyridazin-4-yl)oxy)phenyl)-1-(4-fluorophenyl)-2-oxo-1,2-dihydropyridin-3-carboxamide

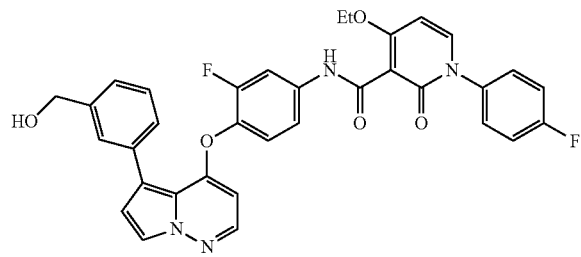 [SMILES: CCOc1ccn(-c2ccc(F)cc2)c(=O)c1C(=O)Nc1ccc(Oc2ccnn3ccc(-c4cccc(CO)c4)c23)c(F)c1]

4-Ethoxy-N-(3-fluoro-4-((5-iodopyrrolo[1,2-b]pyridazin-4-yl)oxy)phenyl)-1-(4-fluoro phenyl)-2-oxo-1,2-dihydropyridin-3-carboxamide (50 mg, 0.08 mmol), which was prepared in Step 4, was dissolved in dioxane solution (2 mL), added with Pd(PPh$_3$)$_4$ (9 mg, 0.008 mmol), (3-(hydroxymethyl)phenyl)boronic acid (18 mg, 0.12 mmol), and 1 M aqueous potassium carbonate solution (0.16 mL, 0.16 mol), and stirred under reflux for 12 hours to form a mixture. The mixture was extracted with dichloromethane and water, and the resulting organic layer was separated and dried over anhydrous magnesium sulfate, and concentrated under reduced pressure to obtain the residue. The residue was subjected to the prep. TLC(CH$_2$Cl$_2$:MeOH=30:1) method to obtain the target compound.

$^1$H NMR (400 MHz, CDCl$_3$) δ 11.59 (s, 1H), 7.90 (dd, J=12.8 and 2.4 Hz, 1H), 7.82 (d, J=5.2 Hz, 1H), 7.80 (d, J=2.8 Hz, 1H), 7.64 (s, 1H), 7.58-7.56 (m, 1H), 7.50 (d, J=8.0 Hz, 1H), 7.37-7.32 (m, 3H), 7.25-7.21 (m, 4H), 7.03 (t, J=8.8 Hz, 1H), 6.89 (d, J=2.8 Hz, 1H), 6.35 (d, J=8.0 Hz, 1H), 5.70 (d, J=5.2 Hz, 1H), 4.69 (s, 2H), 4.35 (q, J=7.2 Hz, 2H), 1.58 (t, J=7.2 Hz, 3H)

The target compounds of Examples 2 to 86 were prepared in the same manner as in Example 1, and the compounds were prepared using appropriate reactants in consideration of Reaction Scheme 1 and the structures of the compounds to be prepared.

EXAMPLE 2

Preparation of 4-ethoxy-N-(3-fluoro-4((5-phenylpyrrolo[1,2-b]pyridazin-4-yl)-oxy)phenyl)-1-(4-fluorophenyl)2-oxo-1,2-dihydropyridin-3-carboxamide

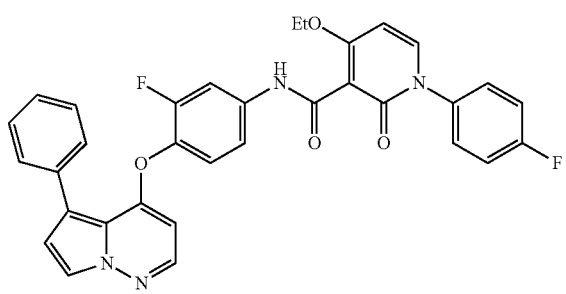 [SMILES: CCOc1ccn(-c2ccc(F)cc2)c(=O)c1C(=O)Nc1ccc(Oc2ccnn3ccc(-c4ccccc4)c23)c(F)c1]

$^1$H NMR (400 MHz, DMSO-d$_6$) δ 10.58 (s, 1H), 8.01-7.99 (m, 2H), 7.92-7.84 (m, 2H), 7.64-7.54 (m, 3H), 7.47-7.33 (m, 7H), 7.24-7.21 (m, 1H), 6.98 (d, J=2.8 Hz, 1H), 6.51 (d, J=8.0 Hz, 1H), 4.25 (q, J=7.2 Hz, 2H), 1.29 (t, J=7.2 Hz, 3H)

MS: 579 [M+H]$^+$

EXAMPLE 3

Preparation of 4-ethoxy-N-(3-fluoro-4-((5-(pyridin-3-yl)pyrrolo[1,2-b]pyridazin-4-yl)oxy)phenyl)-1-(4-fluorophenyl)-2-oxo-1,2-dihydropyridin-3-carboxamide

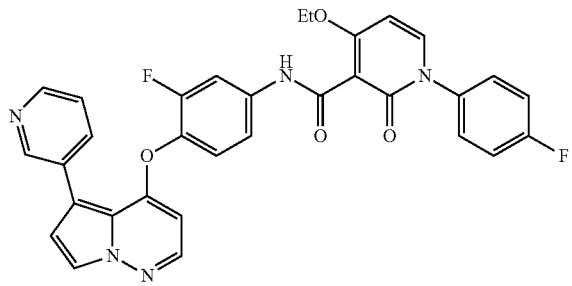 [SMILES: CCOc1ccn(-c2ccc(F)cc2)c(=O)c1C(=O)Nc1ccc(Oc2ccnn3ccc(-c4cccnc4)c23)c(F)c1]

$^1$H NMR (400 MHz, DMSO-d$_6$) δ 10.61 (s, 1H), 8.83 (s, 1H), 8.42 (d, J=3.6 Hz, 1H), 8.06-7.99 (m, 3H), 7.92-7.85 (m, 2H), 7.46-7.34 (m, 7H), 7.09 (d, J=2.4 Hz, 1H), 6.51 (d, J=8.0 Hz, 1H), 5.89 (d, J=4.8 Hz, 1H), 4.25 (q, J=6.8 Hz, 2H), 1.29 (t, J=6.8 Hz, 2H)

MS: 580 [M+H]$^+$

EXAMPLE 4

Preparation of 4-ethoxy-N-(3-fluoro-4-((5-thiazol-2-yl)pyrrolo[1,2-b]pyridazin-4-yl)oxy)phenyl)-1-(4-fluorophenyl)-2-oxo-1,2-dihydropyridin-3-carboxamide

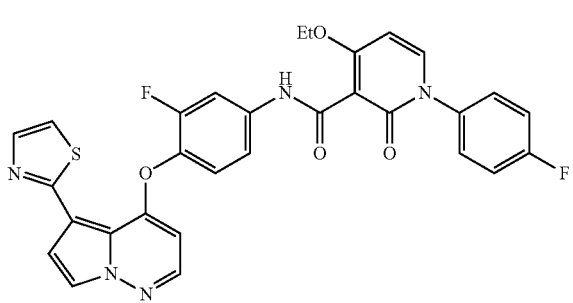 [SMILES: CCOc1ccn(-c2ccc(F)cc2)c(=O)c1C(=O)Nc1ccc(Oc2ccnn3ccc(-c4nccs4)c23)c(F)c1]

$^1$H NMR (400 MHz, DMSO-d$_6$) δ 10.64 (s, 1H), 8.08 (d, J=5.6 Hz, 1H), 8.01 (d, J=2.8 Hz, 1H), 7.97-7.94 (m, 1H), 7.86 (d, J=8.0 Hz, 1H), 7.80 (d, J=3.2 Hz, 1H), 7.62 (d, J=3.2 Hz, 1H), 7.52-7.44 (m, 4H), 7.41-7.34 (m, 3H), 6.52 (d, J=8.0 Hz, 1H), 6.05 (d, J=5.2 Hz, 1H), 4.26 (q, J=6.8 Hz, 2H), 1.30 (t, J=6.8 Hz, 3H)

MS: 586 [M+H]$^+$

EXAMPLE 5

Preparation of 4-ethoxy-N-(2-fluoro-4-((pyrazin-2-yl)pyrrolo[1,2-b]pyridazin-4-yl)oxy)phenyl)-1-(4-fluorophenyl)-2-oxo-1,2-dihydropyridin-3-carboxamide

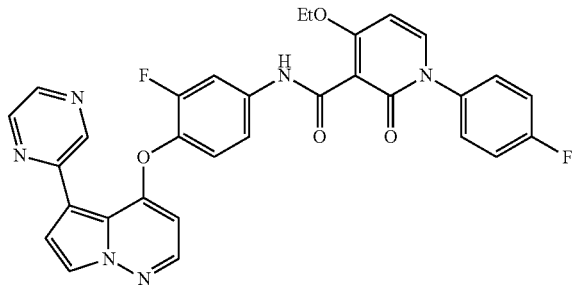 [SMILES: CCOc1ccn(-c2ccc(F)cc2)c(=O)c1C(=O)Nc1ccc(Oc2ccnn3ccc(-c4cnccn4)c23)c(F)c1]

¹H NMR (400 MHz, DMSO-d₆) δ 10.61 (s, 1H), 9.04 (s, 1H), 8.65-8.64 (m, 1H), 8.44-8.43 (m, 1H), 8.12-8.08 (m, 2H), 7.92 (d, J=13.6 Hz, 1H), 7.85 (d, J=8.0 Hz, 1H), 7.54-7.44 (m, 4H), 7.38-7.34 (m, 2H), 7.29-7.28 (m, 1H), 6.51 (d, J=8.0 Hz, 1H), 6.03 (d, J=5.2 Hz, 1H), 4.25 (q, J=6.8 Hz, 2H), 1.29 (t, J=6.8 Hz, 3H)

MS: 581 [M+H]⁺

EXAMPLE 6

Preparation of 4-ethoxy-N-(2-fluoro-4-((5-(1-methyl-1H-pyrazol-4-yl)pyrrolo[1,2-b]pyridazin-4-yl)oxy)phenyl)-1-(4-fluorophenyl)-2-oxo-1,2-dihydropyridin-3-carboxamide

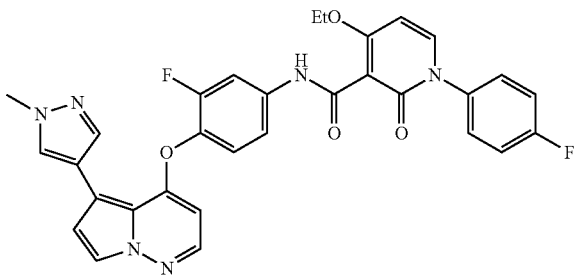 [SMILES: CCOc1ccn(-c2ccc(F)cc2)c(=O)c1C(=O)Nc1ccc(Oc2ccnn3ccc(-c4cnn(C)c4)c23)c(F)c1]

¹H NMR (400 MHz, DMSO-d₆) δ 10.60 (s, 1H), 7.95-7.85 (m, 5H), 7.69 (s, 1H), 7.50-7.45 (m, 4H), 7.39-7.35 (m, 2H), 6.95 (d, J=2.8 Hz, 1H), 6.52 (d, J=8.0 Hz, 1H), 5.74 (d, J=5.2 Hz, 1H), 4.26 (q, J=6.8 Hz, 2H), 3.82 (s, 3H), 1.30 (t, J=6.8 Hz, 3H)

MS: 583 [M+H]⁺

EXAMPLE 7

Preparation of 4-ethoxy-N-(3-fluoro-4-((5-pyridin-4-yl)pyrrolo[1,2-b]pyridazin-4-yl)oxy)phenyl)-1-(4-fluorophenyl)-2-oxo-1,2-dihydropyridin-3-carboxamide

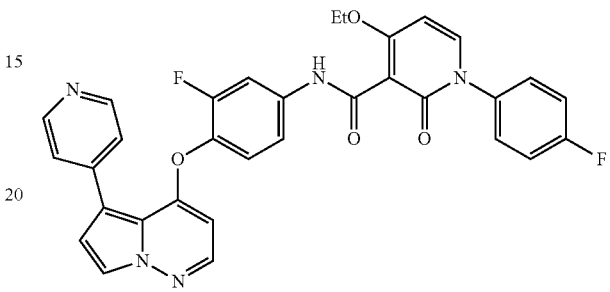

¹H NMR (400 MHz, DMSO-d₆) δ 10.60 (s, 1H), 8.52-8.50 (m, 2H), 8.09-8.06 (m, 2H), 7.94-7.93 (m, 1H), 7.86 (d, J=8.0 Hz, 1H), 7.64-7.62 (m, 2H), 7.49-7.44 (m, 4H), 7.39-7.34 (m, 2H), 7.16 (d, J=2.8 Hz, 1H), 6.51 (d, J=8.0 Hz, 1H), 5.96 (d, J=5.2 Hz, 1H), 4.25 (q, J=7.2 Hz, 2H), 1.30 (t, J=7.2 Hz, 3H)

MS: 580 [M+H]⁺

EXAMPLE 8

Preparation of 4-ethoxy-N-(3-fluoro-4-((5-(pyrimidin-5-yl)pyrrolo[1,2-b]pyridazin-4-yl)oxy)phenyl)-1-(4-fluorophenyl)-2-oxo-1,2-dihydropyridin-3-carboxamide

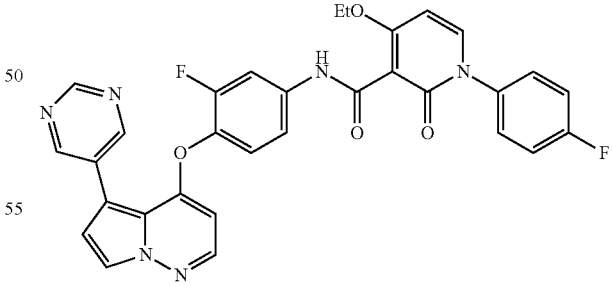

¹H NMR (400 MHz, DMSO-d₆) δ 10.61 (s, 1H), 9.04 (d, J=2.8 Hz, 3H), 8.11 (t, J=3.2 Hz, 2H), 7.93-7.90 (m, 1H), 7.86 (d, J=7.6 Hz, 1H), 7.53-7.44 (m, 4H), 7.39-7.34 (m, 2H), 7.21 (d, J=2.8 Hz, 1H), 6.51 (d, J=8.0 Hz, 1H), 5.96 (d, J=5.2 Hz, 1H), 4.25 (q, J=6.8 Hz, 2H), 1.30 (t, J=7.2 Hz, 3H)

MS: 581 [M+H]⁺

EXAMPLE 9

Preparation of 4-ethoxy-N-(3-fluoro-4-((5-(6-methoxypyridin-3-yl)pyrrolo[1,2-b]pyridazin-4-yl)oxy)phenyl)-1-(4-fluorophenyl)-2-oxo-1,2-dihydropyridin-3-carboxamide

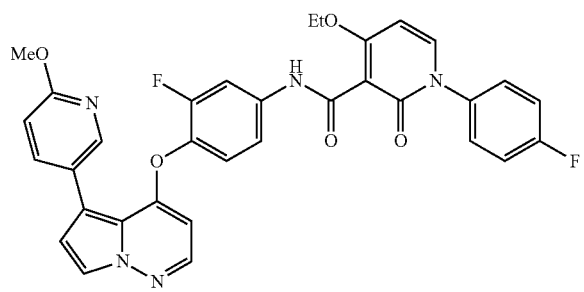 [SMILES: CCOc1ccn(-c2ccc(F)cc2)c(=O)c1C(=O)Nc1ccc(Oc2ccnn3ccc(-c4ccc(OC)nc4)c23)c(F)c1]

$^1$H NMR (400 MHz, DMSO-d$_6$) δ 10.59 (s, 1H), 8.38 (d, J=2.4 Hz, 1H), 8.02-8.00 (m, 2H), 7.94-7.88 (m, 2H), 7.85 (d, J=8.0 Hz, 1H), 7.47-7.44 (m, 4H), 7.38-7.34 (m, 2H), 7.01-6.99 (m, 1H), 6.82 (d, J=8.4 Hz, 1H), 6.51 (d, J=8.0 Hz, 1H), 5.83 (d, J=5.6 Hz, 1H), 4.26 (q, J=6.8 Hz, 2H), 3.84 (s, 3H), 1.29 (t, J=6.8 Hz, 3H)

MS: 610 [M+H]$^+$

EXAMPLE 10

Preparation of 4-ethoxy-N-(3-fluoro-4-((5-(thiophen-3-yl)pyrrolo[1,2-b]pyridazin-4-yl)oxy)phenyl)-1-(4-fluorophenyl)-2-oxo-1,2-dihydropyridin-3-carboxamide

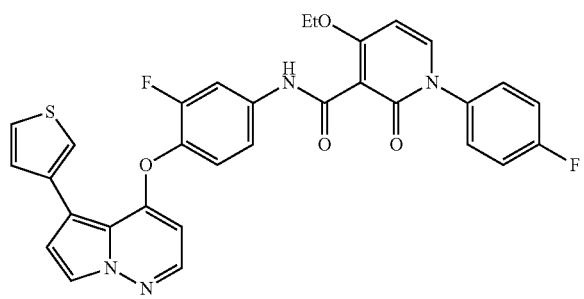 [SMILES: CCOc1ccn(-c2ccc(F)cc2)c(=O)c1C(=O)Nc1ccc(Oc2ccnn3ccc(-c4ccsc4)c23)c(F)c1]

$^1$H NMR (400 MHz, CDCl$_3$) δ 11.66 (s, 1H), 7.96-7.92 (m, 1H), 7.79 (d, J=5.6 Hz, 1H), 7.76 (d, J=2.8 Hz, 1H), 7.50 (d, J=8.0 Hz, 1H), 7.44-7.42 (m, 2H), 7.37-7.34 (m, 2H), 7.30-7.21 (m, 4H), 7.09 (t, J=8.4 Hz, 1H), 6.91 (d, J=2.8 Hz, 1H), 6.36 (d, J=8.0 Hz, 1H), 5.67-5.65 (m, 1H), 4.36 (q, J=4.0 Hz, 2H), 1.58 (t, J=8.0 Hz, 3H)

MS: 585 [M+H]$^+$

EXAMPLE 11

Preparation of 4-ethoxy-N-(3-fluoro-4-((5-(4-methoxyphenyl)pyrrolo[1,2-b]pyridazin-4-yl)oxy)phenyl)-1-(4-fluorophenyl)-2-oxo-1,2-dihydropyridin-3-carboxamide

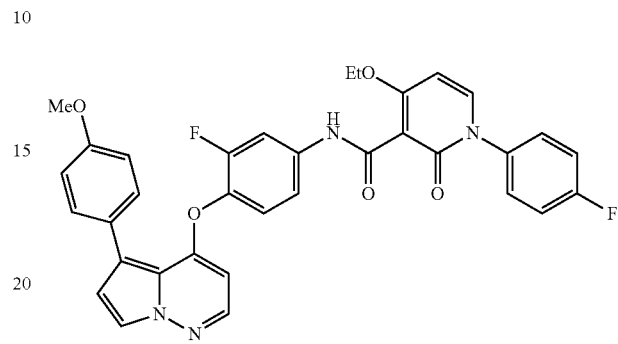

$^1$H NMR (400 MHz, CDCl$_3$) δ 11.60 (s, 1H), 7.93-7.89 (m, 1H), 7.80-7.77 (m, 2H), 7.58-7.55 (m, 2H), 7.50 (d, J=8.0 Hz, 1H), 7.37-7.34 (m, 2H), 7.25-7.21 (m, 2H), 7.05 (t, J=8.0 Hz, 1H), 6.91-6.88 (m, 2H), 6.84 (d, J=4.0 Hz, 1H), 6.77 (s, 1H), 6.36 (d, J=8.0 Hz, 1H), 5.64 (d, J=4.0 Hz, 1H), 4.36 (q, J=8.0 Hz, 2H), 3.81 (s, 3H), 1.58 (t, J=8.0 Hz, 3H)

MS: 609 [M+H]$^+$

EXAMPLE 12

Preparation of 4-ethoxy-N-(3-fluoro-4-((5-(2-fluorophenyl)pyrrolo[1,2-b]pyridazin-4-yl)oxy)phenyl)-1-(4-fluorophenyl)-2-oxo-1,2-dihydropyridin-3-carboxamide

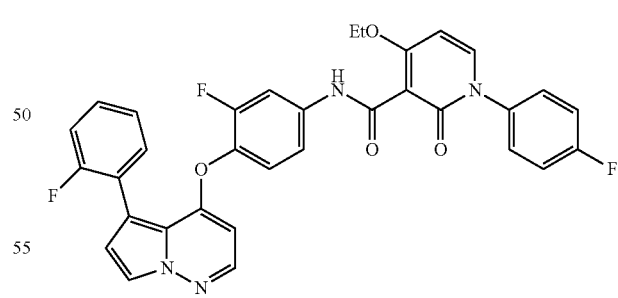

$^1$H NMR (400 MHz, CDCl$_3$) δ 11.59 (s, 1H), 7.88 (dd, J=12.4 and 2.4 Hz, 1H), 7.83 (d, J=5.2 Hz, 1H), 7.81 (d, J=2.8 Hz, 1H), 7.55-7.49 (m, 2H), 7.37-7.33 (m, 2H), 7.26-7.19 (m, 4H), 7.13-7.02 (m, 3H), 6.89-6.88 (m, 1H), 6.35 (d, J=8.0 Hz, 1H), 5.67 (d, J=5.2 Hz, 1H), 4.35 (q, J=7.2 Hz, 2H), 1.58 (t, J=7.2 Hz, 3H)

MS: 597 [M+H]$^+$

EXAMPLE 13

Preparation of N-(4-((5-(3,4-dimethoxyphenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

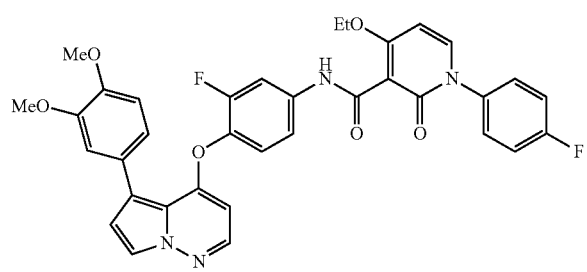 [SMILES: CCOc1ccn(-c2ccc(F)cc2)c(=O)c1C(=O)Nc1ccc(Oc2ccnn3ccc(-c4ccc(OC)c(OC)c4)c23)c(F)c1]

¹H NMR (400 MHz, CDCl₃) δ 11.64 (s, 1H), 7.96-7.92 (m, 1H), 7.80-7.78 (m, 2H), 7.51 (d, J=8.0 Hz, 1H), 7.37-7.34 (m, 2H), 7.25-7.21 (m, 4H), 7.18-7.15 (m, 1H), 7.04 (t, J=8.8 Hz, 1H), 6.89-6.86 (m, 2H), 6.37-6.35 (m, 1H), 5.63 (d, J=5.2 Hz, 1H), 4.36 (q, J=6.8 Hz, 2H), 3.89 (s, 3H), 3.83 (s, 3H), 1.58 (t, J=6.8 Hz, 3H)

MS: 639 [M+H]⁺

EXAMPLE 14

Preparation of 4-ethoxy-N-(3-fluoro-4-((5-(4-fluorophenyl)pyrrolo[1,2-b]pyridazin-4-yl)oxy)phenyl)-1-(4-fluorophenyl)-2-oxo-1,2-dihydropyridin-3-carboxamide

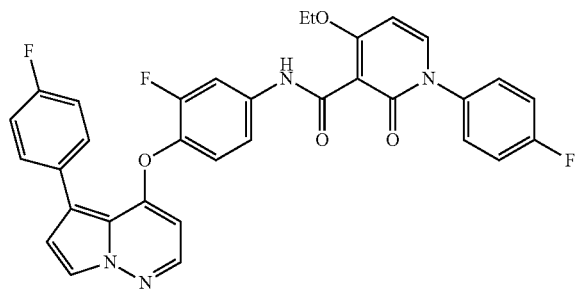 [SMILES: CCOc1ccn(-c2ccc(F)cc2)c(=O)c1C(=O)Nc1ccc(Oc2ccnn3ccc(-c4ccc(F)cc4)c23)c(F)c1]

¹H NMR (400 MHz, CDCl₃) δ 11.63 (s, 1H), 7.92 (dd, J=12.4 and 2.4 Hz, 1H), 7.81 (d, J=5.6 Hz, 1H), 7.78 (d, J=2.8 Hz, 1H), 7.60-7.56 (m, 2H), 7.50 (d, J=7.6 Hz, 1H), 7.37-7.33 (m, 2H), 7.26-7.21 (m, 3H), 7.06-7.00 (m, 3H), 6.83 (d, J=2.8 Hz, 1H), 6.35 (d, J=8.0 Hz, 1H), 5.66 (d, J=5.2 Hz, 1H), 4.35 (q, J=6.8 Hz, 2H), 1.58 (t, J=6.8 Hz, 3H)

MS: 597 [M+H]⁺

EXAMPLE 15

Preparation of 4-ethoxy-N-(3-fluoro-4-((5-(thiophen-2-yl)pyrrolo[1,2-b]pyridazin-4-yl)oxy)phenyl)-1-(4-fluorophenyl)-2-oxo-1,2-dihydropyridin-3-carboxamide

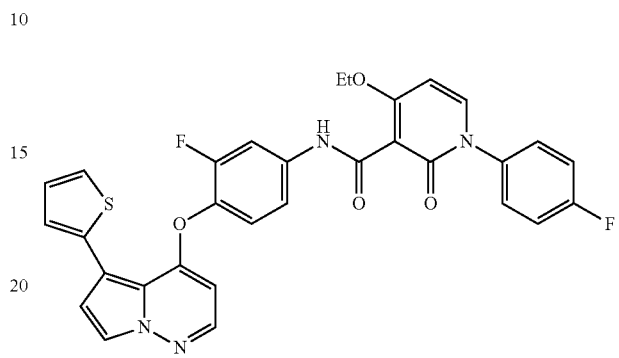

¹H NMR (400 MHz, CDCl₃) δ 11.67 (s, 1H), 7.96-7.92 (m, 1H), 7.80 (d, J=5.2 Hz, 1H), 7.74 (d, J=2.8 Hz, 1H), 7.52 (d, J=8.0 Hz, 1H), 7.38-7.35 (m, 2H), 7.30 (d, J=3.6 Hz, 1H), 7.24-7.19 (m, 4H), 7.13 (t, J=8.8 Hz, 1H), 7.01 (t, J=4.4 Hz, 1H), 6.94 (d, J=2.4 Hz, 1H), 6.37 (d, J=7.6 Hz, 1H), 5.68 (d, J=5.2 Hz, 1H), 4.37 (q, J=6.8 Hz, 2H), 1.59 (t, J=6.8 Hz, 3H)

MS: 585 [M+H]⁺

EXAMPLE 16

Preparation of N-(4-((5-(2-chloropyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

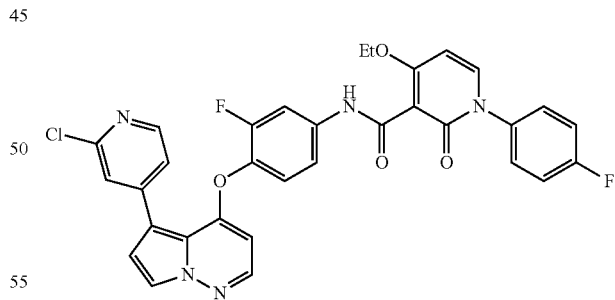

¹H NMR (400 MHz, CDCl₃) δ 11.72 (s, 1H), 8.30 (d, J=5.2 Hz, 1H), 8.00-7.96 (m, 1H), 7.91 (d, J=5.2 Hz, 1H), 7.83 (d, J=2.8 Hz, 1H), 7.61 (s, 1H), 7.51 (t, J=7.6 Hz, 2H), 7.38-7.35 (m, 2H), 7.30 (s, 1H), 7.25-7.22 (m, 2H), 7.08 (t, J=8.8 Hz, 1H), 6.95 (d, J=2.8 Hz, 1H), 6.38 (d, J=8.0 Hz, 1H), 5.81 (d, J=5.2 Hz, 1H), 4.37 (q, J=7.2 Hz, 2H), 1.59 (t, J=7.2 Hz, 3H)

MS: 614 [M+H]⁺

EXAMPLE 17

Preparation of N-(4-((5-(1H-pyrazol-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

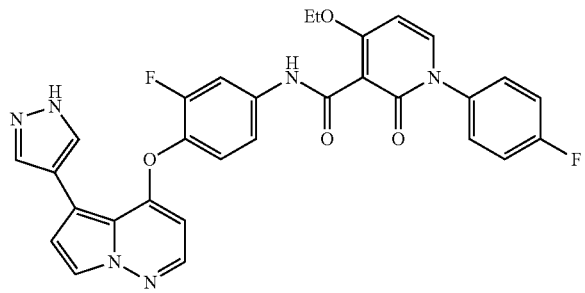 [SMILES: CCOc1ccn(-c2ccc(F)cc2)c(=O)c1C(=O)Nc1ccc(Oc2ccnn3ccc(-c4cn[nH]c4)c23)c(F)c1]

$^1$H NMR (400 MHz, CDCl$_3$) δ 11.68 (s, 1H), 7.97-7.93 (m, 1H), 7.89 (s, 2H), 7.78-7.76 (m, 2H), 7.52 (d, J=7.6 Hz, 1H), 7.38-7.35 (m, 2H), 7.30-7.22 (m, 4H), 7.11 (t, J=8.8 Hz, 1H), 6.89 (d, J=2.4 Hz, 1H), 6.37 (d, J=8.0 Hz, 1H), 5.64 (d, J=5.6 Hz, 1H), 4.37 (q, J=6.8 Hz, 2H), 1.59 (t, J=6.8 Hz, 3H)

MS: 569 [M+H]$^+$

EXAMPLE 18

Preparation of 4-ethoxy-N-(3-fluoro-4-((5-(1-methylsulfonyl)-1H-pyrazol-4-yl)pyrrolo[1,2-b]pyridazin-4-yl)oxy)phenyl)-1-(4-fluorophenyl)-2-oxo-1,2-dihydropyridin-3-carboxamide

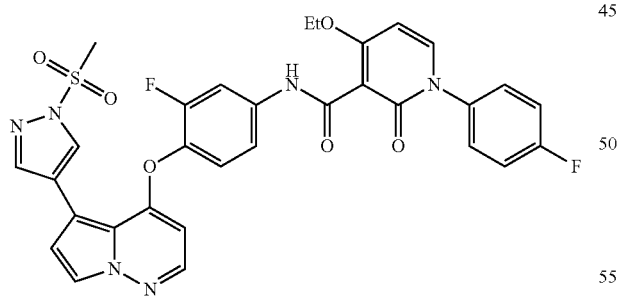

$^1$H NMR (400 MHz, CDCl$_3$) δ 11.67 (s, 1H), 8.21-8.14 (m, 2H), 7.98-7.94 (m, 1H), 7.83 (d, J=5.6 Hz, 1H), 7.77 (d, J=2.8 Hz, 1H), 7.52 (d, J=7.6 Hz, 1H), 7.38-7.35 (m, 2H), 7.33-7.30 (m, 1H), 7.25-7.22 (m, 2H), 7.12 (t, J=8.8 Hz, 1H), 6.87 (d, J=2.8 Hz, 1H), 6.37 (d, J=7.6 Hz, 1H), 5.73-5.72 (m, 1H), 4.37 (q, J=7.2 Hz, 2H), 3.31 (s, 3H), 1.59 (t, J=6.8 Hz, 3H)

MS: 647 [M+H]$^+$

EXAMPLE 19

Preparation of 4-ethoxy-N-(3-fluoro-4-((5-(2-fluoropyridin-4-yl)pyrrolo[1,2-b]pyridazin-4-yl)oxy)phenyl)-1-(4-fluorophenyl)-2-oxo-1,2-dihydropyridin-3-carboxamide

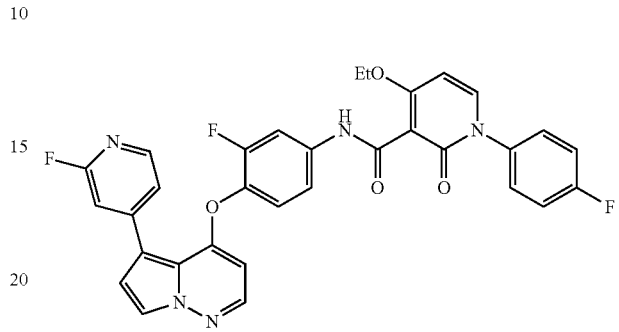

$^1$H NMR (400 MHz, CDCl$_3$) δ 11.70 (s, 1H), 8.13 (d, J=5.2 Hz, 1H), 7.98-7.95 (m, 1H), 7.90 (d, J=5.6 Hz, 1H), 7.83 (d, J=2.8 Hz, 1H), 7.52 (d, J=7.6 Hz, 1H), 7.46 (d, J=5.2 Hz, 1H), 7.38-7.35 (m, 2H), 7.30-7.19 (m, 4H), 7.07 (t, J=8.4 Hz, 1H), 6.96 (d, J=3.2 Hz, 1H), 6.37 (d, J=8.0 Hz, 1H), 5.81 (d, J=5.6 Hz, 1H), 4.37 (q, J=6.8 Hz, 2H), 1.58 (t, J=3.6 Hz, 3H)

MS: 598 [M+H]$^+$

EXAMPLE 20

Preparation of N-(4-((5-(5-chloro-2-methoxypyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

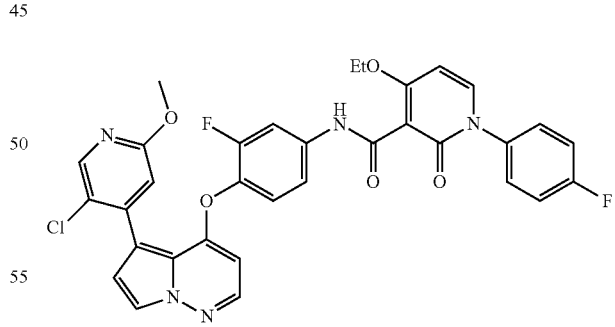

$^1$H NMR (400 MHz, CDCl$_3$) δ 11.64 (s, 1H), 7.98 (s, 1H), 7.94-7.91 (m, 1H), 7.87 (d, J=5.2 Hz, 1H), 7.81 (d, J=2.8 Hz, 1H), 7.51 (d, J=8.0 Hz, 1H), 7.41 (s, 1H), 7.37-7.34 (m, 2H), 7.24-7.22 (m, 3H), 7.00 (t, J=8.8 Hz, 1H), 6.94 (d, J=3.2 Hz, 1H), 6.37 (d, J=8.0 Hz, 1H), 5.73 (d, J=5.2 Hz, 1H), 4.36 (q, J=6.8 Hz, 2H), 3.88 (s, 3H), 1.58 (t, J=6.8 Hz, 3H)

MS: 644 [M+H]$^+$

EXAMPLE 21

Preparation of N-(4-((5-(6-aminopyridin-3-yl)pyrrolo[1,2-b]pyridazin-4-yl)oxy)-3fluorophenyl)-4-ethoxy-1-(4-fluorophenyl)-2-oxo-1,2-dihydropyridin-3-carboxamide

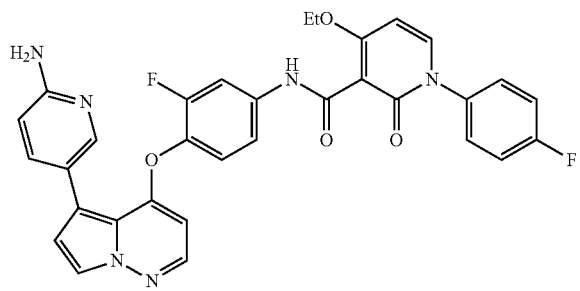 [SMILES: CCOc1ccn(-c2ccc(F)cc2)c(=O)c1C(=O)Nc1ccc(Oc2ccnn3ccc(-c4ccc(N)nc4)c23)c(F)c1]

¹H NMR (400 MHz, DMSO-d₆) δ 10.60 (s, 1H), 8.14 (d, J=2.0 Hz, 1H), 7.96-7.86 (m, 4H), 7.61-7.58 (m, 1H), 7.48-7.44 (m, 4H), 7.37 (t, J=8.8 Hz, 2H), 6.89 (d, J=2.8 Hz, 1H), 6.52 (d, J=8.0 Hz, 1H), 6.43 (d, J=8.4 Hz, 1H), 5.85 (s, 1H), 5.76-5.75 (m, 2H), 4.25 (q, J=6.8 Hz, 2H), 1.29 (t, J=6.8 Hz, 3H)

MS: 595 [M+H]⁺

EXAMPLE 22

Preparation of 4-ethoxy-N-(3-fluoro-4-((5-(1-piperidin-4-yl)-1H-pyrazol-4-yl)pyrrolo[1,2-b]pyridazin-4-yl)oxy)phenyl)-1-(4-fluorophenyl)-2-oxo-1,2-dihydropyridin-3-carboxamide

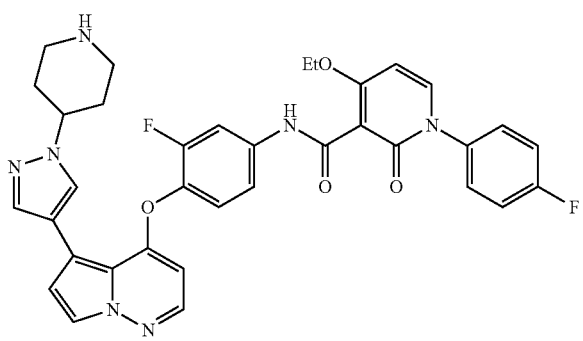 [SMILES: CCOc1ccn(-c2ccc(F)cc2)c(=O)c1C(=O)Nc1ccc(Oc2ccnn3ccc(-c4cnn(C5CCNCC5)c4)c23)c(F)c1]

¹H NMR (400 MHz, CDCl₃) δ 11.06 (s, 1H), 7.97-7.94 (m, 1H), 7.79-7.71 (m, 4H), 7.52 (d, J=7.6 Hz, 1H), 7.38-7.35 (m, 2H), 7.26-7.21 (m, 3H), 7.10 (t, J=8.4 Hz, 1H), 6.85 (d, J=2.8 Hz, 1H), 6.37 (d, J=8.0 Hz, 1H), 5.65 (d, J=5.2 Hz, 1H), 4.37 (q, J=6.8 Hz, 2H), 4.23-4.18 (m, 1H), 3.24-3.21 (m, 2H), 2.80-2.74 (m, 2H), 2.19-2.15 (m, 2H), 1.91-1.97 (m, 2H), 1.59 (t, J=6.8 Hz, 3H)

MS: 652 [M+H]⁺

EXAMPLE 23

Preparation of 4-ethoxy-N-(3-fluoro-4-((5-(3-formylphenyl)pyrrolo[1,2-b]pyridazin-4-yl)oxy)phenyl)-1-(4-fluorophenyl)-2-oxo-1,2-dihydropyridin-3-carboxamide

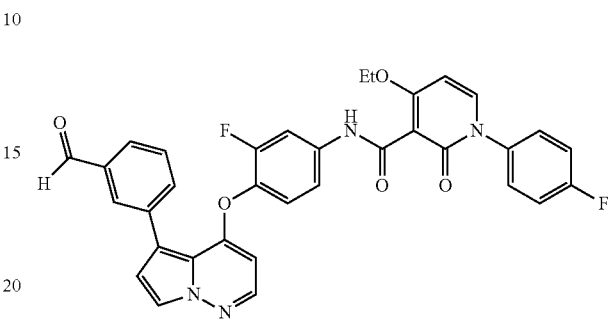

¹H NMR (400 MHz, CDCl₃) δ 11.65 (s, 1H), 10.02 (s, 1H), 8.16-8.15 (m, 1H), 7.95-7.91 (m, 2H), 7.86 (d, J=5.2 Hz, 1H), 7.83 (d, J=2.8 Hz, 1H), 7.76-7.74 (m, 1H), 7.53-7.48 (m, 2H), 7.38-7.34 (m, 2H), 7.24-7.22 (m, 3H), 7.06 (t, J=8.8 Hz, 1H), 6.93 (d, J=3.2 Hz, 1H), 6.37 (d, J=7.6 Hz, 1H), 5.73 (d, J=5.6 Hz, 1H), 4.37 (q, J=7.2 Hz, 2H), 1.59 J=7.2 Hz, 3H)

MS: 607 [M+H]⁺

EXAMPLE 24

Preparation of 4-ethoxy-N-(3-fluoro-4-((5-(2-(piperazin-1-yl)pyridin-4-yl)pyrrolo[1,2-b]pyridazin-4-yl)oxy)phenyl)-1-(4-fluorophenyl)-2-oxo-1,2-dihydropyridin-3-carboxamide

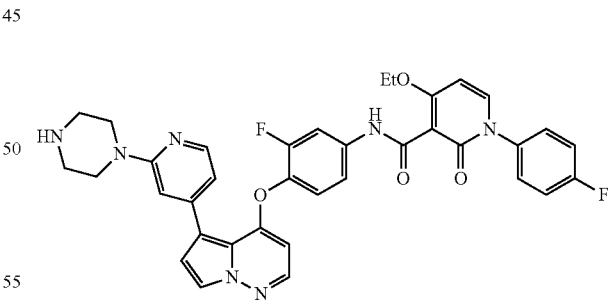

¹H NMR (400 MHz, CDCl₃) δ 11.60 (s, 1H), 8.15 (d, J=4.0 Hz, 1H), 7.99-7.95 (m, 1H), 7.86-7.80 (m, 2H), 7.51 (d, J=8.0 Hz, 1H), 7.37-7.34 (m, 2H), 7.25-7.21 (m, 3H), 7.06-7.01 (m, 2H), 6.95-6.91 (m, 2H), 6.36 (d, J=8.0 Hz, 1H), 5.73 (d, J=8.0 Hz, 1H), 4.36 (q, J=7.2 Hz, 2H), 3.51 (t, J=4.8 Hz, 4H), 2.93 (t, J=5.2 Hz, 4H), 2.18 (s, 1H), 1.58 (t, J=7.2 Hz, 3H)

MS: 665 [M+H]⁺

EXAMPLE 25

Preparation of N-(4-((5-(6-acetamidopyridin-3-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

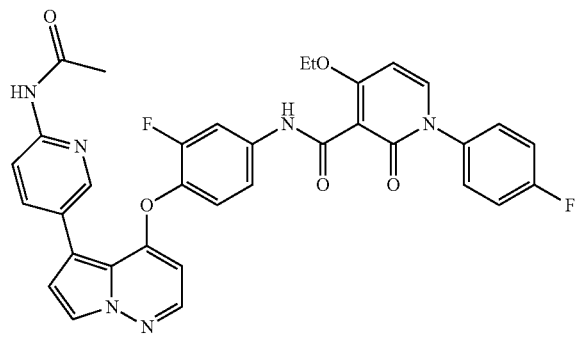 [SMILES: CCOc1ccn(-c2ccc(F)cc2)c(=O)c1C(=O)Nc1ccc(Oc2ccnn3ccc(-c4ccc(NC(C)=O)nc4)c23)c(F)c1]

$^1$H NMR (400 MHz, CDCl$_3$) δ 11.63 (s, 1H), 8.51-8.50 (m, 1H), 8.36 (s, 1H), 8.20 (d, J=8.4 Hz, 1H), 7.99-7.90 (m, 2H), 7.85-7.81 (m, 2H), 7.50 (d, J=7.6 Hz, 1H), 7.37-7.34 (m, 2H), 7.24-7.22 (m, 3H), 7.03 (t, J=8.8 Hz, 1H), 6.86 (d, J=2.8 Hz, 1H), 6.36 (d, J=8.0 Hz, 1H), 5.69 (d, J=5.6 Hz, 1H), 4.36 (q, J=7.2 Hz, 2H), 2.17 (s, 3H), 1.59 (t, J=6.8 Hz, 3H)

MS: 637 [M+H]$^+$

EXAMPLE 26

Preparation of N-(4-((5-(2-acetylpyridin-4-yl)pyrrolo[1,2-b]pyridazin-4-yl)oxy)-3-fluorophenyl)-4-ethoxy-1-(4-fluorophenyl-2-oxo-1,2-dihydropyridin-3-carboxamide

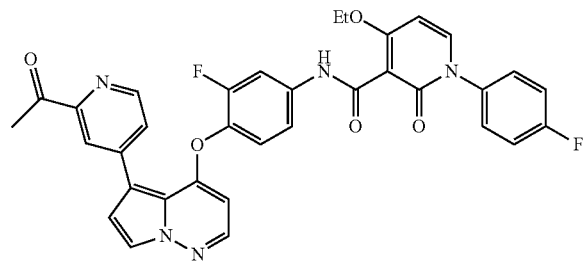 [SMILES: CCOc1ccn(-c2ccc(F)cc2)c(=O)c1C(=O)Nc1ccc(Oc2ccnn3ccc(-c4ccnc(C(C)=O)c4)c23)c(F)c1]

$^1$H NMR (400 MHz, CDCl$_3$) δ 11.69 (s, 1H), 8.61 (d, J=4.8 Hz, 1H), 8.33 (s, 1H), 7.99-7.95 (m, 1H), 7.91 (d, J=5.2 Hz, 1H), 7.84 (d, J=2.8 Hz, 1H), 7.78-7.76 (m, 1H), 7.52 (d, J=8.0 Hz, 1H), 7.38-7.35 (m, 2H), 7.30-7.22 (m, 3H), 7.13 (t, J=8.8 Hz, 1H), 7.01 (d, J=2.8 Hz, 1H), 6.37 (d, J=8.0 Hz, 1H), 5.80 (d, J=5.2 Hz, 1H), 4.36 (q, J=7.2 Hz, 2H), 2.73 (s, 3H), 1.59 (t, J=6.8 Hz, 3H)

MS: 622 [M+H]$^+$

EXAMPLE 27

Preparation of N-(4-((5-(3-acetylphenyl)pyrrolo[1,2-b]pyridazin-4-yl)oxy)-3-fluorophenyl)-4-ethoxy-1-(4-fluorophenyl-2-oxo-1,2-dihydropyridin-3-carboxamide

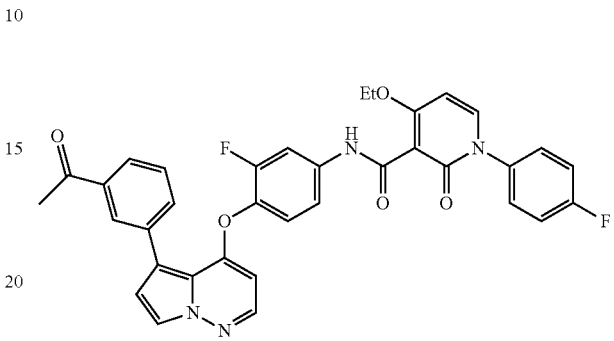

$^1$H NMR (400 MHz, CDCl$_3$) δ 11.64 (s, 1H), 8.27-8.26 (m, 1H), 7.96-7.92 (m, 1H), 7.86-7.82 (m, 4H), 7.51 (d, J=7.8 Hz, 1H), 7.44 (t, J=7.7 Hz, 1H), 7.37-7.32 (m, 2H), 7.24-7.22 (m, 3H), 7.06 (t, J=8.7 Hz, 1H), 6.93 (d, J=2.8 Hz, 1H), 6.37 (d, J=7.9 Hz, 1H), 5.71 (d, J=5.0 Hz, 1H), 4.37 (q, J=7.0 Hz, 2H), 2.58 (s, 3H), 1.59 (t, J=7.0 Hz, 3H)

MS: 621 [M+H]$^+$

EXAMPLE 28

Preparation of N-(3-fluoro-4-((5-(pyridin-4-yl)pyrrolo[1,2-b]pyridazin-4-yl)oxy)phenyl)-4-methoxy-2-oxo-1-phenyl-1,2-dihydropyridin-3-carboxamide

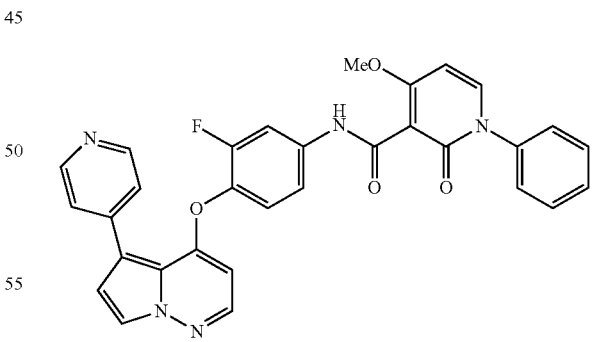

$^1$H NMR (400 MHz, CDCl$_3$) δ 11.85 (s, 1H), 8.55 (d, J=6.0 Hz, 2H), 8.01-7.97 (m, 1H), 7.89 (d, J=5.4 Hz, 1H), 7.83 (d, J=2.9 Hz, 1H), 7.60-7.52 (m, 6H), 7.39-7.37 (m, 2H), 7.31-7.28 (m, 1H), 7.06 (t, J=8.7 Hz, 1H), 6.96 (d, J=2.9 Hz, 1H), 6.41 (d, J=7.9 Hz, 1H), 5.78 (d, J=5.3 Hz, 1H), 4.12 (s, 3H)

MS: 548 [M+H]$^+$

EXAMPLE 29

Preparation of N-(3-fluoro-4-((5-(3-hydroxymethyl)phenyl)pyrrolo[1,2-b]pyridazin-4-yl)oxy)phenyl)-1-(4-fluorophenyl)-2-oxo-1,2-dihydropyridin-3-carboxamide

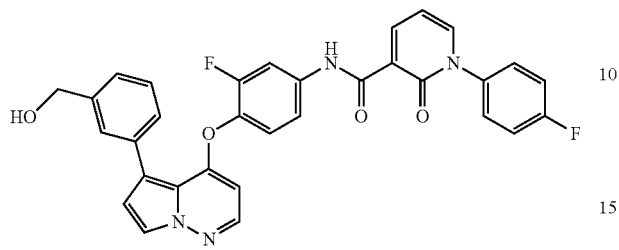

$^{1}$H NMR (400 MHz, CDCl$_{3}$) δ 11.97 (s, 1H), 8.73-8.71 (m, 1H), 7.93-7.89 (m, 1H), 7.84-7.80 (m, 2H), 7.65-7.61 (m, 2H), 7.59-7.57 (m, 1H), 7.41-7.25 (m, 7H), 7.08 (t, J=8.4 Hz, 1H), 6.90 (d, J=2.4 Hz, 1H), 6.61 (t, J=6.8 Hz, 1H), 5.71 (d, J=5.6 Hz, 1H), 4.70 (s, 2H)
MS: 565 [M+H]$^{+}$

EXAMPLE 30

Preparation of 4-ethoxy-N-(4-((5-(3-(ethylsulfonyl)phenyl)pyrrolo[1,2-b]pyridazin-4-yl)oxy)-3-fluorophenyl)-1-(4-fluorophenyl)-2-oxo-1,2-dihydropyridin-3-carboxamide

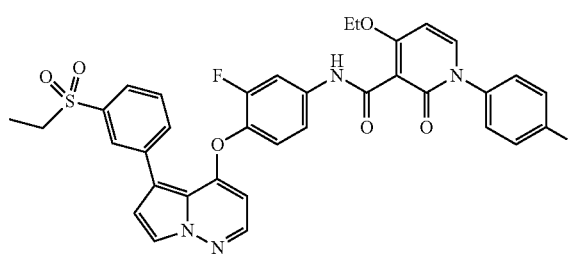

$^{1}$H NMR (400 MHz, CDCl$_{3}$) δ 11.50 (s, 1H), 8.19 (t, 1H), 7.92-7.81 (m, 4H), 7.75-7.73 (m, 1H), 7.52-7.48 (m, 2H), 7.36-7.33 (m, 2H), 7.29-7.20 (m, 3H), 7.10 (t, J=2.8 Hz, 1H), 6.34 (d, J=8.0 Hz, 1H), 5.74-5.73 (m, 1H), 4.38-4.33 (q, 2H), 3.04-2.99 (q, 2H), 1.58 (t, J=7.2 Hz, 3H), 1.16 (t, J=7.6 Hz, 3H)
MS: 671 [M+H]$^{+}$

EXAMPLE 31

Preparation of 4-ethoxy-N-(3-fluoro-4-((5-(3-(methylsulfonyl)phenyl)pyrrolo[1,2-b]pyridazin-4-yl)oxy)phenyl)-1-(4-fluorophenyl)-2-oxo-1,2-dihydropyridin-3-carboxamide

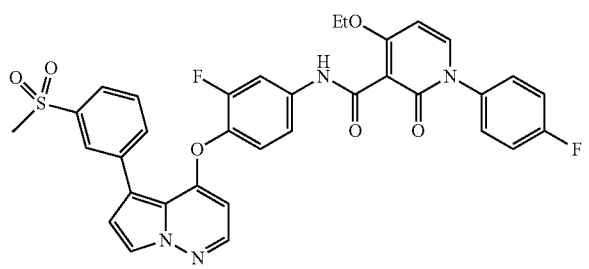 [SMILES: CCOc1ccn(-c2ccc(F)cc2)c(=O)c1C(=O)Nc1ccc(Oc2ccnn3ccc(-c4cccc(S(C)(=O)=O)c4)c23)c(F)c1]

$^{1}$H NMR (400 MHz, CDCl$_{3}$) δ 11.49 (s, 1H), 8.22 (t, 1H), 7.92-7.81 (m, 4H), 7.77 (m, 1H), 7.67 (m, 1H), 7.53-7.47 (m, 2H), 7.36-7.33 (m, 2H), 7.29-7.20 (m, 3H), 7.10 (t, 1H), 6.92 (d, J=3.6 Hz, 1H), 6.33 (d, J=7.6 Hz, 1H), 5.75-5.74 (q, 1H), 4.38-4.33 (q, 2H), 2.94 (s, 3H), 1.58 (t, J=7.2 Hz, 3H)
MS: 657 [M+H]$^{+}$

EXAMPLE 32

Preparation of 4-ethoxy-N-(3-fluoro-4-((5-(3-sulfamoylphenyl)pyrrolo[1,2-b]pyridazin-4-yl)oxy)phenyl)-1-(4-fluorophenyl)-2-oxo-1,2-dihydropyridin-3-carboxamide

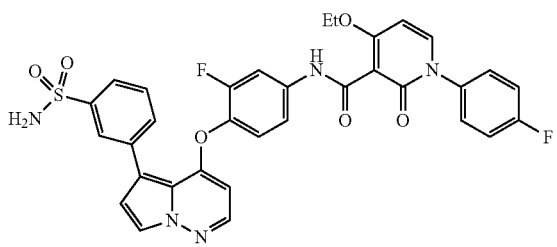 [SMILES: CCOc1ccn(-c2ccc(F)cc2)c(=O)c1C(=O)Nc1ccc(Oc2ccnn3ccc(-c4cccc(S(N)(=O)=O)c4)c23)c(F)c1]

$^{1}$H NMR (400 MHz, CDCl$_{3}$) δ 11.45 (s, 1H), 8.17 (t, 1H), 7.88-7.81 (m, 4H), 7.78-7.75 (m, 1H), 7.49-7.45 (m, 2H), 7.36-7.33 (m, 2H), 7.26-7.20 (m, 3H), 7.02 (t, 1H), 6.91 (d, J=2.8 Hz, 1H), 6.33 (d, J=8.0 Hz, 1H), 5.79 (d, J=5.2 Hz, 1H), 4.37-4.35 (q, 2H), 2.52 (d, J=5.2 Hz, 3H), 1.58 (t, J=6.8 Hz, 3H)
MS: 658 [M+H]$^{+}$

EXAMPLE 33

Preparation of N-(3-fluoro-4-((5-(pyridin-4-yl)pyrrolo[1,2-b]pyridazin-4-yl)oxy)phenyl)-4-methoxy-2-oxo-1-phenyl-1,2-dihydropyridin-3-carboxamide

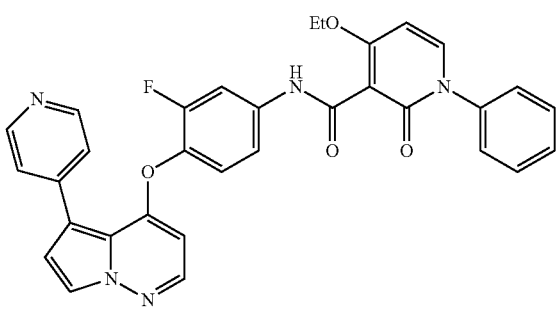 [SMILES: CCOc1ccn(-c2ccccc2)c(=O)c1C(=O)Nc1ccc(Oc2ccnn3ccc(-c4ccncc4)c23)c(F)c1]

$^{1}$H NMR (400 MHz, CDCl$_{3}$) δ 11.64 (s, 1H), 8.27-8.26 (m, 1H), 7.96-7.92 (m, 1H), 7.86-7.82 (m, 4H), 7.51 (d, J=7.8 Hz, 1H), 7.44 (t, J=7.7 Hz, 1H), 7.37-7.32 (m, 2H), 7.24-7.22 (m, 3H), 7.06 (t, J=8.7 Hz, 1H), 6.93 (d, J=2.8 Hz, 1H), 6.37 (d, J=7.9 Hz, 1H), 5.71 (d, J=5.0 Hz, 1H), 4.37 (q, J=7.0 Hz, 2H), 2.58 (s, 3H), 1.59 (t, J=7.0 Hz, 3H)
MS: 548 [M+H]+

EXAMPLE 34

Preparation of N-(4-((5-(3-acetylphenyl)pyrrolo[1,2-b]pyridazin-4-yl)oxy)-3-fluorophenyl)-4-ethoxy-1-(4-fluorophenyl-2-oxo-1,2-dihydropyridin-3-carboxamide

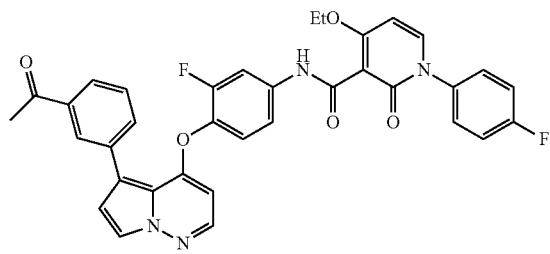 [SMILES: CCOc1ccn(-c2ccc(F)cc2)c(=O)c1C(=O)Nc1ccc(Oc2ccnn3ccc(-c4cccc(C(C)=O)c4)c23)c(F)c1]

$^1$H NMR (400 MHz, CDCl$_3$) δ 11.85 (s, 1H), 8.55 (d, J=6.0 Hz, 2H), 8.01-7.97 (m, 1H), 7.89 (d, J=5.4 Hz, 1H), 7.83 (d, J=2.9 Hz, 1H), 7.60-7.52 (m, 6H), 7.39-7.37 (m, 2H), 7.31-7.28 (m, 1H), 7.06 (t, J=8.7 Hz, 1H), 6.96 (d, J=2.9 Hz, 1H), 6.41 (d, J=7.9 Hz, 1H), 5.78 (d, J=5.3 Hz, 1H), 4.12 (s, 3H)
MS: 621 [M+H]$^+$

EXAMPLE 35

Preparation of N-(4-((5-(3-(N-methylsulfamoyl)phenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

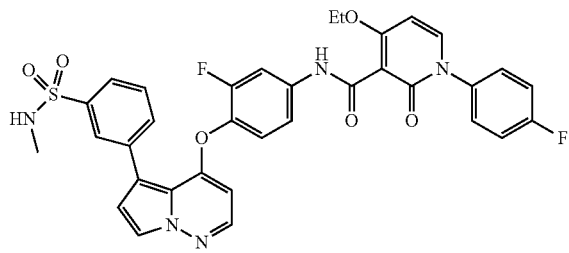 [SMILES: CCOc1ccn(-c2ccc(F)cc2)c(=O)c1C(=O)Nc1ccc(Oc2ccnn3ccc(-c4cccc(S(=O)(=O)NC)c4)c23)c(F)c1]

$^1$H NMR (400 MHz, CDCl$_3$) δ 11.5 (s, 1H), 8.14 (t, 1H), 7.93-7.81 (m, 4H), 7.73-7.67 (m, 1H), 7.50-7.46 (m, 2H), 7.36-7.33 (m, 2H), 7.26-7.23 (m, 2H), 7.08 (t, 1H), 6.91 (d, J=2.8 Hz, 1H), 6.34 (d, J=7.6 Hz, 1H), 5.74 (d, J=6.4 Hz, 1H), 4.37-4.35 (q, 2H), 2.52 (d, J=5.2 Hz, 3H), 1.58 (t, J=6.8 Hz, 3H)
MS: 672 [M+H]$^+$

EXAMPLE 36

Preparation of N-(4-((5-(3-(N,N-dimethylsulfamoyl)phenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

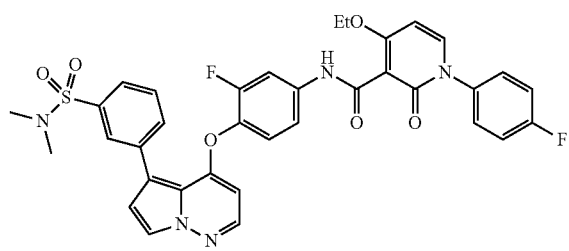 [SMILES: CCOc1ccn(-c2ccc(F)cc2)c(=O)c1C(=O)Nc1ccc(Oc2ccnn3ccc(-c4cccc(S(=O)(=O)N(C)C)c4)c23)c(F)c1]

$^1$H NMR (400 MHz, CDCl$_3$) δ 11.49 (s, 1H), 8.09 (t, 1H), 7.91-7.81 (m, 4H), 7.63-7.61 (m, 1H), 7.51-7.47 (m, 2H), 7.37-7.33 (m, 2H), 7.26-7.20 (m, 2H), 7.08 (t, 1H), 6.90 (d, J=3.2 Hz, 1H), 6.34 (d, J=7.6 Hz, 1H), 5.73 (d, J=3.6 Hz, 1H), 4.38-4.33 (q, 2H), 2.60 (s, 6H), 1.58 (t, J=6.8 Hz, 3H)
MS: 686 [M+H]$^+$

EXAMPLE 37

Preparation of 4-ethoxy-N-(3-fluoro-4-((5-(4-nitrophenyl)pyrrolo[1,2-b]pyridazin-4-yl)oxy)phenyl)-1-(4-fluorophenyl)-2-oxo-1,2-dihydropyridin-3-carboxamide

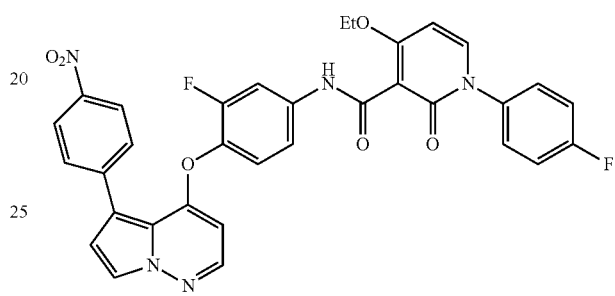

$^1$H NMR (400 MHz, CDCl$_3$) δ 11.68 (s, 1H), 8.21-8.19 (m, 2H), 7.91-7.93 (m, 1H), 7.89 (d, J=5.6 Hz, 1H), 7.83 (d, J=2.8 Hz, 1H), 7.79-7.77 (m, 2H), 7.51 (d, J=7.6 Hz, 1H), 7.37-7.34 (m, 2H), 7.28-7.21 (m, 3H), 7.05 (t, J=8.4 Hz, 1H), 6.94 (d, J=2.8 Hz, 1H), 6.36 (d, J=8.0 Hz, 1H), 5.75 (d, J=5.2 Hz, 1H), 4.39-4.34 (q, 2H), 1.59 (d, J=6.8 Hz, 3H)
MS: 624 [M+H]$^+$

EXAMPLE 38

Preparation of N-(4-((5-(4-aminophenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

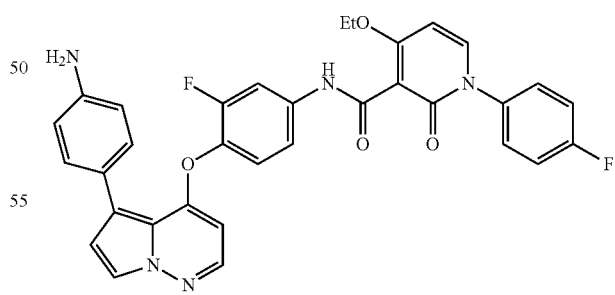

$^1$H NMR (400 MHz, CDCl$_3$) δ 11.58 (s, 1H), 7.92-7.88 (m, 1H), 7.77-7.75 (m, 2H), 7.50 (d, J=8.0 Hz, 1H), 7.45-7.43 (m, 2H), 7.23-7.21 (m, 2H) 7.37-7.34 (m, 2H), 7.04 (t, J=8.4 Hz, 2H), 6.81 (d, J=2.4 Hz, 1H), 6.68 (d, J=8.4 Hz, 1H), 6.36 (d, J=8.0 Hz, 1H), 5.61 (d, J=5.2 Hz, 1H), 5.4 (br, 2H), 4.37-4.35 (q, 2H), 1.59 (d, J=6.8 Hz, 3H)
MS: 594 [M+H]$^+$

EXAMPLE 39

Preparation of 4-ethoxy-N-(3-fluoro-4-((5-(3-((2-methoxyethoxy)methyl)phenyl)pyrrolo[1,2-b]pyridazin-4-yl)oxy)phenyl)-1-(4-fluorophenyl)-2-oxo-1,2-dihydropyridin-3-carboxamide

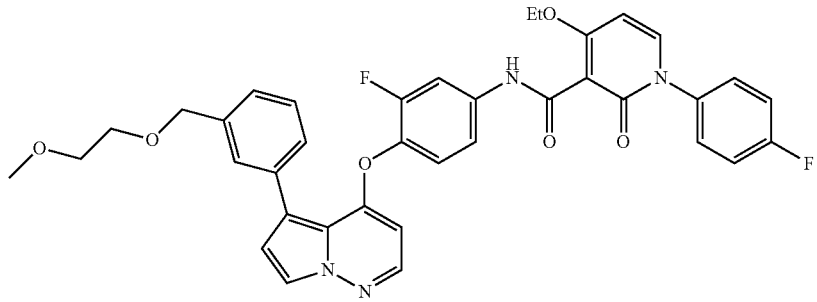 [SMILES: CCOc1ccn(-c2ccc(F)cc2)c(=O)c1C(=O)Nc1ccc(Oc2ccnn3ccc(-c4cccc(COCCOC)c4)c23)c(F)c1]

$^1$H NMR (400 MHz, CDCl$_3$) δ 11.60 (s, 1H), 7.93-7.90 (dd, 2H), 7.81 (d, J=5.2 Hz, 1H), 7.79 (d, J=2.8 Hz, 1H), 7.69-7.63 (m, 3H), 7.51-7.46 (m, 2H), 7.37-7.30 (m, 3H), 7.24-7.21 (m, 2H) 7.04 (t, 1H), 6.88 (d, J=2.8 Hz, 1H), 6.36 (d, J=8.0 Hz, 1H), 5.61 (d, J=5.2 Hz, 1H), 4.57 (s, 2H), 4.37-4.35 (q, 2H), 3.56-3.53 (m, 2H), 3.47-3.34 (m, 2H), 1.59 (d, J=6.8 Hz, 3H)

MS: 667 [M+H]$^+$

EXAMPLE 40

Preparation of N-(3-fluoro-4-((5-(2-methoxypyridin-4-yl)pyrrolo[1,2-b]pyridazin-4-yl)oxy)phenyl)-1-(4-fluorophenyl)-2-oxo-1,2-dihydropyridin-3-carboxamide

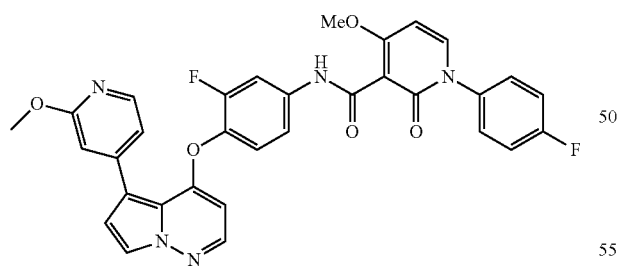

$^1$H NMR (400 MHz, CDCl$_3$) δ 11.72 (s, 1H), 8.09 (d, J=5.2 Hz, 1H), 7.86 (d, J=5.2 Hz, 1H), 7.80 (d, J=2.8 Hz, 1H), 7.55 (d, J=7.6 Hz, 1H), 7.37 (d, J=4.0 Hz, 1H), 7.35-7.34 (m, 2H) 7.27-7.20 (m, 3H), 7.18 (t, 1H), 7.01 (s, 1H), 6.93 (d, J=2.8 Hz, 1H), 6.40 (d, J=8.0 Hz, 1H), 5.75 (d, J=5.2 Hz, 1H), 4.11 (s, 3H), 3.92 (s, 3H), 3.56-3.53 (m, 2H), 3.47-3.34 (m, 2H), 1.59 (d, J=6.8 Hz, 3H)

MS: 596 [M+H]$^+$

EXAMPLE 41

Preparation of N-(4-((5-(3-(dimethylcarbamoyl)phenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

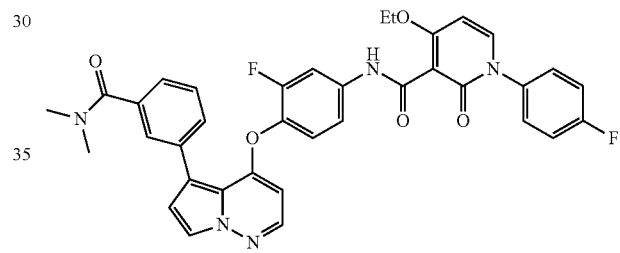

$^1$H NMR (400 MHz, CDCl$_3$) δ 11.64 (s, 1H), 7.95-7.91 (m, 1H), 7.83-7.79 (m, 2H), 7.68-7.64 (m, 2H), 7.51 (d, J=7.8 Hz, 1H), 7.39-7.33 (m, 3H), 7.28-7.21 (m, 4H), 7.03 (t, J=8.7 Hz, 1H), 6.88 (d, J=2.8 Hz, 1H), 6.36 (d, J=7.9 Hz, 1H), 5.69 (d, J=5.3 Hz, 1H), 4.36 (q, J=7.0 Hz, 2H), 3.10 (s, 3H), 2.92 (s, 3H), 1.58 (t, J=7.0 Hz, 3H)

MS: 650 [M+H]$^+$

EXAMPLE 42

Preparation of N-(3-fluoro-4-((5-(pyridin-4-yl)pyrrolo[1,2-b]pyridazin-4-yl)oxy)phenyl)-N-(4-fluorophenyl)cyclopropane-1,1-dicarboxyamide

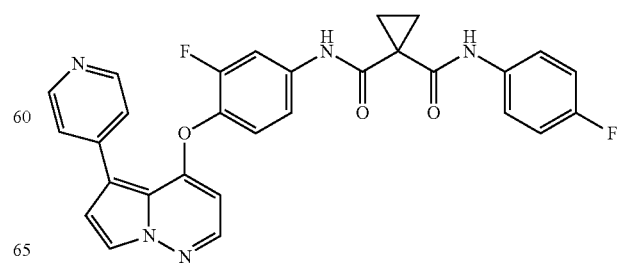

¹H NMR (400 MHz, CDCl₃) δ 10.13 (s, 1H), 8.54 (d, J=5.4 Hz, 2H), 8.23 (s, 1H), 7.89 (d, J=5.4 Hz, 1H), 7.85 (d, J=2.9 Hz, 1H), 7.77-7.73 (m, 1H), 7.57 (d, J=6.0 Hz, 2H), 7.46-7.41 (m, 2H), 7.23-7.21 (m, 1H), 7.14-7.12 (m, 1H), 7.09-7.03 (m, 2H), 6.97 (d, J=2.9 Hz, 1H), 5.77 (d, J=5.3 Hz, 1H), 1.81 (q, J=5.2 Hz, 2H), 1.62 (q, J=4.6 Hz, 2H)

MS: 526 [M+H]⁺

EXAMPLE 43

Preparation of 4-ethoxy-N-(3-fluoro-4-((5-(3-(2-hydroxypropan-2-yl)phenyl)pyrrolo[1,2-b]pyridazin-4-yl)oxy)phenyl)-1-(4-fluorophenyl)-2-oxo-1,2-dihydropyridin-3-carboxamide

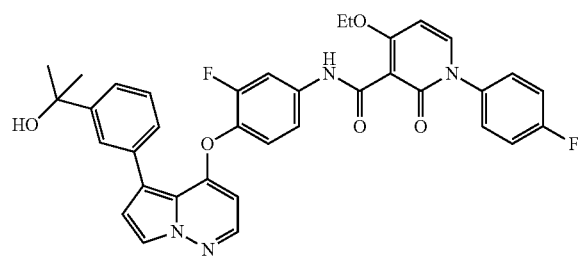 [SMILES: CCOc1ccn(-c2ccc(F)cc2)c(=O)c1C(=O)Nc1ccc(Oc2ccnn3ccc(-c4cccc(C(C)(C)O)c4)c23)c(F)c1]

¹H NMR (400 MHz, CDCl₃) δ 11.59 (s, 1H), 7.94-7.89 (m, 1H), 7.82-7.78 (m, 3H), 7.52-7.48 (m, 2H), 7.39-7.33 (m, 4H), 7.25-7.21 (m, 3H), 7.07-6.98 (m, 2H), 6.90 (d, J=2.8 Hz, 1H), 6.35 (d, J=8.0 Hz, 1H), 5.67 (d, J=5.2 Hz, 1H), 4.35 (q, J=7.2 Hz, 2H), 1.57 (t, J=7.2 Hz, 3H), 1.54 (s, 6H)

MS: 637 [M+H]⁺

EXAMPLE 44

Preparation of 4-ethoxy-N-(3-fluoro-4-((5-(3-(methylcarbamoyl)phenyl)pyrrolo[1,2-b]pyridazin-4-yl)oxy)phenyl)-1-(4-fluorophenyl)-2-oxo-1,2-dihydropyridin-3-carboxamide

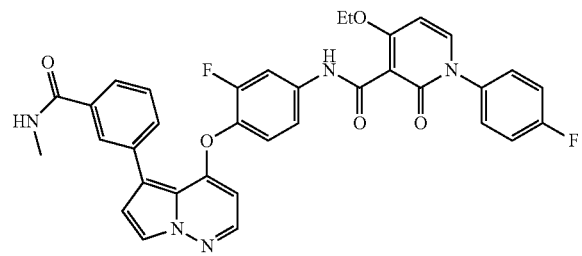 [SMILES: CCOc1ccn(-c2ccc(F)cc2)c(=O)c1C(=O)Nc1ccc(Oc2ccnn3ccc(-c4cccc(C(=O)NC)c4)c23)c(F)c1]

¹H NMR (400 MHz, CDCl₃) δ 11.68 (s, 1H), 7.99 (d, J=4.8 Hz, 1H), 7.97-7.96 (m, 1H), 7.84 (d, J=5.2 Hz, 1H), 7.81 (d, J=2.8 Hz, 1H), 7.77-7.69 (m, 2H), 7.50 (d, J=7.6 Hz, 1H), 7.41 (t, J=7.6 Hz, 1H), 7.36-7.33 (m, 2H), 7.25-7.21 (m, 3H), 7.03 (t, J=8.8 Hz, 1H), 6.91 (d, J=3.2 Hz, 1H), 6.35 (d, J=8.0 Hz, 1H), 6.2 (br, 1H), 5.71 (d, J=5.2 Hz, 1H), 4.38-4.33 (q, 2H), 2.95 (d, J=5.2 Hz, 3H), 1.58 (t, J=6.8 Hz, 3H)

MS: 636 [M+H]⁺

EXAMPLE 45

Preparation of 3-(4-(4-(4-ethoxy-1-(4-fluorophenyl)-2-oxo-1,2-dihydropyridin-3-carboxamido)-2-fluorophenoxy)pyrrolo[1,2-b]pyridazin-5-yl)benzylcarbamate

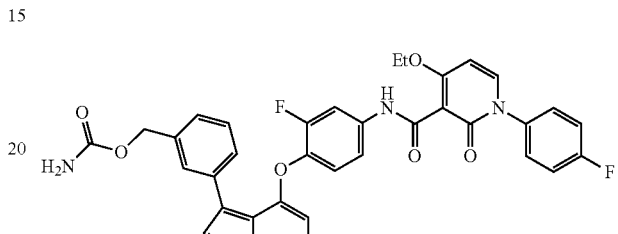

¹H NMR (400 MHz, CDCl₃) δ 11.60 (s, 1H), 7.91 (d, J=2.4 Hz, 1H), 7.88 (d, J=2.4 Hz, 1H), 7.82 (d, J=5.2 Hz, 1H), 7.79 (d, J=2.8 Hz, 1H), 7.68 (s, 1H), 7.61-7.59 (m, 1H), 7.50 (d, J=8.0 Hz, 1H), 7.37-7.32 (m, 3H), 7.26-7.20 (m, 4H), 7.05 (t, J=8.8 Hz, 1H), 6.89 (d, J=2.8 Hz, 1H), 6.36 (d, J=7.6 Hz, 1H), 5.69 (d, J=5.6 Hz, 1H), 5.09 (s, 2H), 4.48 (br, 2H), 4.38-4.35 (q, 2H), 1.59 (d, J=6.8 Hz, 3H)

MS: 652 [M+H]+

EXAMPLE 46

Preparation of 4-ethoxy-N-(3-fluoro-4-((5-(3-(1-hydroxyethyl)phenyl)pyrrolo[1,2-b]pyridazin-4-yl)oxy)phenyl)-1-(4-fluorophenyl)-2-oxo-1,2-dihydropyridin-3-carboxamide

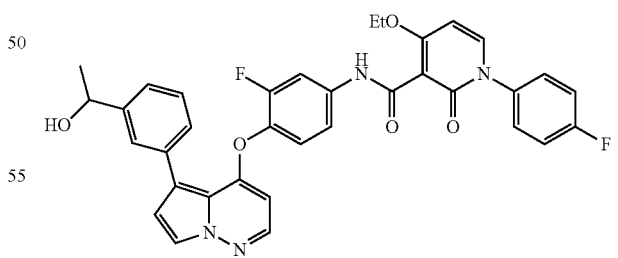

¹H NMR (400 MHz, CDCl₃) δ 11.59 (s, 1H), 7.93-7.89 (m, 1H), 7.82-7.79 (m, 2H), 7.67 (s, 1H), 7.56-7.53 (m, 1H), 7.49 (d, J=7.8 Hz, 1H), 7.37-7.31 (m, 3H), 7.25-7.21 (m, 4H), 7.04 (t, J=8.7 Hz, 1H), 6.89 (d, J=2.8 Hz, 1H), 6.35 (d, J=7.9 Hz, 1H), 5.69-5.68 (m, 1H), 4.89 (q, J=6.4 Hz, 1H), 1.57 (t, J=7.0 Hz, 3H), 1.45 (d, J=6.4 Hz, 3H)

MS: 623 [M+H]⁺

EXAMPLE 47

Preparation of N-(3-fluoro-4-((5-(3-(1-hydroxyethyl)phenyl)pyrrolo[1,2-b]pyridazin-4-yl)oxy)phenyl)-1-(4-fluorophenyl)-2-oxo-1,2-dihydropyridin-3-carboxamide

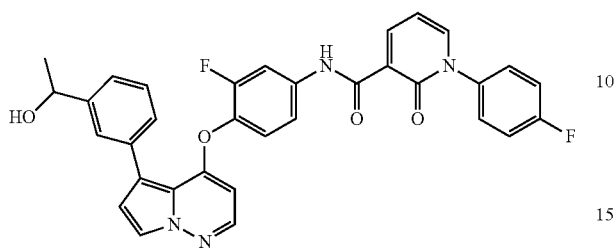

¹H NMR (400 MHz, CDCl₃) δ 11.99 (s, 1H), 8.75-8.73 (m, 1H), 7.94-7.91 (m, 1H), 7.85-7.82 (m, 2H), 7.69 (s, 1H), 7.64-7.55 (m, 2H), 7.43-7.26 (m, 7H), 7.11 (t, J=8.6 Hz, 1H), 6.92 (d, J=2.7 Hz, 1H), 6.62 (t, J=6.8 Hz, 1H), 5.72 (d, J=5.3 Hz, 1H), 4.92 (q, J=6.2 Hz, 1H), 1.48 (q, J=6.4 Hz, 3H)
MS: 579 [M+H]⁺

EXAMPLE 48

Preparation of N-(3-fluoro-4-((5-(3-(1-hydroxyethyl)phenyl)pyrrolo[1,2-b]pyridazin-4-yl)oxy)phenyl)-4-methoxy-2-oxo-1-phenyl-1,2-dihydropyridin-3-carboxamide

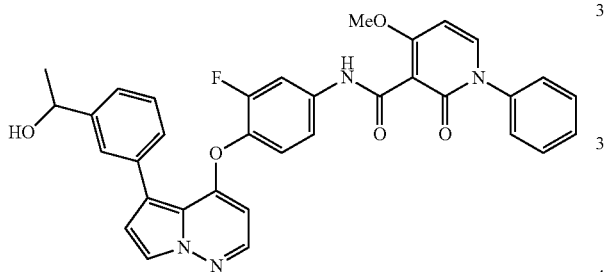

¹H NMR (400 MHz, CDCl₃) δ 11.77 (s, 1H), 7.95-7.91 (m, 1H), 7.83-7.79 (m, 2H), 7.66 (s, 1H), 7.58-7.49 (m, 5H), 7.37-7.31 (m, 3H), 7.24-7.18 (m, 2H), 7.04 (t, J=8.7 Hz, 1H), 6.91-6.88 (m, 1H), 6.39 (d, J=7.8 Hz, 1H), 5.70 (d, J=5.3 Hz, 1H), 4.87 (q, J=6.4 Hz, 1H), 4.10 (s, 3H), 1.49-1.43 (m, 3H)
MS: 591 [M+H]⁺

EXAMPLE 49

Preparation of 4-ethoxy-N-(3-fluoro-4-((5-(pyrimidin-5-yl)pyrrolo[1,2-b]pyridazin-4-yl)oxy)phenyl)-1-(4-fluorophenyl)-2-oxo-1,2-dihydropyridin-3-carboxamide

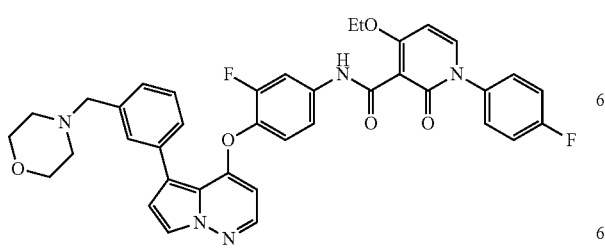

¹H NMR (400 MHz, DMSO-d₆) δ 10.61 (s, 1H), 9.04 (d, J=2.8 Hz, 3H), 8.11 (t, J=3.2 Hz, 2H), 7.93-7.90 (m, 1H), 7.86 (d, J=7.6 Hz, 1H), 7.53-7.44 (m, 4H), 7.39-7.34 (m, 2H), 7.21 (d, J=2.8 Hz, 1H), 6.51 (d, J=8.0 Hz, 1H), 5.96 (d, J=5.2 Hz, 1H), 4.25 (q, J=6.8 Hz, 2H), 1.30 (t, J=7.2 Hz, 3H)
MS: 678 [M+H]+

EXAMPLE 50

Preparation of 4-ethoxy-N-(3-fluoro-4-((5-(3-morpholin-4-carbonylphenyl)pyrrolo[1,2-b]pyridazin-4-yl)oxy)phenyl)-1-(4-fluorophenyl)-2-oxo-1,2-dihydropyridin-3-carboxamide

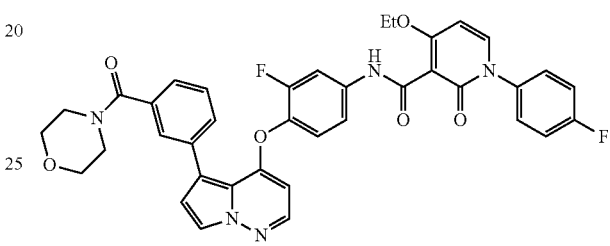

¹H NMR (400 MHz, CDCl₃) δ 11.6 (s, 1H), 7.94 (d, J=2.4 Hz, 1H), 7.83 (s, 1H), 7.65 (m, 2H), 7.50 (d, J=8.0 Hz, 1H), 7.40-7.15 (m, 7H), 6.04 (t, J=8.8 Hz, 1H), 6.86 (d, J=2.8 Hz, 1H), 6.35 (d, J=7.6 Hz, 1H), 5.68 (d, J=5.2 Hz, 1H), 4.36 (q, J=7.3 Hz, 2H), 1.58 (t, J=7.3 Hz, 3H)
MS: 692 [M+H]⁺

EXAMPLE 51

Preparation of 4-ethoxy-N-(3-fluoro-4-((5-(2-morpholidinpyridin-4-yl)pyrrolo[1,2-b]pyridazin-4-yl)oxy)phenyl)-1-(4-fluorophenyl)-2-oxo-1,2-dihydropyridin-3-carboxamide

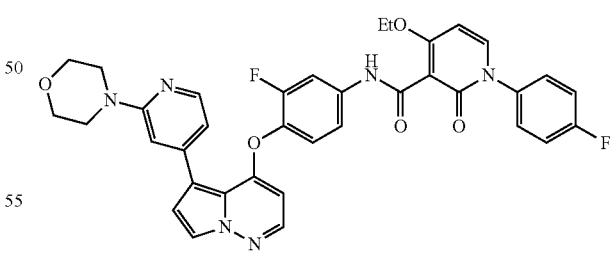

¹H NMR (400 MHz, CDCl₃) δ 11.70 (s, 1H), 8.15 (d, J=5.2 Hz, 1H), 7.99 (d, J=2.4 Hz, 1H), 7.96 (d, J=2.4 Hz, 1H), 7.85 (d, J=5.6 Hz, 1H), 7.80 (d, J=2.4 Hz, 1H), 7.51 (d, J=8 Hz, 1H), 7.37-7.34 (m, 2H), 7.26-7.21 (m, 2H), 7.05-7.00 (m, 2H), 6.96-6.94 (m, 2H), 6.36 (d, J=8.0 Hz, 1H), 5.73 (d, J=5.6 Hz, 1H), 4.39-4.34 (q, 2H), 3.75 (t, J=4.8 Hz, 4H), 3.47 (t, J=5.2 Hz, 4H), 1.59 (d, J=6.8 Hz, 3H)
MS: 665 [M+H]⁺

EXAMPLE 52

Preparation of 4-ethoxy-N-(3-fluoro-4-((5-(3-nitrophenyl)pyrrolo[1,2-b]pyridazin-4-yl)oxy)phenyl)-1-(4-fluorophenyl)-2-oxo-1,2-dihydropyridin-3-carboxamide

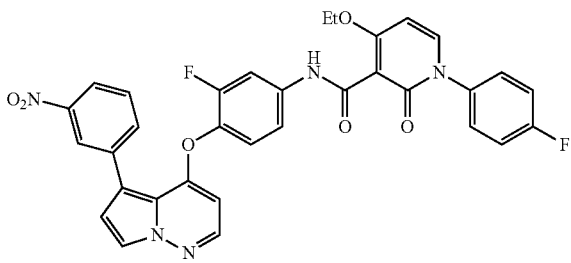 [SMILES: CCOc1ccn(-c2ccc(F)cc2)c(=O)c1C(=O)Nc1ccc(Oc2ccnn3ccc(-c4cccc([N+](=O)[O-])c4)c23)c(F)c1]

$^1$H NMR (400 MHz, DMSO-d$_6$) δ 10.59 (s, 1H), 8.49 (d, J=2.0 Hz, 1H), 8.09-8.07 (m, 4H), 7.94-7.89 (m, 1H), 7.85 (d, J=8.0 Hz, 1H), 7.66 (t, J=8.0 Hz, 1H), 7.48-7.43 (m, 4H), 7.39-7.34 (m, 2H), 7.17 (d, J=3.2 Hz, 1H), 6.51 (d, J=8.0 Hz, 1H), 5.95 (q, J=5.6 Hz, 1H), 4.25 (q, J=7.2 Hz, 2H), 1.30 (t, J=7.2 Hz, 3H)

MS: 624 [M+H]$^+$

EXAMPLE 53

Preparation of 4-ethoxy-N-(3-fluoro-4-((5-(3-aminophenyl)pyrrolo[1,2-b]pyridazin-4-yl)oxy)phenyl)-1-(4-fluorophenyl)-2-oxo-1,2-dihydropyridin-3-carboxamide

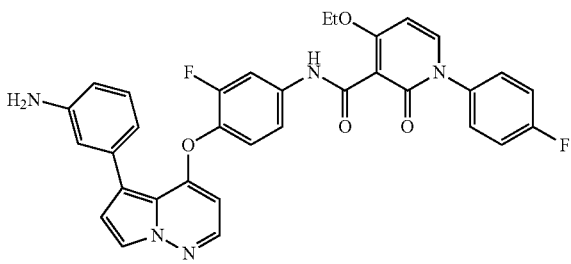 [SMILES: CCOc1ccn(-c2ccc(F)cc2)c(=O)c1C(=O)Nc1ccc(Oc2ccnn3ccc(-c4cccc(N)c4)c23)c(F)c1]

$^1$H NMR (400 MHz, DMSO-d$_6$) δ 10.57 (s, 1H), 7.96 (d, J=5.6 Hz, 1H), 7.96 (d, J=2.8 Hz, 1H), 7.89 (dd, J=11.6 and 2.0 Hz, 1H), 7.85 (d, J=8.0 Hz, 1H), 7.48-7.43 (m, 4H), 7.69-7.34 (m, 2H), 6.97 (t, J=8.0 Hz, 1H), 6.86 (d, J=2.8 Hz, 1H), 6.82-6.74 (m, 1H), 6.51 (d, J=8.0 Hz, 1H), 6.45-6.43 (m, 2H), 5.78 (d, J=4.8 Hz, 1H), 4.94 (s, 2H), 4.25 (q, J=7.2 Hz, 2H), 1.30 (t, J=7.2 Hz, 3H)

MS: 594 [M+H]$^+$

EXAMPLE 54

Preparation of 4-ethoxy-N-(3-fluoro-4-((5-(3-(1-methoxyethyl)phenyl)pyrrolo[1,2-b]pyridazin-4-yl)oxy)phenyl)-1-(4-fluorophenyl)-2-oxo-1,2-dihydropyridin-3-carboxamide

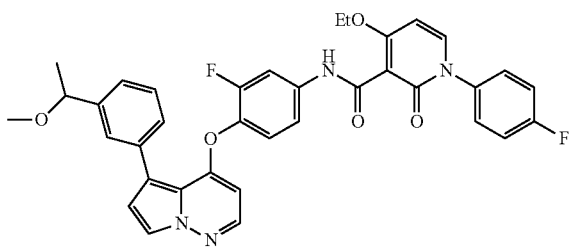 [SMILES: CCOc1ccn(-c2ccc(F)cc2)c(=O)c1C(=O)Nc1ccc(Oc2ccnn3ccc(-c4cccc(C(C)OC)c4)c23)c(F)c1]

$^1$H NMR (400 MHz, DMSO-d$_6$) δ 10.56 (s, 1H), 8.01 (d, J=4.8 Hz, 1H), 7.90 (m, 2H), 7.70-7.30 (m, 9H), 7.16 (d, J=8.0 Hz, 1H), 6.99 (d, J=2.8 Hz, 1H), 6.52 (d, J=8.0 Hz, 1H), 5.84 (d, J=4.8 Hz, 1H), 4.28 (q, J=7.1 Hz, 2H), 3.28 (m, 1H), 2.99 (s, 3H), 1.27 (m, 6H)

MS: 637 [M+H]$^+$

EXAMPLE 55

Preparation of N-(3-fluoro-4-((5-(3-(1-hydroxyethyl)phenyl)pyrrolo[1,2-b]pyridazin-4-yl)oxy)phenyl)-N-(4-fluorophenyl)cyclopropane-1,1-dicarboxamide

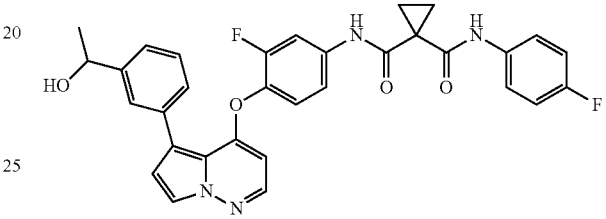

$^1$H NMR (400 MHz, CDCl$_3$) δ 9.91 (s, 1H), 8.14 (s, 1H), 7.83-7.81 (m, 2H), 7.72-7.68 (m, 1H), 7.66 (s, 1H), 7.53 (d, J=7.6 Hz, 1H), 7.45-7.42 (m, 2H), 7.34 (t, J=7.6 Hz, 1H), 7.19-7.16 (m, 1H), 7.12-7.04 (m, 3H), 7.53 (d, J=2.8 Hz, 1H), 5.68 (d, J=5.2 Hz, 1H), 4.89 (q, J=6.4 Hz, 1H), 2.35 (t, J=8.0 Hz, 1H), 1.78 (q, J=5.2 Hz, 2H), 1.60 (q, J=4.4 Hz, 2H), 1.46 (d, J=6.4 Hz, 3H)

MS: 569 [M+H]$^+$

EXAMPLE 56

Preparation of N-(4-((5-(3-((dimethylamino)methyl)phenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

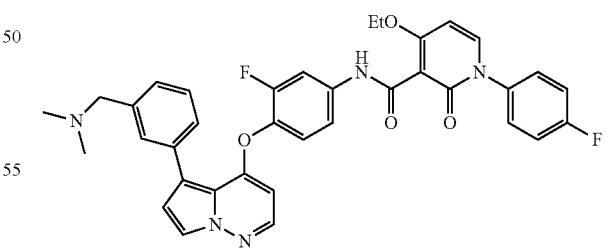

$^1$H NMR (400 MHz, CDCl$_3$) δ 11.62 (s, 1H), 7.94-7.90 (m, 1H), 7.81-7.78 (m, 2H), 7.61 (s, 1H), 7.55-7.52 (m, 1H), 7.50 (d, J=8.0 Hz, 1H), 7.36-7.30 (m, 3H), 7.25-7.18 (m, 4H), 7.05 (t, J=8.8 Hz, 1H), 6.89 (d, J=2.8 Hz, 1H), 6.35 (d, J=8.0 Hz, 1H), 5.67-5.66 (m, 1H), 4.35 (q, J=6.8 Hz, 2H), 3.45 (s, 2H), 2.18 (s, 6H), 1.57 (t, J=7.2 Hz, 3H)

MS: 636 [M+H]$^+$

EXAMPLE 57

Preparation of N-(3-fluoro-4-((5-(pyridin-4-yl)pyrrolo[1,2-b]pyridazin-4-yl)oxy)-phenyl)-1-(4-fluorophenyl)-2-oxo-1,2-dihydropyridin-3-carboxamide

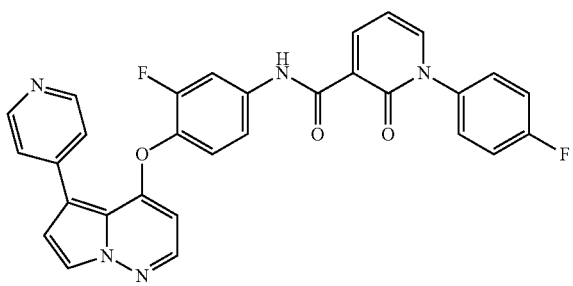 [SMILES: O=C(Nc1ccc(Oc2ccnn3ccc(-c4ccncc4)c23)c(F)c1)c1cccn(-c2ccc(F)cc2)c1=O]

$^1$H NMR (400 MHz, CDCl$_3$) δ 12.02 (s, 1H), 8.76-8.74 (m, 1H), 8.56 (s, 2H), 7.99-7.95 (m, 1H), 7.89 (d, J=5.6 Hz, 1H), 7.84 (d, J=3.2 Hz, 1H), 7.65-7.63 (m, 1H), 7.57 (d, J=6.0 Hz, 2H), 7.42-7.33 (m, 4H), 7.29-7.25 (m, 1H), 7.13-7.09 (m, 1H), 6.96 (d, J=2.8 Hz, 1H), 6.63 (t, J=7.2 Hz, 1H), 5.79-5.78 (m, 1H)

MS: 536 [M+H]$^+$

EXAMPLE 58

Preparation of 4-ethoxy-N-(4-((5-(2-ethoxypyridin-4-yl)pyrrolo[1,2-b]pyridazin-4-yl)-oxy)-3-fluorophenyl)-1-(4-fluorophenyl)-2-oxo-1,2-dihydropyridin-3-carboxamide

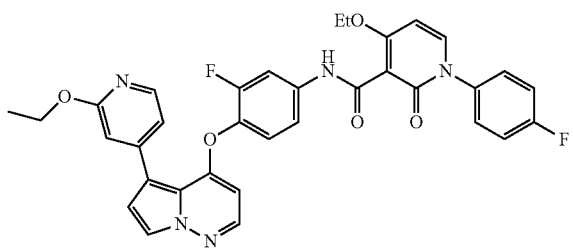 [SMILES: CCOc1cc(-c2ccn3nccc(Oc4ccc(NC(=O)c5c(OCC)ccn(-c6ccc(F)cc6)c5=O)cc4F)c23)ccn1]

$^1$H NMR (400 MHz, CDCl$_3$) δ 11.64 (s, 1H), 8.07 (d, J=5.6 Hz, 1H), 7.94 (dd, J=12.4 and 2.4 Hz, 1H), 7.86 (d, J=5.2 Hz, 1H), 7.80 (d, J=2.8 Hz, 1H), 7.50 (d, J=8.0 Hz, 1H), 7.37-7.33 (m, 2H), 7.29-7.26 (m, 1H), 7.25-7.21 (m, 2H), 7.18 (dd, J=5.2 and 1.6 Hz, 1H), 7.07 (t, J=8.8 Hz, 1H), 6.98 (d, J=1.2 Hz, 1H), 6.93 (d, J=3.2 Hz, 1H), 6.35 (d, J=8.0 Hz, 1H), 5.75 (dd, J=5.6 and 1.2 Hz, 1H), 4.35 (q, J=7.2 Hz, 2H), 4.33 (q, J=7.2 Hz, 2H), 1.58 (t, J=7.2 Hz, 3H), 1.38 (t, J=7.2 Hz, 3H)

MS: 624 [M+H]$^+$

EXAMPLE 59

Preparation of 4-ethoxy-N-(3-fluoro-4-((5-(2-methoxypyridin-4-yl)pyrrolo[1,2-b]pyridazin-4-yl)oxy)phenyl)-1-(4-fluorophenyl)-2-oxo-1,2-dihydropyridin-3-carboxamide

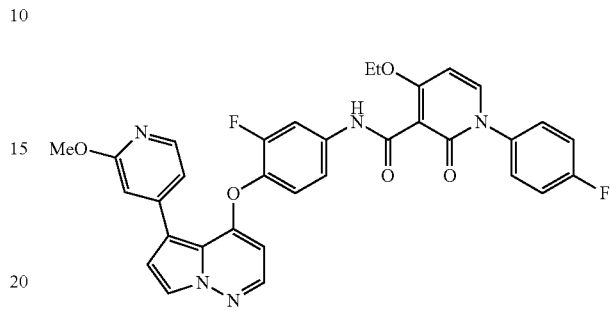

$^1$H NMR (400 MHz, CDCl$_3$) δ 11.64 (s, 1H), 8.10 (d, J=5.2 Hz, 1H), 7.94 (dd, J=2.4 and 12.4 Hz, 1H), 7.86 (d, J=5.2 Hz, 1H), 7.81 (d, J=3.2 Hz, 1H), 7.51 (d, J=7.6 Hz, 1H), 7.38-7.34 (m, 2H), 7.29-7.21 (m, 2H), 7.19 (dd, J=1.2 and 5.6 Hz, 1H), 7.07 (t, J=8.8 Hz, 1H), 7.02 (m, 1H), 6.93 (d, J=3.2 Hz, 1H), 6.36 (d, J=7.6 Hz, 1H), 5.75 (d, J=5.2 Hz, 1H), 4.36 (q, J=7.2 Hz, 1H), 3.93 (s, 3H), 1.58 (t, J=7.2 Hz, 3H)

MS: 610 [M+H]$^+$

EXAMPLE 60

Preparation of N-(3-fluoro-4-((5-(pyridin-4-yl)pyrrolo[1,2-b]pyridazin-4-yl)oxy)phenyl)-4-ethoxy-2-oxo-1-phenyl-1,2-dihydropyridin-3-carboxamide

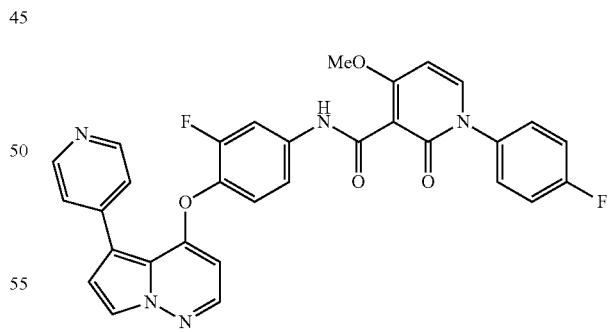

$^1$H NMR (400 MHz, CDCl$_3$) δ 11.75 (s, 1H), 8.53 (d, J=6.0 Hz, 2H), 8.00-7.95 (m, 1H), 7.88 (d, J=5.6 Hz, 1H), 7.83 (d, J=2.8 Hz, 1H), 7.58-7.54 (m, 3H), 7.37-7.34 (m, 3H), 7.30-7.22 (m, 2H), 7.08-7.04 (m, 1H), 6.95 (d, J=2.8 Hz, 1H), 6.40 (d, J=8.0 Hz, 1H), 5.79-5.77 (m, 1H), 4.10 (s, 3H)

MS: 566 [M+H]$^+$

EXAMPLE 61

Preparation of N-(4-((5-(2,6-dimethylpyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide

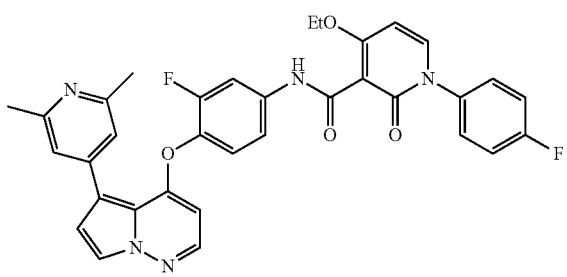 [SMILES: CCOc1ccn(-c2ccc(F)cc2)c(=O)c1C(=O)Nc1ccc(Oc2ccnn3ccc(-c4cc(C)nc(C)c4)c23)c(F)c1]

$^1$H NMR (400 MHz, CDCl$_3$) δ 11.67 (s, 1H), 7.98 (dd, J=12.8 and 2.4 Hz, 1H), 7.88 (d, J=5.2 Hz, 1H), 7.81 (d, J=2.4 Hz, 1H), 7.52 (d, J=7.6 Hz, 1H), 7.38-7.34 (m, 2H), 7.28-7.22 (m, 5H), 7.06 (t, J=8.8 Hz, 1H), 6.93 (d, J=2.8 Hz, 1H), 6.38 (d, J=8.0 Hz, 1H), 5.78 (d, J=5.2 Hz, 1H), 4.36 (q, J=7.2 Hz, 2H), 2.53 (s, 6H), 1.59 (t, J=7.2 Hz, 3H)

MS: 608 [M+H]$^+$

EXAMPLE 62

Preparation of N-(4-((5-(2-(1-hydroxyethyl)pyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide $^1$H NMR (400 MHz, CDCl$_3$) δ 11.67 (s, 1H), 8.46 (d, J=5.2 Hz, 1H), 7.98-7.95 (m, 1H), 7.89 (d, J=5.6 Hz, 1H), 7.83 (d, J=2.8 Hz, 1H), 7.57 (s, 1H), 7.51 (d, J=7.6 Hz, 1H), 7.48-7.47 (m, 1H), 7.38-7.34 (m, 2H), 7.30-7.22 (m, 3H), 7.08-7.03 (m, 1H), 6.97 (d, J=2.8 Hz, 1H), 6.37 (d, J=8.0 Hz, 1H), 5.78 (d, J=5.2 Hz, 1H), 4.87 (q, J=6.4 Hz, 1H), 4.37 (q, J=6.8 Hz, 2H), 1.59 (t, J=6.8 Hz, 3H), 1.44 (d, J=4.8 Hz, 3H)

MS: 624 [M+H]$^+$

EXAMPLE 63

Preparation of N-(4-((5-(3-((dimethylamino)methyl)phenyl)pyrrolo[1,2-b]pyridazin-4-yl)oxy)-3-fluorophenyl)-N-(4-fluorophenyl)cyclopropane-1,1-dicarboxamide

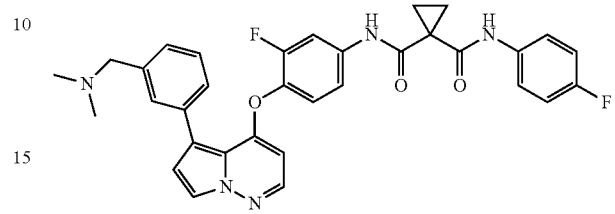

$^1$H NMR (400 MHz, CDCl$_3$) δ 9.94 (s, 1H), 8.10 (s, 1H), 7.82-7.80 (m, 2H), 7.73-7.70 (m, 1H), 7.60 (s, 1H), 7.53 (d, J=6.8 Hz, 1H), 7.46-7.42 (m, 2H), 7.33-7.29 (m, 1H), 7.20-7.17 (m, 2H), 7.14-7.04 (m, 3H), 6.91 (d, J=2.8 Hz, 1H), 5.65 (d, J=5.6 Hz, 1H), 3.42 (s, 2H), 2.18 (s, 6H), 1.82-1.79 (m, 2H), 1.69-1.60 (m, 2H)

MS: 624 [M+H]$^+$

EXAMPLE 64

Preparation of N-(4-((5-(3-aminophenyl)pyrrolo[1,2-b]pyridazin-4-yl)oxy)-3-fluorophenyl)-N-(4-fluorophenyl)cyclopropane-1,1-dicarboxamide

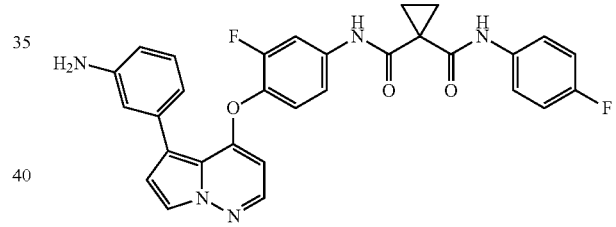

$^1$H NMR (400 MHz, CDCl$_3$) δ 9.92 (s, 1H), 8.24 (s, 1H), 7.81-7.79 (m, 2H), 7.73-7.70 (m, 1H), 7.49-7.42 (m, 2H), 7.18-7.15 (m, 1H), 7.13-7.01 (m, 6H), 6.88 (d, J=2.8 Hz, 1H), 6.59-6.57 (m, 1H), 5.66 (d, J=5.2 Hz, 1H), 1.79-1.76 (m, 2H), 1.69-1.58 (m, 2H)

MS: 540 [M+H]$^+$

EXAMPLE 65

Preparation of N-(4-((5-(3-acetamidophenyl)pyrrolo[1,2-b]pyridazin-4-yl)oxy)-3-fluorophenyl)-N-(4-fluorophenyl)cyclopropane-1,1-dicarboxamide

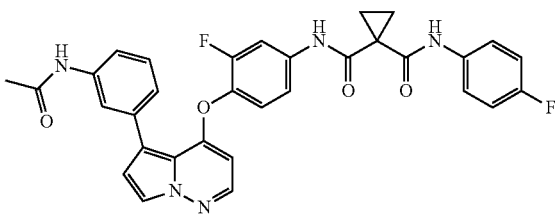 [SMILES: CC(=O)Nc1cccc(-c2ccn3nccc(Oc4ccc(NC(=O)C5(C(=O)Nc6ccc(F)cc6)CC5)cc4F)c23)c1]

¹H NMR (400 MHz, CDCl₃) δ 9.94 (s, 1H), 8.43 (s, 1H), 7.82-7.78 (m, 2H), 7.70-7.67 (m, 1H), 7.61 (s, 1H), 7.47-7.41 (m, 3H), 7.39-7.37 (m, 1H), 7.29-7.24 (m, 2H), 7.14-7.12 (m, 1H), 7.09-7.01 (m, 3H), 6.86 (d, J=2.8 Hz, 1H), 5.68 (d, J=5.2 Hz, 1H), 2.15 (s, 3H), 1.76-1.73 (m, 2H), 1.69-1.57 (m, 2H)

MS: 582 [M+H]⁺

EXAMPLE 66

Preparation of N-(4-((5-(3-amino-4-fluorophenyl)pyrrolo[1,2-b]pyridazin-4-yl)oxy)-3-fluorophenyl)-N-(4-fluorophenyl)cyclopropane-1,1-dicarboxamide

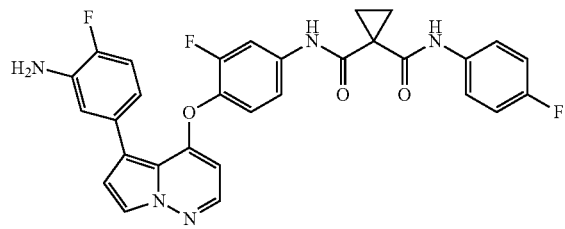 [SMILES: Nc1cc(-c2ccn3nccc(Oc4ccc(NC(=O)C5(C(=O)Nc6ccc(F)cc6)CC5)cc4F)c23)ccc1F]

¹H NMR (400 MHz, CDCl₃) δ 9.95 (s, 1H), 8.18 (s, 1H), 7.81-7.77 (m, 2H), 7.74-7.70 (m, 1H), 7.45-7.42 (m, 2H), 7.19-7.16 (m, 1H), 7.12-7.00 (m, 4H), 6.94 (d, J=8.4 Hz, 2H), 6.83 (d, J=2.8 Hz, 1H), 5.66 (d, J=5.2 Hz, 1H), 3.75 (s, 2H), 1.79-1.75 (m, 2H), 1.65-1.58 (m, 2H)

MS: 558 [M+H]⁺

EXAMPLE 67

Preparation of N-(4-((5-(3-amino-5-cyanophenyl)pyrrolo[1,2-b]pyridazin-4-yl)oxy)-3-fluorophenyl)-N-(4-fluorophenyl)cyclopropane-1,1-dicarboxamide

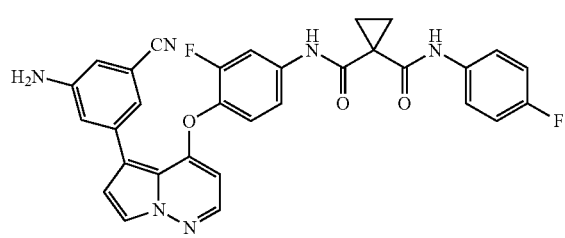 [SMILES: N#Cc1cc(N)cc(-c2ccn3nccc(Oc4ccc(NC(=O)C5(C(=O)Nc6ccc(F)cc6)CC5)cc4F)c23)c1]

¹H NMR (400 MHz, CDCl₃) δ 10.03 (s, 1H), 8.36 (s, 1H), 7.87-7.80 (m, 2H), 7.68-7.63 (m, 3H), 7.55-7.54 (m, 1H), 7.48-7.43 (m, 3H), 7.31 (s, 1H), 7.19 (s, 1H), 7.08-7.03 (m, 2H), 6.86-6.81 (m, 2H), 5.75 (d, J=5.6 Hz, 1H), 1.78-1.69 (m, 2H), 1.65-1.55 (m, 2H)

MS: 565 [M+H]⁺

EXAMPLE 68

Preparation of N-(4-((5-(3-((dimethylamino)methyl)phenyl)pyrrolo[1,2-b]pyridazin-4-yl]oxy)-3-fluorophenyl)-1-(4-fluorophenyl)-6-methyl-2-oxo-1,2-dihydropyridin-3-carboxamide

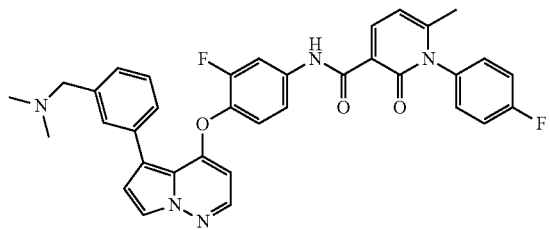 [SMILES: Cc1ccc(C(=O)Nc2ccc(Oc3ccnn4ccc(-c5cccc(CN(C)C)c5)c34)c(F)c2)c(=O)n1-c1ccc(F)cc1]

¹H NMR (400 MHz, CDCl₃) δ 11.89 (s, 1H), 8.63 (d, J=7.6 Hz, 1H), 7.92 (dd, J=12.4 and 2.4 Hz, 1H), 7.81 (d, J=5.2 Hz, 1H), 7.79 (d, J=2.8 Hz, 1H), 7.61 (s, 1H), 7.53 (d, J=7.6 Hz, 1H), 7.33-7.29 (m, 3H), 7.26-7.19 (m, 4H), 7.08 (t, J=8.4 Hz, 1H), 6.90 (d, J=2.8 Hz, 1H), 6.51 (d, J=7.6 Hz, 1H), 5.67 (dd, J=5.2 Hz, 1H), 3.45 (s, 2H), 2.18 (s, 6H), 2.13 (s, 3H)

MS: 589 [M+H]⁺

EXAMPLE 69

Preparation of N-(4-((5-(3-carbamoylphenyl)pyrrolo[1,2-b]pyridazin-4-yl)oxy)-3-fluorophenyl)-N-(4-fluorophenyl)cyclopropane-1,1-dicarboxamide

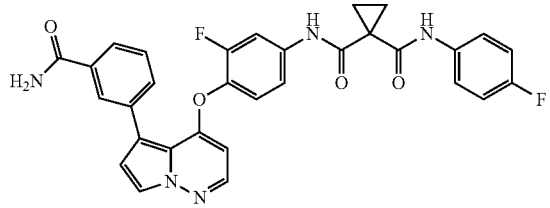 [SMILES: NC(=O)c1cccc(-c2ccn3nccc(Oc4ccc(NC(=O)C5(C(=O)Nc6ccc(F)cc6)CC5)cc4F)c23)c1]

¹H NMR (400 MHz, CDCl₃) δ 10.09 (s, 1H), 8.75 (s, 1H), 7.83-7.81 (m, 2H), 7.78-7.66 (m, 4H), 7.46-7.39 (m, 3H), 7.18-7.16 (m, 1H), 7.07-6.99 (m, 3H), 6.89 (d, J=2.8 Hz, 1H), 6.24 (s, 1H), 5.79 (s, 1H), 5.68 (d, J=5.2 Hz, 1H), 1.73-1.70 (m, 2H), 1.61-1.58 (m, 2H)

MS: 568 [M+H]⁺

EXAMPLE 70

Preparation of N-(4-((5-(3-aminomethylphenyl)pyrrolo[1,2-b]pyridazin-4-yl)oxy)-3-fluorophenyl)-N-(4-fluorophenyl)cyclopropane-1,1-dicarboxamide

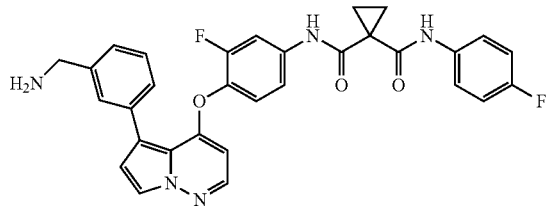 [SMILES: NCc1cccc(-c2ccn3nccc(Oc4ccc(NC(=O)C5(C(=O)Nc6ccc(F)cc6)CC5)cc4F)c23)c1]

¹H NMR (400 MHz, CDCl₃) δ 9.88 (s, 1H), 8.70 (s, 1H), 7.79-7.77 (m, 2H), 7.58-7.43 (m, 5H), 7.31-7.27 (m, 1H), 7.20-7.18 (m, 1H), 7.11-7.09 (m, 1H), 7.05-6.94 (m, 3H), 6.84 (d, J=2.8 Hz, 1H), 5.72 (d, J=5.2 Hz, 1H), 3.93 (s, 2H), 3.13 (q, J=7.2 Hz, 2H), 1.39-1.32 (m, 4H)

MS: 554 [M+H]⁺

EXAMPLE 71

Preparation of N-(4-((5-(3-hydroxymethylphenyl) pyrrolo[1,2-b]pyridazin-4-yl)oxy)-3-fluorophenyl)-N-(4-fluorophenyl)cyclopropane-1,1-dicarboxamide

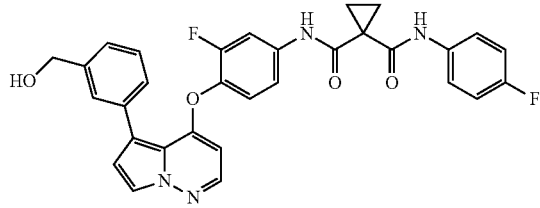 [SMILES: O=C(Nc1ccc(F)cc1)C1(C(=O)Nc2ccc(Oc3ccnn4ccc(-c5cccc(CO)c5)c34)c(F)c2)CC1]

¹H NMR (400 MHz, CDCl₃) δ 9.90 (s, 1H), 8.34 (s, 1H), 7.80-7.79 (m, 2H), 7.68-7.63 (m, 2H), 7.56 (d, J=7.6 Hz, 1H), 7.45-7.40 (m, 2H), 7.33 (t, J=7.6 Hz, 1H), 7.24-7.12 (m, 2H), 7.08-7.01 (m, 3H), 6.88 (d, J=2.8 Hz, 1H), 5.67 (d, J=5.6 Hz, 1H), 4.68 (s, 2H), 1.74-1.71 (m, 2H), 1.61-1.52 (m, 2H)

MS: 555 [M+H]⁺

EXAMPLE 72

Preparation of N-(4-((5-(3-(methylamino)phenyl) pyrrolo[1,2-b]pyridazin-4-yl)oxy)-3-fluorophenyl)-N-(4-fluorophenyl)cyclopropane-1,1-dicarboxamide

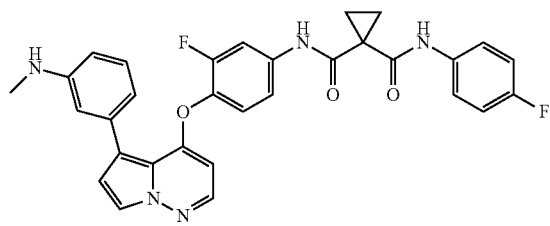 [SMILES: CNc1cccc(-c2ccn3nccc(Oc4ccc(NC(=O)C5(C(=O)Nc6ccc(F)cc6)CC5)cc4F)c23)c1]

¹H NMR (400 MHz, CDCl₃) δ 9.90 (s, 1H), 8.23 (s, 1H), 7.80-7.79 (m, 2H), 7.73-7.69 (m, 1H), 7.46-7.41 (m, 2H), 7.19-7.15 (m, 2H), 7.12-6.99 (m, 4H), 6.95-6.94 (m, 1H), 6.91 (d, J=2.8 Hz, 1H), 6.53-6.51 (m, 1H), 5.63 (d, J=5.2 Hz, 1H), 2.81 (s, 3H), 1.78-1.75 (m, 2H), 1.60-1.57 (m, 2H)

MS: 554 [M+H]⁺

EXAMPLE 73

Preparation of N-(4-((5-(3-(ethylamino)phenyl)pyrrolo[1,2-b]pyridazin-4-yl)oxy)-3-fluorophenyl)-N-(4-fluorophenyl)cyclopropane-1,1-dicarboxamide

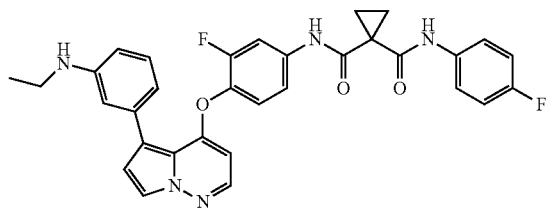 [SMILES: CCNc1cccc(-c2ccn3nccc(Oc4ccc(NC(=O)C5(C(=O)Nc6ccc(F)cc6)CC5)cc4F)c23)c1]

¹H NMR (400 MHz, CDCl₃) δ 9.91 (s, 1H), 8.23 (s, 1H), 7.80-7.79 (m, 2H), 7.73-7.69 (m, 1H), 7.45-7.41 (m, 2H), 7.18-7.03 (m, 5H), 7.00-6.97 (m, 1H), 6.94-6.93 (m, 1H), 6.90 (d, J=2.8 Hz, 1H), 6.52-6.50 (m, 1H), 5.64-5.62 (m, 1H), 3.13 (q, J=7.2 Hz, 2H), 1.78-1.75 (m, 2H), 1.60-1.57 (m, 2H), 1.21 (t, J=2.4, 3H)

MS: 568 [M+H]⁺

EXAMPLE 74

Preparation of N-(4-((5-(1H-indol-6-yl)pyrrolo[1,2-b]pyridazin-4-yl)oxy)-3-fluorophenyl)-N-(4-fluorophenyl)cyclopropane-1,1-dicarboxamide

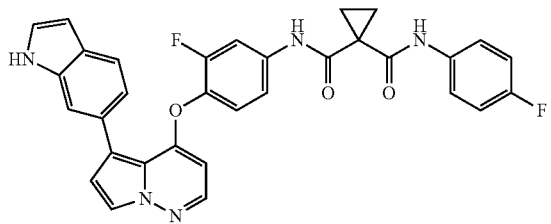 [SMILES: O=C(Nc1ccc(F)cc1)C1(C(=O)Nc2ccc(Oc3ccnn4ccc(-c5ccc6cc[nH]c6c5)c34)c(F)c2)CC1]

¹H NMR (400 MHz, CDCl₃) δ 9.84 (s, 1H), 8.28-8.23 (m, 2H), 7.81-7.77 (m, 2H), 7.68-7.64 (m, 2H), 7.60 (d, J=8.0 Hz, 1H), 7.44-7.39 (m, 3H), 7.14 (t, J=2.8 Hz, 1H), 7.07-6.99 (m, 4H), 6.92 (d, J=2.8 Hz, 1H), 6.52-6.51 (m, 1H), 5.60 (d, J=0.8 Hz, 1H), 1.72-1.69 (m, 2H), 1.56-1.52 (m, 2H)

MS: 564 [M+H]⁺

EXAMPLE 75

Preparation of N-(4-((5-(2-chloro-5-((dimethylamino)methyl)phenyl)pyrrolo[1,2-b]pyridazin-4-yl)oxy)-3-fluorophenyl)-N-(4-fluorophenyl)cyclopropane-1,1-dicarboxamide

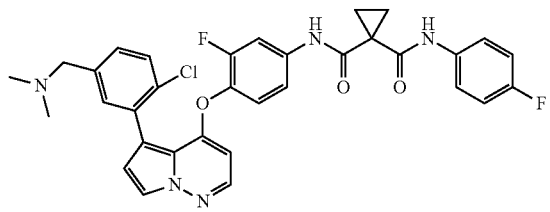 [SMILES: CN(C)Cc1ccc(Cl)c(-c2ccn3nccc(Oc4ccc(NC(=O)C5(C(=O)Nc6ccc(F)cc6)CC5)cc4F)c23)c1]

¹H NMR (400 MHz, CDCl₃) δ 9.98 (s, 1H), 8.07 (s, 1H), 7.84 (d, J=5.6 Hz, 1H), 7.80 (d, J=2.8 Hz, 1H), 7.73 (dd, J=2.4, 12 Hz, 1H), 7.51 (t, 1H), 7.48 (s, 1H), 7.42-7.46 (m, 2H), 7.19-7.21 (m, 2H), 7.13 (t, 1H), 7.04-7.09 (m, 2H), 6.89 (d, J=2.8 Hz, 1H), 5.69 (dd, J=0.8, 5.2 Hz, 1H), 3.38 (s, 2H), 2.27 (s, 6H), 1.89 (t, 2H), 4.60 (t, 2H)

MS: 616 [M+H]⁺

EXAMPLE 76

Preparation of N-(4-((5-(5-((dimethylamino)methyl)-2-fluorophenyl)pyrrolo[1,2-b]pyridazin-4-yl)oxy)-3-fluorophenyl)-N-(4-fluorophenyl)cyclopropane-1,1-dicarboxamide

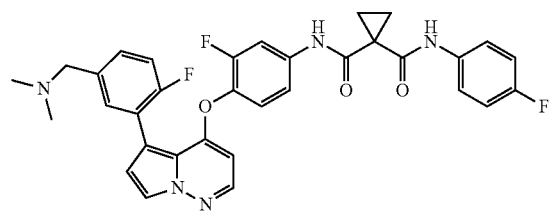 [SMILES: CN(C)Cc1ccc(F)c(-c2ccn3nccc(Oc4ccc(NC(=O)C5(C(=O)Nc6ccc(F)cc6)CC5)cc4F)c23)c1]

¹H NMR (400 MHz, CDCl₃) δ 10.13 (s, 1H), 8.64 (s, 1H), 7.83 (d, J=5.6 Hz, 1H), 7.80 (d, J=2.8 Hz, 1H), 7.71 (dd, J=2.4, 12 Hz, 1H), 7.42-7.45 (m, 2H), 7.36 (s, 1H), 7.26-7.29 (m, 1H), 7.19-7.22 (m, 1H), 7.01-7.11 (m, 3H), 6.95 (dd, J=1.2, 9.2 Hz, 1H), 6.88 (d, J=2.8 Hz, 1H), 5.70 (d, J=5.2 Hz 1H), 3.58 (s, 2H), 2.33 (s, 6H), 1.74-1.77 (m, 2H), 1.60-1.63 (m, 2H)

MS: 600 [M+H]⁺

EXAMPLE 77

Preparation of N-(4-((5-(3-((dimethylamino)methyl)-5-fluorophenyl)pyrrolo[1,2-b]pyridazin-4-yl)oxy)-3-fluorophenyl)-N-(4-fluorophenyl)cyclopropane-1,1-dicarboxamide

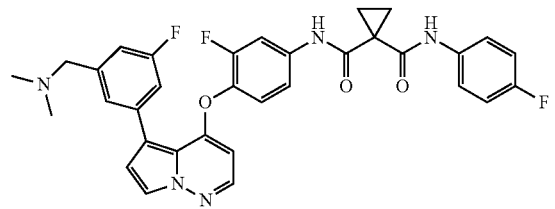 [SMILES: CN(C)Cc1cc(F)cc(-c2ccn3nccc(Oc4ccc(NC(=O)C5(C(=O)Nc6ccc(F)cc6)CC5)cc4F)c23)c1]

¹H NMR (400 MHz, CDCl₃) δ 10.12 (s, 1H), 8.71 (s, 1H), 7.81-7.84 (m, 2H), 7.68 (dd, J=2, 12 Hz, 1H), 7.41 (m, 1H), 7.41-7.48 (m, 3H), 7.18 (m, 2H), 7.00-7.10 (m, 3H), 6.90-6.91 (m, 1H), 5.67 (d, J=5.2 Hz, 1H), 3.58 (s, 2H), 2.27 (s, 6H), 1.75 (t, 2H), 1.63 (t, 2H)

MS: 600 [M+H]⁺

EXAMPLE 78

Preparation of N-(4-((5-(3-amino-4-methyl)-5-fluorophenyl)pyrrolo[1,2-b]pyridazin-4-yl)oxy)-3-fluorophenyl)-N-(4-fluorophenyl)cyclopropane-1,1-dicarboxamide

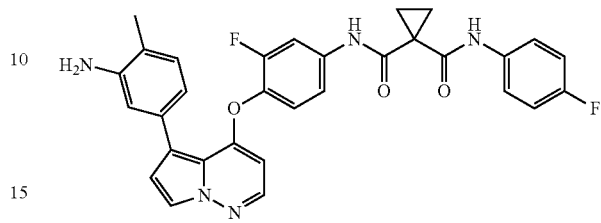

¹H NMR (400 MHz, CDCl₃) δ 9.95 (s, 1H), 8.45 (s, 1H), 7.79-7.68 (m, 3H), 7.44-7.40 (m, 2H), 7.16-6.99 (m, 6H), 6.86 (d, J=2.8 Hz, 1H), 6.18-6.16 (m, 1H), 5.63 (d, J=5.2 Hz, 1H), 2.17 (s, 3H), 1.78-1.71 (m, 2H), 1.60-1.53 (m, 2H)

MS: 554 [M+H]⁺

EXAMPLE 79

Preparation of N-(4-((5-(3-amino-2-methyl)-5-fluorophenyl)pyrrolo[1,2-b]pyridazin-4-yl)oxy)-3-fluorophenyl)-N-(4-fluorophenyl)cyclopropane-1,1-dicarboxamide

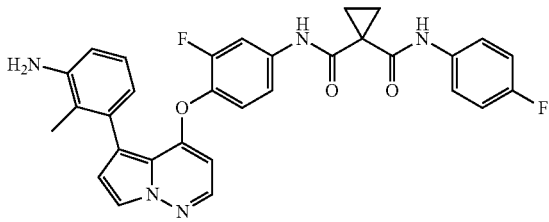 [SMILES: Cc1c(N)cccc1-c1ccn2nccc(Oc3ccc(NC(=O)C4(C(=O)Nc5ccc(F)cc5)CC4)cc3F)c12]

¹H NMR (400 MHz, CDCl₃) δ 10.37 (s, 1H), 8.69 (s, 1H), 7.79-7.78 (m, 2H), 7.62-7.58 (m, 2H), 7.47-7.40 (m, 2H), 7.12-7.10 (m, 1H), 7.03-6.92 (m, 3H), 6.83 (d, J=7.6 Hz, 1H), 6.71 (d, J=2.4 Hz, 1H), 6.62 (d, J=8.0 Hz, 1H), 5.58 (d, J=5.2 Hz, 1H), 2.09 (s, 3H), 1.71-1.68 (m, 2H), 1.59-1.56 (m, 2H)

MS: 554 [M+H]⁺

EXAMPLE 80

Preparation of N-(3-fluoro-4-((5-(3-((methylamino)methyl)phenyl)pyrrolo[1,2-b]pyridazin-4-yl)oxy)phenyl)-N-(4-fluorophenyl)cyclopropane-1,1-dicarboxamide

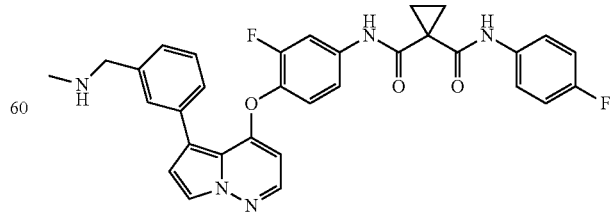

¹H NMR (400 MHz, CDCl₃) δ 9.91 (s, 1H), 8.37 (s, 1H), 7.83 (d, J=5.2 Hz, 1H), 7.81 (d, J=2.8 Hz, 1H), 7.68 (dd,

J=2.4 Hz and 12.4 Hz, 1H), 7.52-7.58 (m, 2H), 7.40-7.47 (m, 2H), 7.32 (t, 1H), 7.16-7.21 (m, 3H), 7.07 (q, 3H), 6.90 (d, J=2.4 Hz, 1H), 5.70 (d, J=5.2 Hz, 1H), 3.79 (s, 2H), 2.37 (s, 3H), 1.77-1.96 (m, 2H), 1.69 (s, 1H), 1.59-1.63 (m, 2H)

MS: 568 [M+H]+

EXAMPLE 81

Preparation of N-(4-((5-(3-((ethylamino)methyl)phenyl)pyrrolo[1,2-b]pyridazin-4-yl)oxy)-3-fluorophenyl)-N-(4-fluorophenyl)cyclopropane-1,1-dicarboxamide

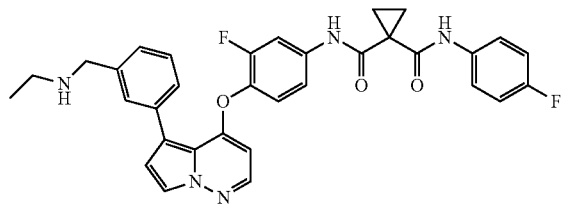 [SMILES: CCNCc1cccc(-c2ccn3nccc(Oc4ccc(NC(=O)C5(C(=O)Nc6ccc(F)cc6)CC5)cc4F)c23)c1]

¹H NMR (400 MHz, CDCl₃) δ 9.95 (s, 1H), 8.47 (s, 1H), 7.82 (d, J=5.2 Hz, 1H), 7.80 (d, J=2.8 Hz, 1H), 7.69 (dd, J=2.4 Hz and 12.4 Hz, 1H), 7.60 (s, 1H), 7.54-7.56 (m, 1H), 7.42-7.47 (m, 2H), 7.32 (t, 1H), 7.24 (s, 1H), 7.17-7.19 (m, 1H), 7.02-7.10 (m, 3H), 6.90 (d, J=2.8 Hz, 1H), 5.67 (d, J=5.2 Hz, 1H), 3.85 (s, 2H), 2.68 (q, 2H), 1.75-1.78 (m, 2H), 1.59-1.62 (m, 2H), 1.41 (s, 1H)

MS: 582 [M+H]+

EXAMPLE 82

Preparation of N-(4-((5-(3-amino-4-methoxy)-5-fluorophenyl)pyrrolo[1,2-b]pyridazin-4-yl)oxy)-3-fluorophenyl)-N-(4-fluorophenyl)cyclopropane-1,1-dicarboxamide

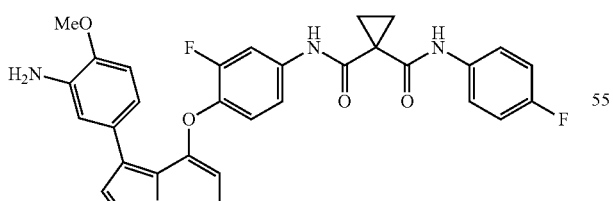

¹H NMR (400 MHz, CDCl₃) δ 9.93 (s, 1H), 8.29 (s, 1H), 7.78-7.77 (m, 2H), 7.72-7.68 (m, 2H), 7.44-7.40 (m, 2H), 7.16-6.99 (m, 6H), 6.83 (d, J=2.8 Hz, 1H), 6.78 (d, J=8.4 Hz, 1H), 3.84 (s, 5H), 1.76-1.73 (m, 2H), 1.59-1.56 (m, 2H)

MS: 570 [M+H]+

EXAMPLE 83

Preparation of N-(4-((5-(5-amino-2-fluoro)-5-fluorophenyl)pyrrolo[1,2-b]pyridazin-4-yl)oxy)-3-fluorophenyl)-N-(4-fluorophenyl)cyclopropane-1,1-dicarboxamide

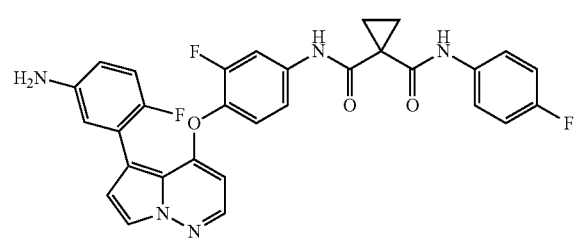 [SMILES: Nc1ccc(F)c(-c2ccn3nccc(Oc4ccc(NC(=O)C5(C(=O)Nc6ccc(F)cc6)CC5)cc4F)c23)c1]

¹H NMR (400 MHz, MeOD) δ 7.86 (d, J=5.2 Hz, 1H), 7.80 (d, J=2.4 Hz, 1H), 7.75-7.71 (m, 1H), 7.56-7.52 (m, 2H), 7.33-7.29 (m, 1H), 7.19-7.15 (m, 1H), 7.07-7.03 (m, 2H), 6.88-6.85 (m, 1H), 6.83-6.80 (m, 2H), 6.64-6.60 (m, 1H), 5.69 (d, J=0.8 Hz, 1H)

MS: 558 [M+H]+

EXAMPLE 84

Preparation of N-(4-((5-(3-(methylcarbamoyl)phenyl)pyrrolo[1,2-b]pyridazin-4-yl)oxy)-3-fluorophenyl)-N-(4-fluorophenyl)cyclopropane-1,1-dicarboxamide

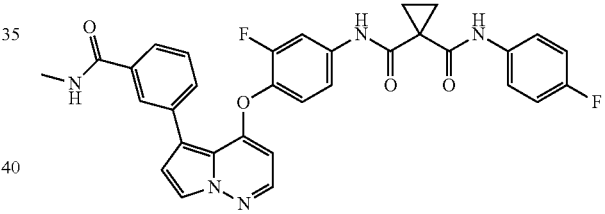

¹H NMR (400 MHz, CDCl₃) δ 10.15 (s, 1H), 8.73 (s, 1H), 7.83-7.80 (m, 2H), 7.70-7.64 (m, 5H), 7.46-7.41 (m, 2H), 7.17-7.15 (m, 1H), 7.04-6.99 (m, 3H), 6.89 (d, J=2.8 Hz, 1H), 6.31 (d, J=4.8 Hz, 1H), 5.68 (d, J=5.2 Hz, 1H), 2.96 (s, 3H), 1.75-1.72 (m, 2H), 1.68-1.60 (m, 2H)

MS: 582 [M+H]+

EXAMPLE 85

Preparation of N-(4-((5-(3-cyanomethylphenyl)pyrrolo[1,2-b]pyridazin-4-yl)oxy)-3-fluorophenyl)-N-(4-fluorophenyl)cyclopropane-1,1-dicarboxamide

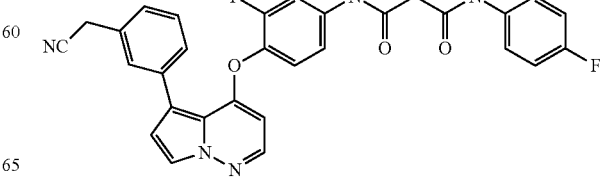

$^1$H NMR (400 MHz, CDCl$_3$) δ 9.90 (s, 1H), 8.44 (s, 1H), 7.84-7.81 (m, 2H), 7.72-7.68 (m, 1H), 7.60-7.57 (m, 2H), 7.46-7.41 (m, 2H), 7.35 (t, J=7.6 Hz, 1H), 7.18-7.15 (m, 2H), 7.12-7.07 (m, 1H), 7.06-7.00 (m, 2H), 6.89 (d, J=2.8 Hz, 1H), 5.71 (d, J=5.2 Hz, 1H), 3.74 (s, 2H), 1.75-1.72 (m, 2H), 1.61-1.58 (m, 2H)

MS: 564 [M+H]$^+$

EXAMPLE 86

Preparation of N-(4-((5-3-aminophenyl)pyrrolo[1,2-b]pyridazin-4-yl)oxy)-3-fluorophenyl)-1-(4-fluorophenyl)-6-methyl-2-oxo-1,2-dihydropyridin-3-carboxamide

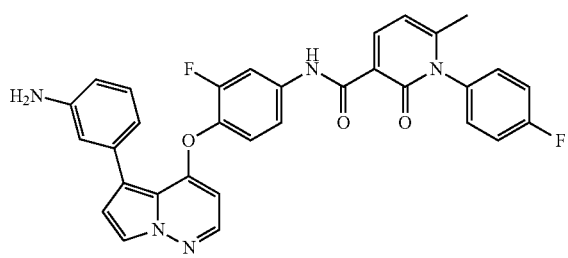 [SMILES: Cc1ccc(C(=O)Nc2ccc(Oc3ccnn4ccc(-c5cccc(N)c5)c34)c(F)c2)c(=O)n1-c1ccc(F)cc1]

$^1$H NMR (400 MHz, CDCl$_3$) δ 11.90 (s, 1H), 8.65 (d, J=7.6 Hz, 1H), 7.94 (dd, J=12.4 and 2.4 Hz, 1H), 7.82 (d, J=5.6 Hz, 1H), 7.79 (d, J=2.8 Hz, 1H), 7.35-7.24 (m, 5H), 7.17-7.11 (m, 1H), 7.09-7.03 (m, 3H), 6.89 (d, J=2.8 Hz, 1H), 6.61-6.58 (m, 1H), 6.52 (d, J=7.6 Hz, 1H), 5.70 (dd, J=5.2 Hz, 1H), 3.87 (br s, 2H), 2.14 (s, 3H)

MS: 564 [M+H]$^+$

EXPERIMENTAL EXAMPLE

Analysis of the Inhibition of c-Met Activity (ADP-Glo™ Kinase Assay

The inhibitory effect of the compounds of the present invention on the activity of c-Met was confirmed as follows.

Specifically, 250 μM G4Y1 peptide, which serves as a substrate for c-Met enzyme (2 ng/μL), and 50 μM ATP were subjected to an enzyme reaction in a reaction buffer (40 mM Tris-HCl (pH 7.5), 20 mM MgCl$_2$, 0.1 mg/mL bovine serum albumin, and 50 μM DTT). The compounds prepared in Examples and comparative compounds were treated at various concentrations and reacted at room temperature for 1 hour, sequentially added with ADP-Glo™ Reagent and the Kinase detection reagent, and reacted at room temperature for 40 minutes and 30 minutes, respectively.

Then, luminescence of the compounds was measured using the Wallaac Victor 2™ (PerkinElmer life sciences, 1420-042). The activity of c-Met inhibitors was evaluated by analyzing the data based on the measured RLU values. The activity of c-Met inhibitors was evaluated as the percentage of remaining activity of the c-Met enzyme in the samples treated with the compounds at concentrations to be tested, with the RLU value of the sample set at 100% control group. The concentrations of the compounds which showed the 50% inhibition of c-Met activity compared to that of control group were determined as IC$_{50}$ value (nM). The results are shown in Table 1 below.

TABLE 1

| Example No. | c-Met IC$_{50}$ |
|---|---|
| 7 | A |
| 23 | A |
| 29 | A |
| 43 | A |
| 46 | A |
| 47 | A |
| 49 | A |
| 50 | A |
| 53 | A |
| 56 | A |
| 63 | A |
| 67 | A |
| 70 | A |
| 73 | A |
| 75 | A |
| 76 | A |
| 77 | A |
| 78 | A |
| 79 | A |
| 80 | A |
| 81 | A |
| 82 | A |
| 83 | A |
| 85 | A |

A: <40 nM, B: 40 nM to 100 nM, C: 100 nM to 500 nM, D: >500 nM

As shown in Table 1 above, the compounds of the present invention have excellent inhibitory effect against the activity of c-Met.

What is claimed is:

1. A compound represented by the following Formula 1 or a pharmaceutically acceptable salt thereof:

[Formula 1]

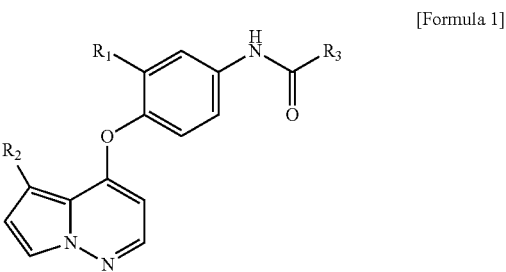

wherein, in Formula 1,

R$_1$ is H or halogen;

R$_2$ is aryl or heteroaryl selected from the group consisting of indolyl, phenyl, pyrazinyl, pyrazolyl, pyridinyl, pyrimidinyl, thiazolyl, and thienyl, wherein the aryl or the heteroaryl is unsubstituted or substituted with one or two substituents, which are respectively and independently selected from the group consisting of

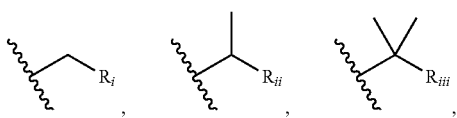

C$_{1-4}$ alkyl, C$_{1-4}$ alkoxy, halogen, nitro, cyano, amino, NH(C$_{1-4}$ alkyl), NH-acetyl, CO—H, CO—(C$_{1-4}$ alkyl), CO-morpholino, CO—NH$_2$, CO—NH(C$_{1-4}$ alkyl), CO—N(C$_{1-4}$ alkyl)$_2$, morpholino, piperazinyl, piperidinyl, SO$_2$—(C$_{1-4}$ alkyl), SO$_2$—NH$_2$, SO$_2$—NH(C$_{1-4}$ alkyl), and SO$_2$—N(C$_{1-4}$ alkyl)$_2$; wherein R$_i$ is selected from the group consisting of hydroxy, O—CH$_2$CH$_2$—O—CH$_3$, OCO—NH$_2$, morpholino, amino, NH(C$_{1-4}$ alkyl), and N(C$_{1-4}$ alkyl)$_2$; R$_{ii}$ is hydroxy or C$_{1-4}$ alkoxy; and R$_{iii}$ is hydroxy; and R$_3$ is

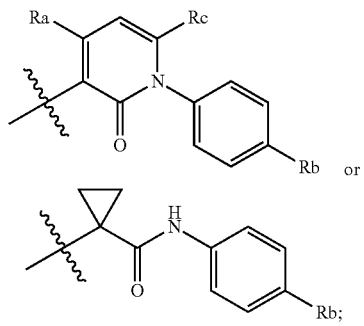

wherein Ra is H or C$_{1-4}$ alkoxy; Rb is H or halogen; and Rc is H or C$_{1-4}$ alkyl.

2. The compound or pharmaceutically acceptable salt thereof of claim 1, wherein R$_1$ is H or fluoro.

3. The compound or pharmaceutically acceptable salt thereof of claim 1, wherein the substituent for the aryl or heteroaryl in R$_2$ is selected from the group consisting of

(wherein R$_i$ is selected from the group consisting of hydroxy, O—CH$_2$CH$_2$—O—CH$_3$, OCO—NH$_2$, morpholino, amino, NHCH$_3$, NHCH$_2$CH$_3$, and N(CH$_3$)$_2$),

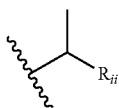

(wherein R$_{ii}$ is hydroxy or methoxy),

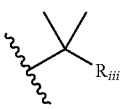

(wherein R$_{iii}$ is hydroxy), methyl, methoxy, fluoro, chloro, nitro, cyano, amino, methylamino, ethylamino, NH-acetyl, CO—H, CO—CH$_3$, CO-morpholino, CO—NH$_2$, CO—NHCH$_3$, CO—N(CH$_3$)$_2$, morpholino, piperazinyl, piperidinyl, SO$_2$—CH$_3$, SO$_2$—CH$_2$CH$_3$, SO$_2$—NH$_2$, SO$_2$—NHCH$_3$, and SO$_2$—N(CH$_3$)$_2$.

4. The compound or pharmaceutically acceptable salt thereof of claim 1, wherein R$_2$ is phenyl, wherein the phenyl is unsubstituted or substituted with one or two substituents, which are respectively and independently selected from the group consisting of

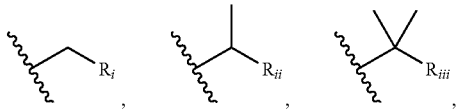

C$_{1-4}$ alkoxy, halogen, nitro, cyano, amino, NH(C$_{1-4}$ alkyl), CO—H, CO—(C$_{1-4}$ alkyl), CO-morpholino, CO—NH$_2$, CO—NH(C$_{1-4}$ alkyl), CO—N(C$_{1-4}$ alkyl)$_2$, SO$_2$—(C$_{1-4}$ alkyl), SO$_2$—NH$_2$, SO$_2$—NH(C$_{1-4}$ alkyl), and SO$_2$—N(C$_{1-4}$ alkyl)$_2$, in which R$_i$ is selected from the group consisting of hydroxy, O—CH$_2$CH$_2$—O—CH$_3$, OCO—NH$_2$, morpholino, amino, NH(C$_{1-4}$ alkyl), and N(C$_{1-4}$ alkyl)$_2$, R$_{ii}$ is hydroxy or C$_{1-4}$ alkoxy, and R$_{iii}$ is hydroxy.

5. The compound or pharmaceutically acceptable salt thereof of claim 1, wherein R$_2$ is pyridinyl, in which the pyridinyl is unsubstituted or substituted with a substituent, which is selected from the group consisting of

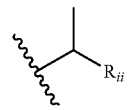

C$_{1-4}$ alkoxy, halogen, amino, NH-acetyl, CO—(C$_{1-4}$ alkyl), morpholino, and piperazinyl, and R$_{ii}$ is hydroxy.

6. The compound or pharmaceutically acceptable salt thereof of claim 1, wherein R$_2$ is pyrazolyl, in which the pyrazolyl is unsubstituted or substituted with C$_{1-4}$ alkyl, SO$_2$—(C$_{1-4}$ alkyl), or piperidinyl.

7. The compound or pharmaceutically acceptable salt thereof of claim 1, wherein R$_2$ is indolyl, pyrazinyl, pyrimidinyl, thiazolyl, or thienyl, in which the indolyl, pyrazinyl, pyrimidinyl, thiazolyl, or thienyl are unsubstituted.

8. The compound or pharmaceutically acceptable salt thereof of claim 1, wherein Ra is H, methoxy, or ethoxy.

9. The compound or pharmaceutically acceptable salt thereof of claim 1, wherein Rb is H or fluoro.

10. The compound or pharmaceutically acceptable salt thereof of claim 1, wherein Rc is H or methyl.

11. The compound or pharmaceutically acceptable salt thereof of claim 1, wherein the compound represented by Formula 1 is selected from the group consisting of:
1) 4-ethoxy-N-(3-fluoro-4-((5-(3-(hydroxymethyl)phenyl)pyrrolo[1,2-b]pyridazin-4-yl)oxy)phenyl)-1-(4-fluorophenyl)-2-oxo-1,2-dihydropyridin-3-carboxamide,
2) 4-ethoxy-N-(3-fluoro-4-((5-phenylpyrrolo[1,2-b]pyridazin-4-yl)-oxy)phenyl)-1-(4-fluorophenyl)2-oxo-1,2-dihydropyridin-3-carboxamide,
3) 4-ethoxy-N-(3-fluoro-4-((5-(pyridin-3-pyrrolo[1,2-b]pyridazin-4-yl)oxy)phenyl)-1-(4-fluorophenyl)-2-oxo-1,2-dihydropyridin-3-carboxamide,
4) 4-ethoxy-N-(3-fluoro-4-((5-thiazol-2-yl)pyrrolo[1,2-b]pyridazin-4-yl)oxy)phenyl)-1-(4-fluorophenyl)-2-oxo-1,2-dihydropyridin-3-carboxamide,
5) 4-ethoxy-N-(2-fluoro-4-((pyrazin-2-yl)pyrrolo[1,2-b]pyridazin-4-yl)oxy)phenyl)-1-(4-fluorophenyl)-2-oxo-1,2-dihydropyridin-3-carboxamide,
6) 4-ethoxy-N-(2-fluoro-4-((5-(1-methyl-1H-pyrazol-4-yl)pyrrolo[1,2-b]pyridazin-4-yl)oxy)phenyl)-1-(4-fluorophenyl)-2-oxo-1,2-dihydropyridin-3-carboxamide, 7) 4-ethoxy-N-(3-fluoro-4-(5-pyridin-4-yl)pyrrolo[1,2-b]pyridazin-4-yl)oxy)phenyl)-1-(4-fluorophenyl)-2-oxo-1,2-dihydropyridin-3-carboxamide,
8) 4-ethoxy-N-(3-fluoro-4-((5-(pyrimidin-5-yl)pyrrolo[1,2-b]pyridazin-4-yl)oxy)phenyl)-1-(4-fluorophenyl)-2-oxo-1,2-dihydropyridin-3-carboxamide,
9) 4-ethoxy-N-(3-fluoro-4-((5-(6-methoxypyridin-3-yl)pyrrolo[1,2-b]pyridazin-4-yl)oxy)phenyl)-1-(4-fluorophenyl)-2-oxo-1,2-dihydropyridin-3-carboxamide,
10) 4-ethoxy-N-(3-fluoro-4-((5-(thiophen-3-yl)pyrrolo[1,2-b]pyridazin-4-yl)oxy)phenyl)-1-(4-fluorophenyl)-2-oxo-1,2-dihydropyridin-3-carboxamide,
11) 4-ethoxy-N-(3-fluoro-4-((5-(4-methoxyphenyl)pyrrolo[1,2-b]pyridazin-4-yl)oxy)phenyl)-1-(4-fluorophenyl)-2-oxo-1,2-dihydropyridin-3-carboxamide,
12) 4-ethoxy-N-(3-fluoro-4-((5-(2-fluorophenyl)pyrrolo[1,2-b]pyridazin-4-yl)oxy)phenyl)-1-(4-fluorophenyl)-2-oxo-1,2-dihydropyridin-3-carboxamide,
13) N-(4-((5-(3,4-dimethoxyphenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
14) 4-ethoxy-N-(3-fluoro-4-((5-(4-fluorophenyl)pyrrolo[1,2-b]pyridazin-4-yl)oxy)phenyl)-1-(4-fluorophenyl)-2-oxo-1,2-dihydropyridin-3-carboxamide,
15) 4-ethoxy-N-(3-fluoro-4-((5-(thiophen-2-yl)pyrrolo[1,2-b]pyridazin-4-yl)oxy)phenyl)-1-(4-fluorophenyl)-2-oxo-1,2-dihydropyridin-3-carboxamide,
16) N-(4-((5-(2-chloropyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
17) N-(4-((5-(1H-pyrazol-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
18) 4-ethoxy-N-(3-fluoro-4-((5-(1-methylsulfonyl)-1H-pyrazol-4-yl)pyrrolo[1,2-b]pyridazin-4-yl)oxy)phenyl)-1-(4-fluorophenyl)-2-oxo-1,2-dihydropyridin-3-carboxamide,
19) 4-ethoxy-N-(3-fluoro-4-((5-(2-fluoropyridin-4-yl)pyrrolo[1,2-b]pyridazin-4-yl)oxy)phenyl)-1-(4-fluorophenyl)-2-oxo-1,2-dihydropyridin-3-carboxamide,
20) N-(4-((5-(5-chloro-2-methoxypyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
21) N-(4-((5-(6-aminopyridin-3-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
22) 4-ethoxy-N-(3-fluoro-4-((5-(1-piperidin-4-yl)-1H-pyrazol-4-yl)pyrrolo[1,2-b]pyridazin-4-yl)oxy)phenyl)-1-(4-fluorophenyl)-2-oxo-1,2-dihydropyridin-3-carboxamide,
23) 4-ethoxy-N-(3-fluoro-4-((5-(3-formylphenyl)pyrrolo[1,2-b]pyridazin-4-yl)oxy)phenyl)-1-(4-fluorophenyl)-2-oxo-1,2-dihydropyridin-3-carboxamide,
24) 4-ethoxy-N-(3-fluoro-4-((5-(2-(piperazin-1-yl)pyridin-4-yl)pyrrolo[1,2-b]pyridazin-4-yl)oxy)phenyl)-1-(4-fluorophenyl)-2-oxo-1,2-dihydropyridin-3-carboxamide,
25) N-(4-((5-(6-acetamidopyridin-3-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
26) N-(4-((5-(2-acetylpyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
27) N-(4-((5-(3-acetylphenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
28) N-(3-fluoro-4-((5-(pyridin-4-yl)pyrrolo[1,2-b]pyridazin-4-yl)oxy)phenyl)-4-methoxy-2-oxo-1-phenyl-1,2-dihydropyridin-3-carboxamide,
29) N-(3-fluoro-4-((5-(3-hydroxymethyl)phenyl)pyrrolo[1,2-b]pyridazin-4-yl)oxy)phenyl)-1-(4-fluorophenyl)-2-oxo-1,2-dihydropyridin-3-carboxamide,
30) 4-ethoxy-N-(4-((5-(3-(ethylsulfonyl)phenyl)pyrrolo[1,2-b]pyridazin-4-yl)oxy)-3-fluorophenyl)-1-(4-fluorophenyl)-2-oxo-1,2-dihydropyridin-3-carboxamide,
31) 4-ethoxy-N-(3-fluoro-4-((5-(3-(methylsulfonyl)phenyl)pyrrolo[1,2-b]pyridazin-4-yl)oxy)phenyl)-1-(4-fluorophenyl)-2-oxo-1,2-dihydropyridin-3-carboxamide,
32) 4-ethoxy-N-(3-fluoro-4-((5-(3-sulfamoylphenyl)pyrrolo[1,2-b]pyridazin-4-yl)oxy)phenyl)-1-(4-fluorophenyl)-2-oxo-1,2-dihydropyridin-3-carboxamide,
33) N-(4-((5-(3-acetylphenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
34) N-(3-fluoro-4-((5-(pyridin-4-yl)pyrrolo[1,2-b]pyridazin-4-yl)oxy)phenyl)-4-methoxy-2-oxo-1-phenyl-1,2-dihydropyridin-3-carboxamide,
35) N-(4-((5-(3-(N-methylsulfamoylphenyl))pyrrolo[1,2-b]pyridazin-4-yl)oxy)-3-fluorophenyl)-4-ethoxy-1-(4-fluorophenyl)-2-oxo-1,2-dihydropyridin-3-carboxamide,
36) N-(4-((5-(3-(N,N-dimethylsulfamoylphenyl))pyrrolo[1,2-b]pyridazin-4-yl)oxy)-3-fluorophenyl)-4-ethoxy-1-(4-fluorophenyl)-2-oxo-1,2-dihydropyridin-3-carboxamide,
37) 4-ethoxy-N-(3-fluoro-4-((5-(4-nitrophenyl)pyrrolo[1,2-b]pyridazin-4-yl)oxy)phenyl)-1-(4-fluorophenyl)-2-oxo-1,2-dihydropyridin-3-carboxamide,
38) N-(4-((5-(4-aminophenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
39) 4-ethoxy-N-(3-fluoro-4-((5-(3-((2-methoxyethoxy)methyl)phenyl)pyrrolo[1,2-b]pyridazin-4-yl)oxy)phenyl)-1-(4-fluorophenyl)-2-oxo-1,2-dihydropyridin-3-carboxamide,
40) N-(3-fluoro-4-((5-(2-methoxypyridin-4-yl)pyrrolo[1,2-b]pyridazin-4-yl)oxy)phenyl)-1-(4-fluorophenyl)-2-oxo-1,2-dihydropyridin-3-carboxamide,
41) N-(4-((5-(3-(dimethylcarbamoyl)phenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
42) N-(3-fluoro-4-((5-(pyridin-4-yl)pyrrolo[1,2-b]pyridazin-4-yl)oxy)phenyl)-N-(4-fluorophenyl)cyclopropane-1,1-dicarboxyamide,
43) 4-ethoxy-N-(3-fluoro-4-((5-(3-(2-hydroxypropan-2-yl)phenyl)pyrrolo[1,2-b]pyridazin-4-yl)oxy)phenyl)-1-(4-fluorophenyl)-2-oxo-1,2-dihydropyridin-3-carboxamide,
44) 4-ethoxy-N-(3-fluoro-4-((5-(3-(methylcarbamoyl)phenyl)pyrrolo[1,2-b]pyridazin-4-yl)oxy)phenyl)-1-(4-fluorophenyl)-2-oxo-1,2-dihydropyridin-3-carboxamide, 45) 3-(4-(4-(4-ethoxy-1-(4-fluorophenyl)-2-oxo-1,2-dihydropyridin-3-carboxamido)-2-fluorophenoxy)pyrrolo[1,2-b]pyridazin-5-yl)benzylcarbamate,
46) 4-ethoxy-N-(3-fluoro-4-((5-(3-(1-hydroxyethyl)phenyl)pyrrolo[1,2-b]pyridazin-4-yl)oxy)phenyl)-1-(4-fluorophenyl)-2-oxo-1,2-dihydropyridin-3-carboxamide,
47) N-(3-fluoro-4-((5-(3-(1-hydroxyethyl)phenyl)pyrrolo[1,2-b]pyridazin-4-yl)oxy)phenyl)-1-(4-fluorophenyl)-2-oxo-1,2-dihydropyridin-3-carboxamide,
48) N-(3-fluoro-4-((5-(3-(1-hydroxyethyl)phenyl)pyrrolo[1,2-b]pyridazin-4-yl)oxy)phenyl)-4-methoxy-2-oxo-1-phenyl-1,2-dihydropyridin-3-carboxamide,
49) 4-ethoxy-N-(3-fluoro-4-((5-(pyrimidin-5-yl)pyrrolo[1,2-b]pyridazin-4-yl)oxy)phenyl)-1-(4-fluorophenyl)-2-oxo-1,2-dihydropyridin-3-carboxamide,
50) 4-ethoxy-N-(3-fluoro-4-((5-(3-morpholin-4-carbonylphenyl)pyrrolo[1,2-b]pyridazin-4-yl)oxy)phenyl)-1-(4-fluorophenyl)-2-oxo-1,2-dihydropyridin-3-carboxamide,
51) 4-ethoxy-N-(3-fluoro-4-((5-(2-morpholidinpyridin-4-yl)pyrrolo[1,2-b]pyridazin-4-yl)oxy)phenyl)-1-(4-fluorophenyl)-2-oxo-1,2-dihydropyridin-3-carboxamide,
52) 4-ethoxy-N-(3-fluoro-4-((5-(3-nitrophenyl)pyrrolo[1,2-b]pyridazin-4-yl)oxy)phenyl)-1-(4-fluorophenyl)-2-oxo-1,2-dihydropyridin-3-carboxamide,
53) 4-ethoxy-N-(3-fluoro-4-((5-(3-aminophenyl)pyrrolo[1,2-b]pyridazin-4-yl)oxy)phenyl)-1-(4-fluorophenyl)-2-oxo-1,2-dihydropyridin-3-carboxamide,
54) 4-ethoxy-N-(3-fluoro-4-((5-(3-(1-methoxyethyl)phenyl)pyrrolo[1,2-b]pyridazin-4-yl)oxy)phenyl)-1-(4-fluorophenyl)-2-oxo-1,2-dihydropyridin-3-carboxamide,
55) N-(3-fluoro-4-((5-(3-(1-hydroxyethyl)phenyl)pyrrolo[1,2-b]pyridazin-4-yl)oxy)phenyl)-N-(4-fluorophenyl)cyclopropane-1,1-dicarboxamide,
56) N-(4-((5-(3-((dimethylamino)methyl)phenyl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
57) N-(3-fluoro-4-((5-(pyridin-4-yl)pyrrolo[1,2-b]pyridazin-4-yl)oxy)-phenyl)-1-(4-fluorophenyl)-2-oxo-1,2-dihydropyridin-3-carboxamide,
58) 4-ethoxy-N-(4-((5-(2-ethoxypyridin-4-yl)pyrrolo[1,2-b]pyridazin-4-yl)-oxy)-3-fluorophenyl)-1-(4-fluorophenyl)-2-oxo-1,2-dihydropyridin-3-carboxamide,
59) 4-ethoxy-N-(3-fluoro-4-((5-(2-methoxypyridin-4-yl)pyrrolo[1,2-b]pyridazin-4-yl)oxy)phenyl)-1-(4-fluorophenyl)-2-oxo-1,2-dihydropyridin-3-carboxamide,
60) N-(3-fluoro-4-((5-(pyridin-4-yl)pyrrolo[1,2-b]pyridazin-4-yl)oxy)phenyl)-4-ethoxy-2-oxo-1-phenyl-1,2-dihydropyridin-3-carboxamide,
61) N-(4-((5-(2,6-dimethylpyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
62) N-(4-((5-(2-(1-hydroxyethyl)pyridin-4-yl)pyrrolo[1,2-b]pyridazin-4-yl)oxy)-3-fluorophenyl)-4-ethoxy-1-(4-fluorophenyl)-2-oxo-1,2-dihydropyridin-3-carboxamide,
63) N-(4-((5-(3-((dimethylamino)methyl)phenyl)pyrrolo[1,2-b]pyridazin-4-yl)oxy)-3-fluorophenyl)-N-(4-fluorophenyl)cyclopropane-1,1-dicarboxamide,
64) N-(4-((5-(3-aminophenyl)pyrrolo[1,2-b]pyridazin-4-yl)oxy)-3-fluorophenyl)-N-(4-fluorophenyl)cyclopropane-1,1-dicarboxamide,
65) N-(4-((5-(3-acetamidophenyl)pyrrolo[1,2-b]pyridazin-4-yl)oxy)-3-fluorophenyl)-N-(4-fluorophenyl)cyclopropane-1,1-dicarboxamide,
66) N-(4-((5-(3-amino-4-fluorophenyl)pyrrolo[1,2-b]pyridazin-4-yl)oxy)-3-fluorophenyl)-N-(4-fluorophenyl)cyclopropane-1,1-dicarboxamide,
67) N-(4-((5-(3-amino-5-cyanophenyl)pyrrolo[1,2-b]pyridazin-4-yl)oxy)-3-fluorophenyl)-N-(4-fluorophenyl)cyclopropane-1,1-dicarboxamide,
68) N-(4-((5-(3-((dimethylamino)methyl)phenyl)pyrrolo[1,2-bpyridazin-4-yl]oxy)-3-fluorophenyl)-1-(4-fluorophenyl)-6-methyl-2-oxo-1,2-dihydropyridin-3-carboxamide,
69) N-(4-((5-(3-carbamoylphenyl)pyrrolo[1,2-b]pyridazin-4-yl)oxy)-3-fluorophenyl)-N-(4-fluorophenyl)cyclopropane-1,1-dicarboxamide,
70) N-(4-((5-(3-aminomethylphenyl)pyrrolo[1,2-b]pyridazin-4-yl)oxy)-3-fluorophenyl)-N-(4-fluorophenyl)cyclopropane-1,1-dicarboxamide,
71) N-(4-((5-(3-hydroxymethylphenyl)pyrrolo[1,2-b]pyridazin-4-yl)oxy)-3-fluorophenyl)-N-(4-fluorophenyl)cyclopropane-1,1-dicarboxamide,
72) N-(4-((5-(3-(methylamino)phenyl)pyrrolo[1,2-b]pyridazin-4-yl)oxy)-3-fluorophenyl)-N-(4-fluorophenyl)cyclopropane-1,1-dicarboxamide,
73) N-(4-((5-(3-(ethylamino)phenyl)pyrrolo[1,2-b]pyridazin-4-yl)oxy)-3-fluorophenyl)-N-(4-fluorophenyl)cyclopropane-1,1-dicarboxamide,
74) N-(4-((5-(1H-indol-6-yl)pyrrolo[1,2-b]pyridazin-4-yl)oxy)-3-fluorophenyl)-N-(4-fluorophenyl)cyclopropane-1,1-dicarboxamide,
75) N-(4-((5-(2-chloro-5-((dimethylamino)methyl)phenyl)pyrrolo[1,2-b]pyridazin-4-yl)oxy)-3-fluorophenyl)-N-(4-fluorophenyl)cyclopropane-1,1-dicarboxamide,
76) N-(4-((5-(5-((dimethylamino)methyl)-2-fluorophenyl)pyrrolo[1,2-b]pyridazin-4-yl)oxy)-3-fluorophenyl)-N-(4-fluorophenyl)cyclopropane-1,1-dicarboxamide,
77) N-(4-((5-(3-((dimethylamino)methyl)-5-fluorophenyl)pyrrolo[1,2-b]pyridazin-4-yl)oxy)-3-fluorophenyl)-N-(4-fluorophenyl)cyclopropane-1,1-dicarboxamide,
78) N-(4-((5-(3-amino-4-methyl)-5-fluorophenyl)pyrrolo[1,2-b]pyridazin-4-yl)oxy)-3-fluorophenyl)-N-(4-fluorophenyl)cyclopropane-1,1-dicarboxamide,
79) N-(4-((5-(3-amino-2-methyl)-5-fluorophenyl)pyrrolo[1,2-b]pyridazin-4-yl)oxy)-3-fluorophenyl)-N-(4-fluorophenyl)cyclopropane-1,1-dicarboxamide,
80) N-(3-fluoro-4-((5-(3-((methylamino)methyl)phenyl)pyrrolo[1,2-b]pyridazin-4-yl)oxy)phenyl)-N-(4-fluorophenyl)cyclopropane-1,1-dicarboxamide,
81) N-(4-((5-(3-((ethylamino)methyl)phenyl)pyrrolo[1,2-b]pyridazin-4-yl)oxy)-3-fluorophenyl)-N-(4-fluorophenyl)cyclopropane-1,1-dicarboxamide,
82) N-(4-((5-(3-amino-4-methoxy)-5-fluorophenyl)pyrrolo[1,2-b]pyridazin-4-yl)oxy)-3-fluorophenyl)-N-(4-fluorophenyl)cyclopropane-1,1-dicarboxamide,
83) N-(4-((5-(5-amino-2-fluoro)-5-fluorophenyl)pyrrolo[1,2-b]pyridazin-4-yl)oxy)-3-fluorophenyl)-N-(4-fluorophenyl)cyclopropane-1,1-dicarboxamide,
84) N-(4-((5-(3-(methylcarbamoyl)phenyl)pyrrolo[1,2-b]pyridazin-4-yl)oxy)-3-fluorophenyl)-N-(4-fluorophenyl)cyclopropane-1,1-dicarboxamide,
85) N-(4-((5-(3-cyanomethylphenyl)pyrrolo[1,2-b]pyridazin-4-yl)oxy)-3-fluorophenyl)-N-(4-fluorophenyl)cyclopropane-1,1-dicarboxamide, and 86) N-(4-((5-3-aminophenyl)pyrrolo[1,2-b]pyridazin-4-yl)oxy)-3-fluorophenyl)-1-(4-fluorophenyl)-6-methyl-2-oxo-1,2-dihydropyridin-3-carboxamide.

12. A pharmaceutical composition comprising a compound of claim 1 or a pharmaceutically acceptable salt thereof as an active ingredient.

13. The pharmaceutical composition of claim 12, further comprising a pharmaceutically acceptable carrier, diluent, or excipient.

14. A pharmaceutical composition comprising a compound of claim 11 or a pharmaceutically acceptable salt thereof as an active ingredient.

15. The pharmaceutical composition of claim 14, further comprising a pharmaceutically acceptable carrier, diluent, or excipient.

* * * * *